(12) United States Patent
Park et al.

(10) Patent No.: US 9,391,280 B2
(45) Date of Patent: Jul. 12, 2016

(54) HETEROCYCLIC COMPOUND AND ORGANIC LIGHT-EMITTING DEVICE INCLUDING THE SAME

(71) Applicant: SAMSUNG DISPLAY CO., LTD., Yongin (KR)

(72) Inventors: Jun-Ha Park, Yongin (KR); Seok-Hwan Hwang, Yongin (KR); Young-Kook Kim, Yongin (KR); Hye-Jin Jung, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 381 days.

(21) Appl. No.: 13/928,370

(22) Filed: Jun. 26, 2013

(65) Prior Publication Data
US 2014/0209871 A1 Jul. 31, 2014

(30) Foreign Application Priority Data

Jan. 30, 2013 (KR) .......................... 10-2013-0010706

(51) Int. Cl.
| | |
|---|---|
| H01L 51/50 | (2006.01) |
| H01L 51/00 | (2006.01) |
| C07D 209/56 | (2006.01) |
| C09K 11/06 | (2006.01) |

(52) U.S. Cl.
CPC .......... *H01L 51/006* (2013.01); *H01L 51/0061* (2013.01); *H01L 51/0072* (2013.01); *C07D 209/56* (2013.01); *C09K 11/06* (2013.01); *C09K 2211/1018* (2013.01); *C09K 2211/1029* (2013.01); *H01L 51/5012* (2013.01); *H01L 51/5072* (2013.01); *H01L 51/5092* (2013.01)

(58) Field of Classification Search
None
See application file for complete search history.

(56) References Cited

U.S. PATENT DOCUMENTS

| | | | |
|---|---|---|---|
| 3,968,051 A | 7/1976 | Stamm et al. | |
| 4,521,605 A | 6/1985 | Okazaki et al. | |
| 4,720,432 A | 1/1988 | VanSlyke et al. | |
| 5,061,569 A | 10/1991 | VanSlyke et al. | |
| 5,591,554 A | 1/1997 | Mishra et al. | |
| 5,645,948 A | 7/1997 | Shi et al. | |
| 6,465,115 B2 | 10/2002 | Shi et al. | |
| 6,596,415 B2 | 7/2003 | Shi et al. | |
| 6,660,410 B2 | 12/2003 | Hosokawa | |
| 6,670,054 B1 | 12/2003 | Hu et al. | |
| 6,979,414 B2 | 12/2005 | Hosokawa | |
| 7,051,949 B2 | 5/2006 | Aiyama | |
| 7,053,255 B2 | 5/2006 | Ikeda et al. | |
| 7,233,019 B2 | 6/2007 | Ionkin et al. | |
| 7,429,372 B2 | 9/2008 | Pez et al. | |
| 7,571,894 B2 | 8/2009 | Sotoyama | |
| 2001/0046612 A1 | 11/2001 | Lee et al. | |
| 2004/0053069 A1 | 3/2004 | Sotoyama et al. | |
| 2007/0231503 A1* | 10/2007 | Hwang | C09K 11/06 428/1.1 |
| 2009/0019768 A1 | 1/2009 | Toseland et al. | |
| 2010/0109511 A1 | 5/2010 | Kim et al. | |
| 2012/0211733 A1 | 8/2012 | Hwang et al. | |
| 2014/0175398 A1* | 6/2014 | Kim | C07D 405/14 257/40 |
| 2015/0041775 A1* | 2/2015 | Jeong | H01L 51/0094 257/40 |
| 2015/0053940 A1* | 2/2015 | Kim | H01L 51/0052 257/40 |

FOREIGN PATENT DOCUMENTS

| | | | | |
|---|---|---|---|---|
| GB | WO 2011116866 A1 * | 9/2011 | ........... | C08G 61/123 |
| JP | 10-17860 | 1/1998 | | |
| JP | 11-87067 | 3/1999 | | |
| JP | 4060669 B2 | 3/2008 | | |
| KR | 10-0346984 B1 | 7/2002 | | |
| KR | 10-0351234 B1 | 9/2002 | | |
| KR | 10-0525408 | 2/2005 | | |
| KR | 10-2006-0006760 | 1/2006 | | |
| KR | 10-0573137 B1 | 4/2006 | | |

(Continued)

OTHER PUBLICATIONS

Tang et al., Organic electroluminescent diodes, Research Laboratories, Corporate Resdearch Group, Eastman Kodak Company, Rochester, New York 14650, Appl. Phys. Lett. 51 (12), Sep. 21, 1987, 913-915.

(Continued)

*Primary Examiner* — Jennifer Chriss
*Assistant Examiner* — Dylan Kershner
(74) *Attorney, Agent, or Firm* — Lewis Roca Rothgerber Christie LLP

(57) ABSTRACT

Provided is a heterocyclic compound represented by Formula 1 below and an organic light-emitting device including the heterocyclic compound of Formula 1:

<Formula 1>

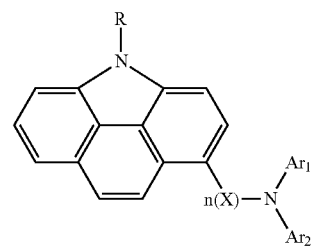

wherein substituents in Formula 1 above are defined as in the specification.

20 Claims, 1 Drawing Sheet

(56) References Cited

FOREIGN PATENT DOCUMENTS

| KR | 10-2010-0048608 | 5/2010 |
|---|---|---|
| WO | WO 02/20694 A1 | 3/2002 |

OTHER PUBLICATIONS

Adachi et al., Confinement of charge carriers and molecular excitons within 5-nm-thick emitter layer in organic electroluminescent devices with a double heterostructure, Department of Materials Science and Technology, Graduate School of Engineering Sciences, Kyushu University, Kasuga-shi, Fukuoka 816, Japan, Appl. Phys. Lett. 57(6), Aug. 6, 1990, 531-533.

Sakamoto et al., Synthesis, Characterization, and Electron-Transport Property of Perfluorinated Phenylene Dendrimers, J. Am. Chem. Soc. 2000, 122, 1832-1833.

Yamaguchi et al., Diphenylamino-Substituted 2,5-Diarylsiloles for Single-Layer Organic Electroluminescent Devices, Chemistry Letters 2001, Institute for Chemical Research, Kyoto University, Uji, Kyoto, 611-0011, 98-99.

Johansson et al., Solid-State Amplified Spontaneous Emission in Some Spiro-Type Molecules: A New Concept for the Design of Solid-State Lasing Molecules, Advanced Materials, Adv. Mater. 1998, 10, No. 14, 1136-1141.

Tao et al., Sharp green electroluminescence from 1H-pyrazolo[3,4-b]quinoline-based light-emitting diodes, Appl. Phys. Lett. 77, 1575 (2000); doi: 10. 1063/1.1309016. pp. 1575-1577.

Internet: 2009 Fall Assembly and Symposium. vol. 34, No. 2, 2009; Publication Date: Oct. 8, 2009-Oct. 9, 2009; Title: A novel conjugated polymer based on 4H-benzo[def]carbazole backbone for OLED, 2 pages.

Internet: http://www.sigmaaldrich.com/catalog/search?interface=All&term=4H-; Title: 4H-Benzo[def]carbazole; Proposed Disclosure, 2 pages.

\* cited by examiner

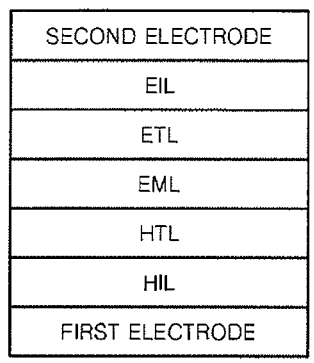

HETEROCYCLIC COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2013-0010706, filed on Jan. 30, 2013, in the Korean Intellectual Property Office, the disclosure of which is incorporated herein in its entirety by reference.

BACKGROUND

1. Field

The following description relates to a heterocyclic compound and an organic light-emitting device including the same.

2. Description of the Related Art

Organic light-emitting devices (OLEDs) are self-emitting devices that have advantages such as wide viewing angles, excellent contrast, a quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. The HTL, the EML, and the ETL are organic thin films formed of organic compounds.

An operating principle of an OLED having the above-described structure is as follows:

When a voltage is applied between the anode and the cathode, holes injected from the anode move to the EML via the HTL, and electrons injected from the cathode move to the EML via the ETL. The holes and electrons (carriers) recombine in the organic EML to generate excitons. When the excitons drop from an excited state to a ground state, light is emitted.

There is an ongoing demand for a material having improved electrical stability, high charge-transfer or emission capability, a high glass transition temperature, and capable of preventing crystallization, relative to existing unimolecular materials.

SUMMARY

Aspects of the present invention are directed toward a novel compound with improved characteristics, and a high-efficiency, low-voltage, high-luminance, and long-lifetime organic light-emitting device including the novel compound. The novel compound according to an embodiment has improved electrical characteristics, good charge transporting capabilities, improved emission capability, and a high glass transition temperature (Tg) that is high enough to prevent crystallization. The novel compound according to an embodiment is suitable as an electron transporting or injecting material for fluorescent or phosphorescent devices of any color, or as a red green, blue, or white light-emitting material.

According to an embodiment of the present invention, there is provided a heterocyclic compound represented by Formula 1 below:

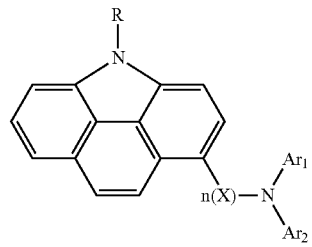

In Formula 1,

R may be a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

X may be a divalent linking group that is a substituted or unsubstituted C6-C60 arylene group, or a substituted or unsubstituted C6-C60 condensed polycyclic group; and $Ar_1$ or $Ar_2$ may be each independently a substituted or unsubstituted C6-C60 aryl group, a substituted or unsubstituted C2-C60 heteroaryl group, or a substituted or unsubstituted C6-C60 condensed polycyclic group, wherein at least one of $Ar_1$ and $Ar_2$ is a C6-C60 aryl group that is substituted with an electron-attracting moiety, and n is an integer from 0 to 10.

According to another embodiment of the present invention, there is provided an organic light-emitting device including a first electrode; a second electrode; and an organic layer between the first electrode and the second electrode, wherein the organic layer comprises the heterocyclic compound above.

According to another embodiment of the present invention, there is provided a flat panel display device including the organic light-emitting device, wherein the first electrode of the organic light-emitting device is electrically connected to a source electrode or a drain electrode of a thin-film transistor.

BRIEF DESCRIPTION OF THE DRAWING

The above and other features and advantages of the present invention will become more apparent by describing in detail exemplary embodiments thereof with reference to the attached drawings in which:

The drawing is a schematic view of a structure of an organic light-emitting device according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a compound represented by Formula 1 below:

<Formula 1>

In Formula 1,

R may be a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

X may be a divalent linking group that is a substituted or unsubstituted C6-C60 arylene group, or a substituted or unsubstituted C6-C60 condensed polycyclic group; and $Ar_1$ or $Ar_2$ may be each independently a substituted or unsubstituted C6-C60 aryl group, a substituted or unsubstituted C2-C60 heteroaryl group, or a substituted or unsubstituted C6-C60 condensed polycyclic group, wherein at least one of $Ar_1$ and $Ar_2$ is a C6-C60 aryl group that is substituted with an electron-attracting moiety, and n is an integer from 0 to 10.

The compound of Formula 1 may serve as an electron injecting material or an electron transporting material for organic light-emitting devices. This is caused by the fact that the substituent, $Ar_1$ or $Ar_2$, of the compound of Formula 1 is substituted with an electron-attracting moiety. The electron-attracting moiety will be described later in the specification.

Due to the inclusion of the heterocyclic ring, the compound of Formula 1 has a high glass transition temperature (Tg) or a high melting point. Thus, the heterocyclic compound has high heat resistance against Joule's heat generated in an organic layer, between organic layers, or between an organic layer and a metal electrode when light emission occurs, and has high durability in high-temperature environments. An organic light-emitting device manufactured using the heterocyclic compound of Formula 1 may have improved durability when stored or operated.

Substituents in the compound of Formula 1 will now be described in more detail.

In some embodiments, the electron-attracting moiety denotes a moiety including an element with a large electronegativity, for example, an electron-attracting group.

Examples of the electron-attracting moiety may be F; —CN; a C1-C60 alkyl group substituted with at least one —F; a C2-C60 heteroaryl group; a C2-C60 heteroaryl group substituted with at least one selected from a deuterium atom, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid or a salt thereof, a C1-C60 alkyl group, a C1-C60 alkoxy group, a C2-C60 alkenyl group, a C2-C60 alkynyl group, a C6-C60 aryl group, and a C2-C60 heteroaryl group; and a C6-C60 aryl group.

In some embodiments, R in Formula 1 may be one of the groups represented by Formulae 2a to 2d below.

In Formulae 2a to 2d, $Z_1$ may be a hydrogen atom, a deuterium atom, a halogen atom, —CN, a substituted or unsubstituted C1-C20 alkyl group, a substituted or unsubstituted C6-C20 aryl group, or a substituted or unsubstituted C2-C20 heteroaryl group;

$Y_1$ is —CH= or —N=;

p is an integer from 1 to 9; and

* indicates a binding site.

In some other embodiments, X in Formula 1 may be one of the groups represented by Formulae 3a to 3d below.

In Formulae 3a to 3d, $Y_1$ and $Y_2$ may be each independently —CH= or —N=;

$Q_1$ may be a linking group represented by —C($R_{30}$)($R_{31}$)—, —S—, or —O—;

$R_{30}$ and $R_{31}$ may be each independently a hydrogen atom, a deuterium atom, a substituted or unsubstituted C1-C20 alkyl group, a substituted or unsubstituted C6-C20 aryl group, or a substituted or unsubstituted C6-C20 condensed polycyclic group; and \* indicates a binding site.

In some other embodiments, in Formula 1, $Ar_1$ and $Ar_2$ may be each independently one of the groups represented by Formulae 4a to 4d below.

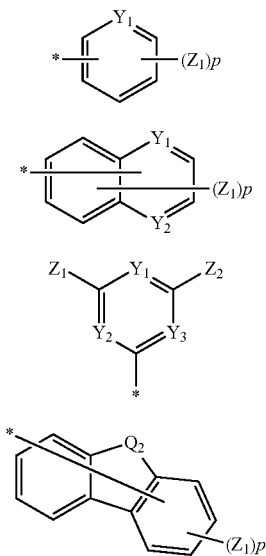

In Formulae 4a to 4d, $Y_1$ to $Y_3$ may be each independently —CH= or —N=;

$Q_2$ may be a linking group represented by —C($R_{30}$)($R_{31}$)—, —S—, or —O—;

$Z_1$, $Z_2$, $R_{30}$ and $R_{31}$ may be each independently a hydrogen atom; a deuterium atom; —F; —CN; a C1-C60 alkyl group substituted with at least one —F; a C2-C60 heteroaryl group; a substituted or unsubstituted C6-C20 aryl group; or a C2-C60 heteroaryl group substituted with at least one selected from a deuterium atom, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid or a salt thereof, a C1-C60 alkyl group, a C1-C60 alkoxy group, a C2-C60 alkenyl group, a C2-C60 alkynyl group, a C6-C60 aryl group, and a C2-C60 heteroaryl group;

p is an integer from 1 to 7; and

\* indicates a binding site.

Hereinafter, substituents described with reference to the formulae will now be described in more detail. In this regard, the number of carbons in substituents is presented only for illustrative purposes and do not limit the characteristics of the substituents. Also, substituents that are not particularly defined in the specification follow general definitions of the substituents.

The unsubstituted C1-C60 alkyl group may be linear or branched. Non-limiting examples of the unsubstituted C1-C60 alkyl group may be methyl, ethyl, propyl, isobutyl, sec-butyl, pentyl, iso-amyl, hexyl, heptyl, octyl, nonanyl, and dodecyl. At least one hydrogen atom of the unsubstituted C1-C60 alkyl group may be substituted with a deuterium atom, a halogen group, a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a C1-C10 alkyl group, a C1-C10 alkoxy group, a C2-C10 alkenyl group, a C2-C10 alkynyl group, a C6-C16 aryl group, or a C4-C16 heteroaryl group.

The unsubstituted C2-C60 alkenyl group indicates an unsaturated alkyl group having at least one carbon-carbon double bond in the center or at a terminal of the unsubstituted alkyl group. Examples of the unsubstituted C2-C60 alkenyl group are an ethenyl group, a propenyl group, a butenyl group, and the like. At least one hydrogen atom in the unsubstituted C2-C60 alkenyl group may be substituted with a substituent described above in conjunction with the substituted alkyl group.

The unsubstituted C2-C60 alkynyl group indicates an alkyl group having at least one carbon-carbon triple bond in the center or at a terminal of the alkyl group.

Non-limiting examples of the unsubstituted alkynyl group are acetylene, propylene, phenylacetylene, naphthylacetylene, isopropylacetylene, t-butylacetylene, and diphenylacetylene. At least one hydrogen atom of the alkynyl group may be substituted with a substituent such as those described above in conjunction with the substituted alkyl group.

The unsubstituted C3-C60 cycloalkyl group indicates a C3-C60 cyclic alkyl group wherein at least one hydrogen atom in the cycloalkyl group may be substituted with a substituent described above in conjunction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the substituted alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the substituted or unsubstituted C6-C60 aryl group are a phenyl group, a C1-C10 alkylphenyl group (for example, ethylphenyl group), a biphenyl group, a C1-C10 alkyl biphenyl group, a C1-C10 alkoxybiphenyl group, an o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, methylnaphthyl group), a C1-C10 alkoxynaphthyl group (for example, methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C2-C60 heteroaryl group used herein includes one, two, three, or four hetero atoms selected from N, O, P, and S. At least two rings may be fused to each other or linked to each other by a single bond. Non-limiting examples of the unsubstituted C2-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the C2-C60 heteroaryl group may be substituted with a substituent described above in conjunction with the unsubstituted C1-C60 alkyl group.

The unsubstituted C6-C60 aryloxy group is a group represented by —OA$_1$ wherein A$_1$ may be a C6-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C6-C60 arylthio group is a group represented by —SA$_1$ wherein A$_1$ may be a C6-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group is distinct from an aryl group or a heteroaryl group in terms of being non-aromatic.

Non-limiting examples of the compound represented by Formula 1 are compounds represented by the following formulae:

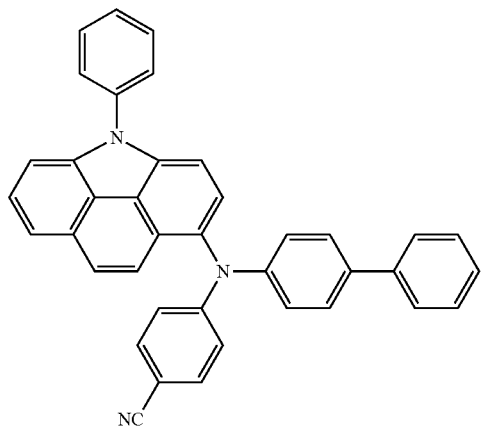

1

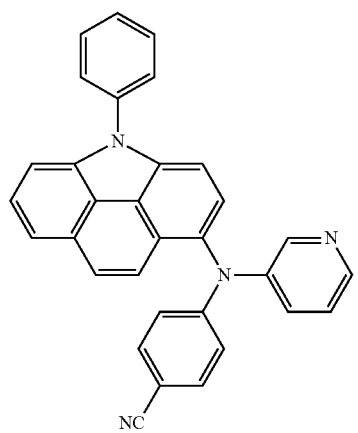

2

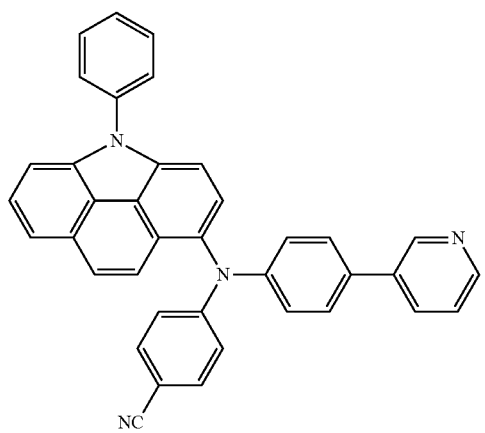

3

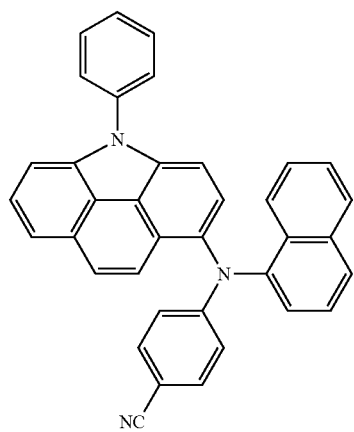

4

5

6
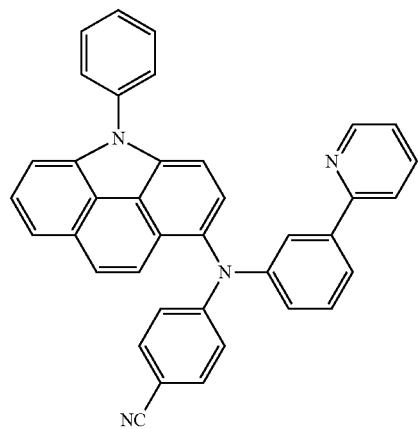
7
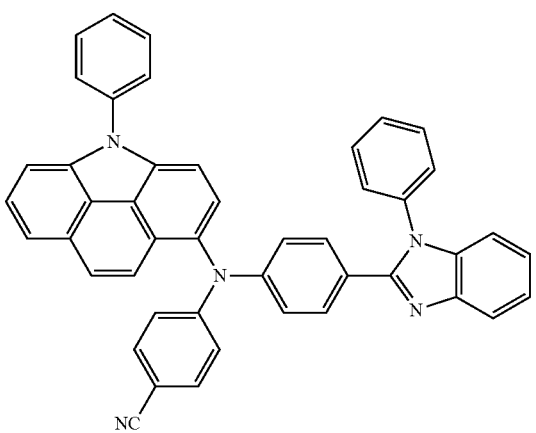
8
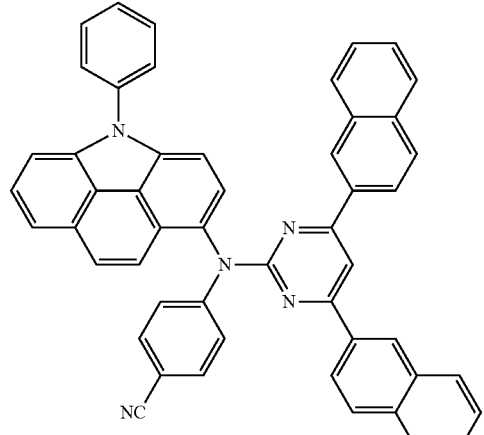
9
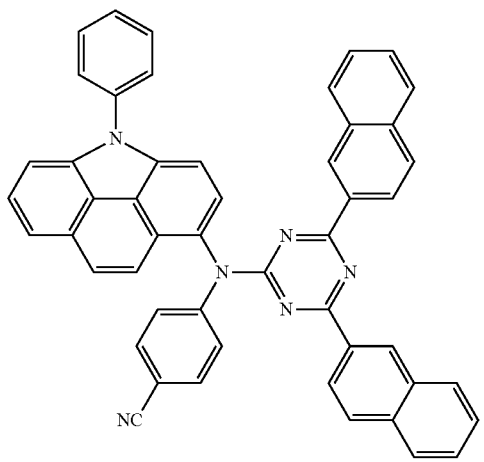
10
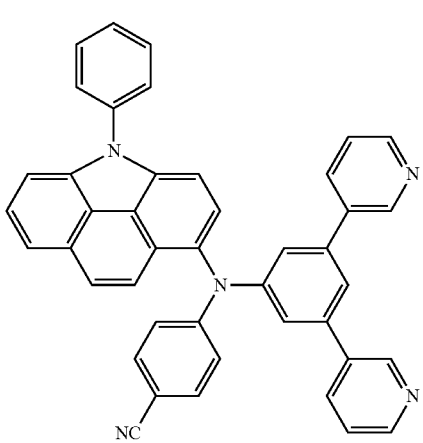
11
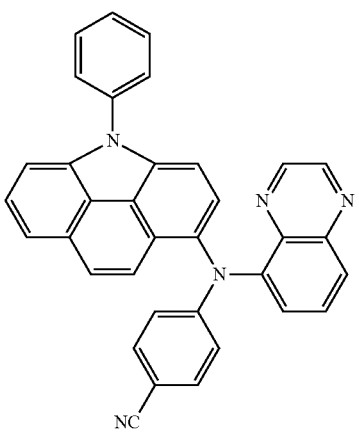

12
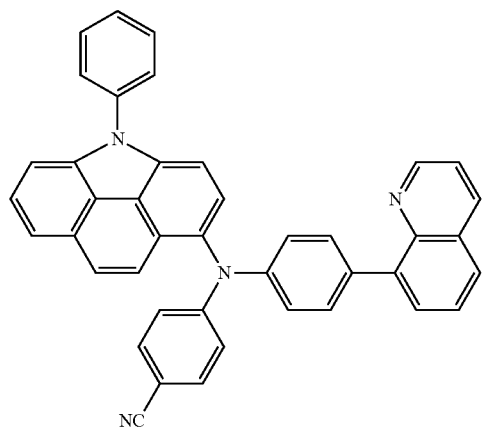
13
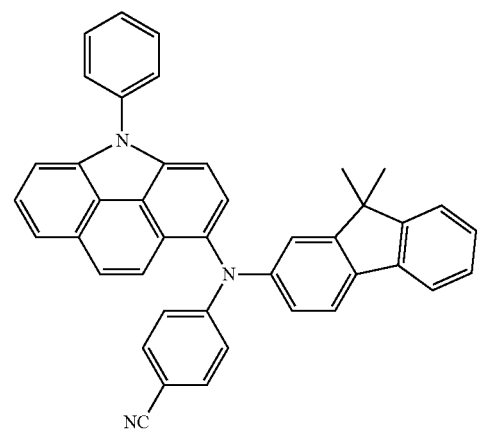
14
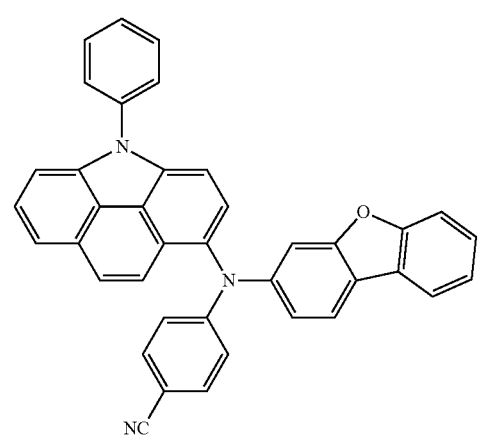
15
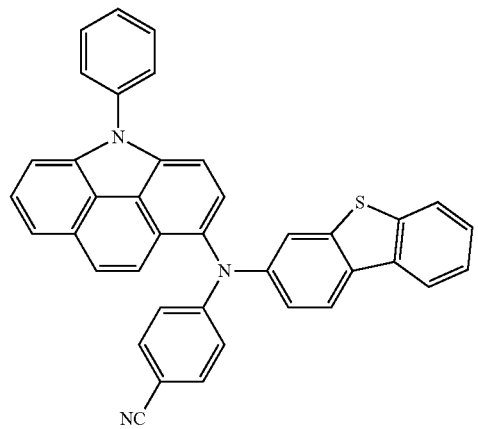
16
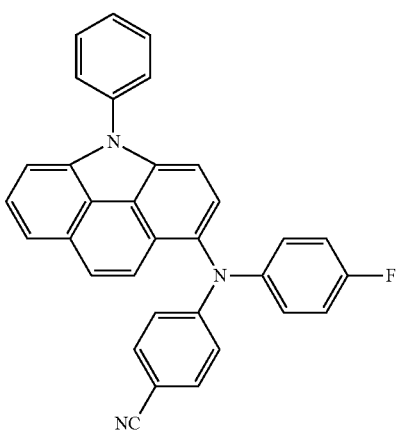
17
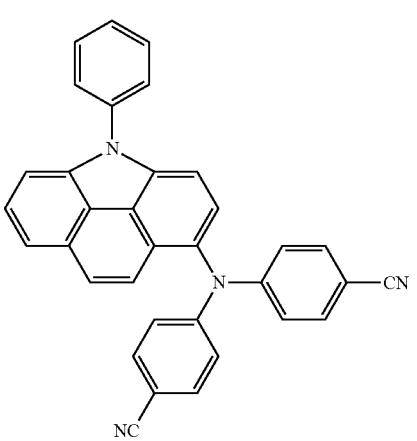

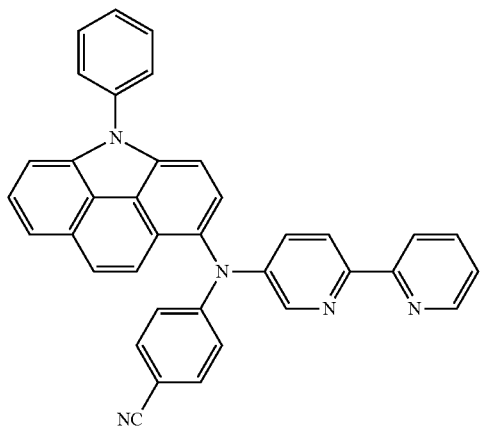
18
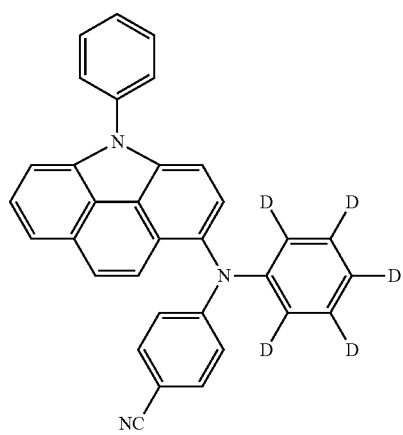
19
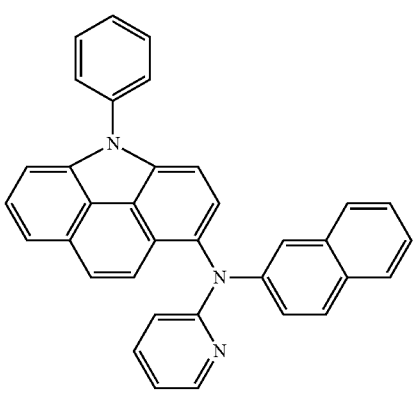
20
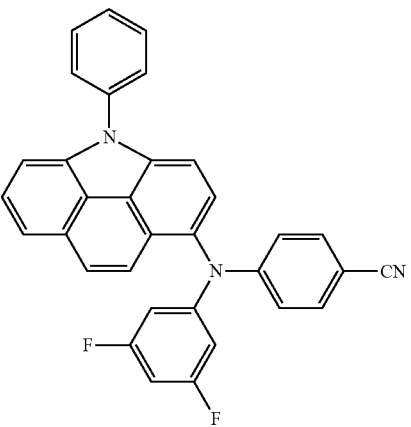
21
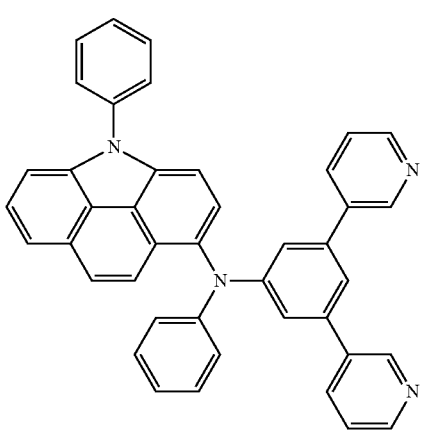
22
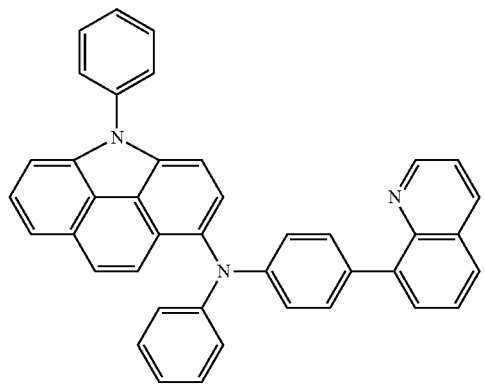
23
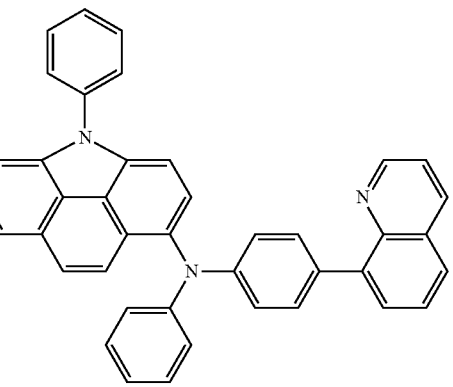
24

25
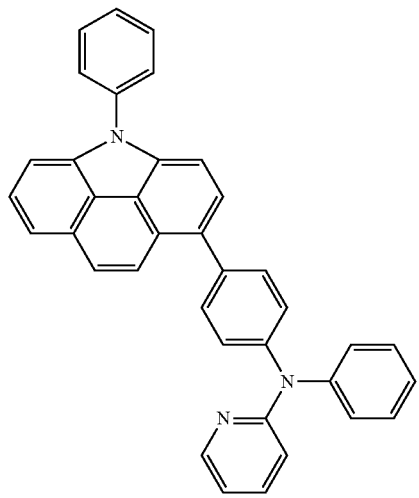
26
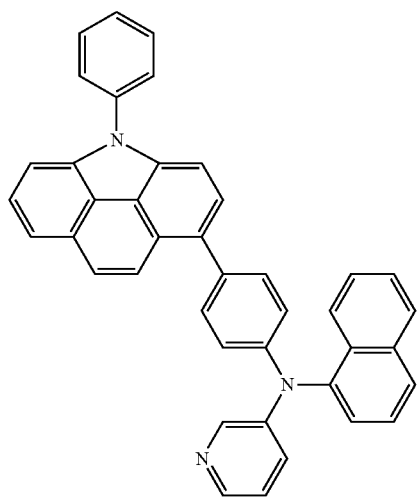
27
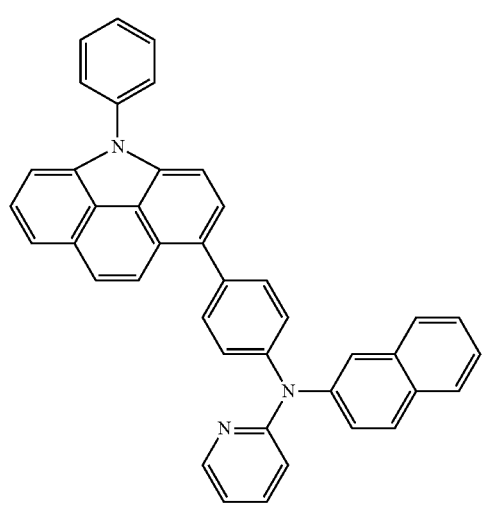
28
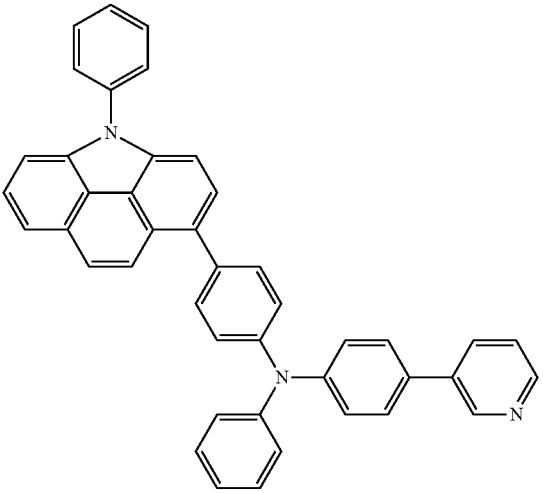
29
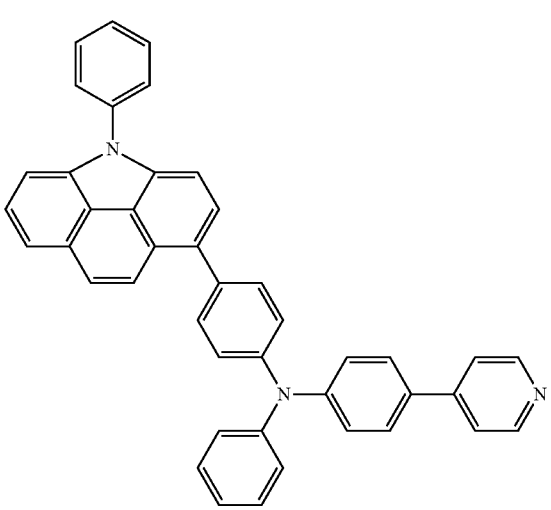
30
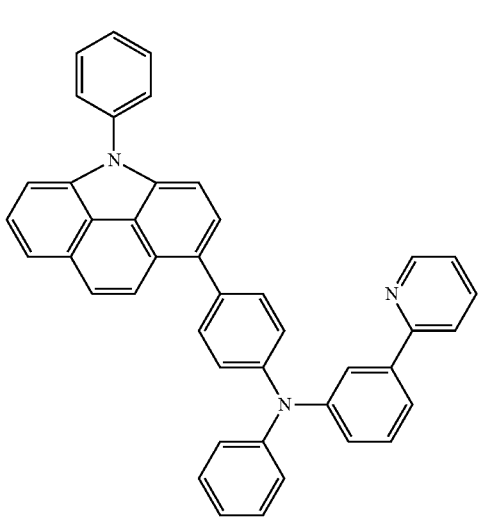

31
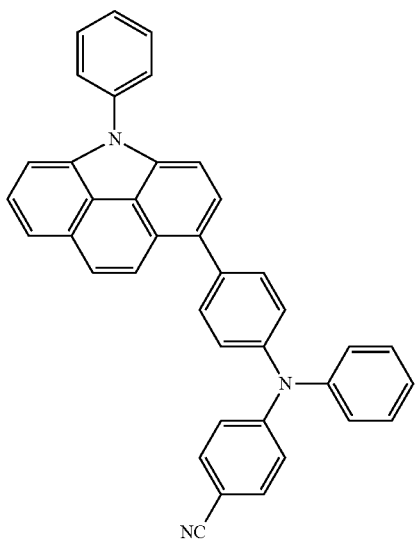
32
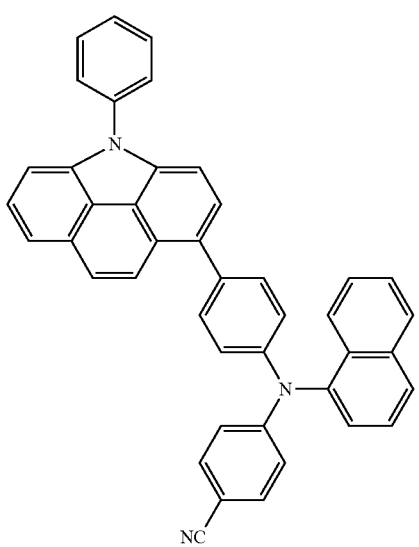
33
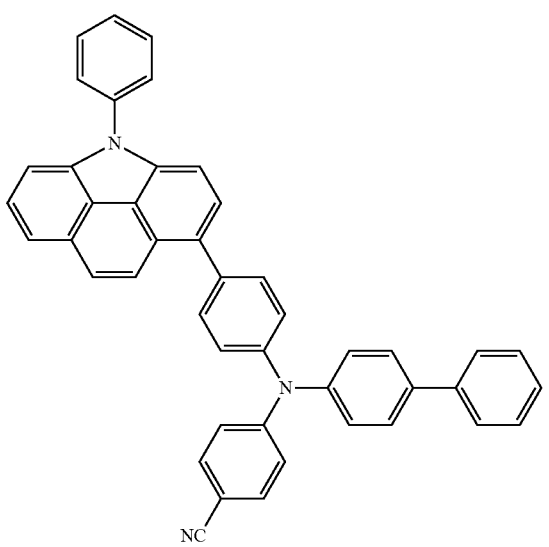
34
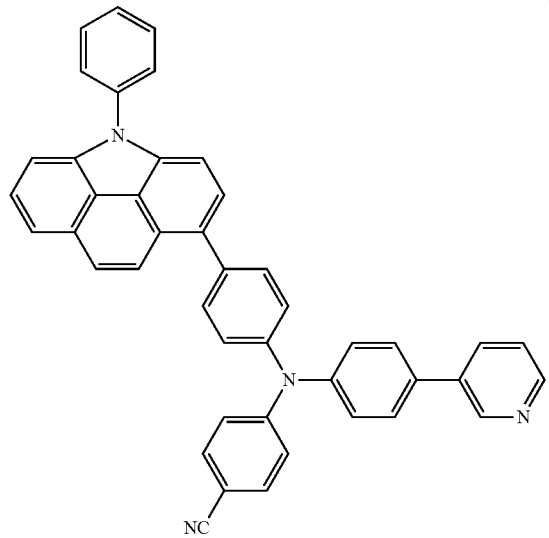
35
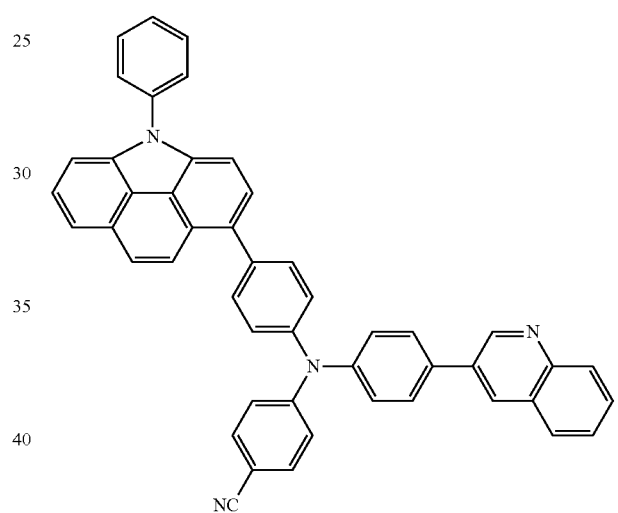
36
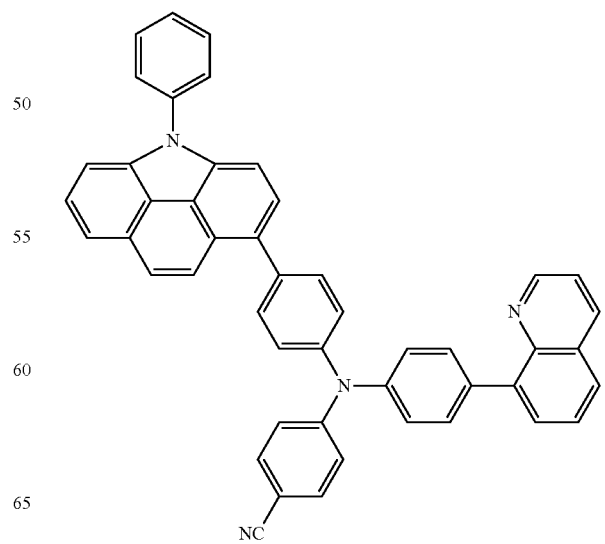

37
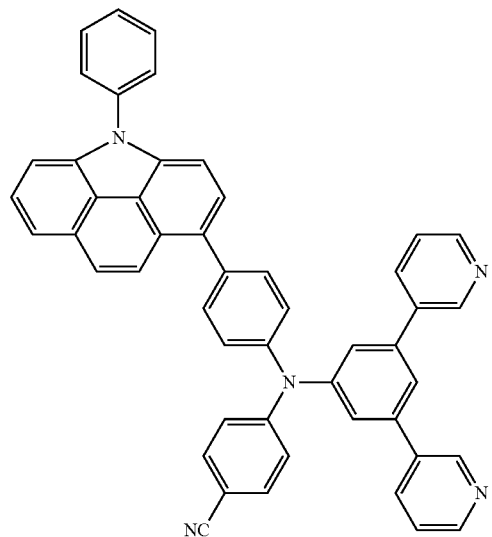
38
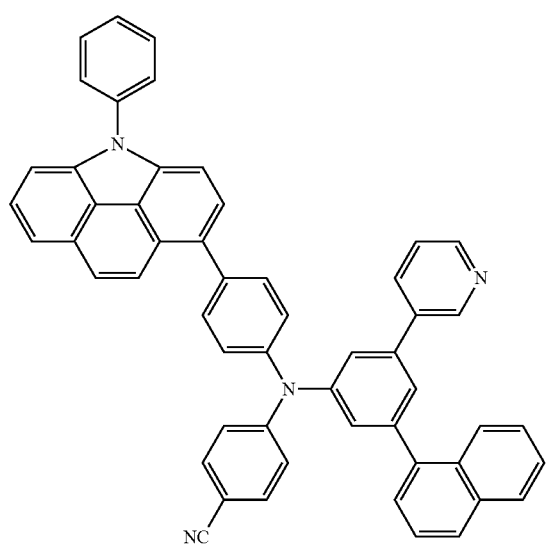
39
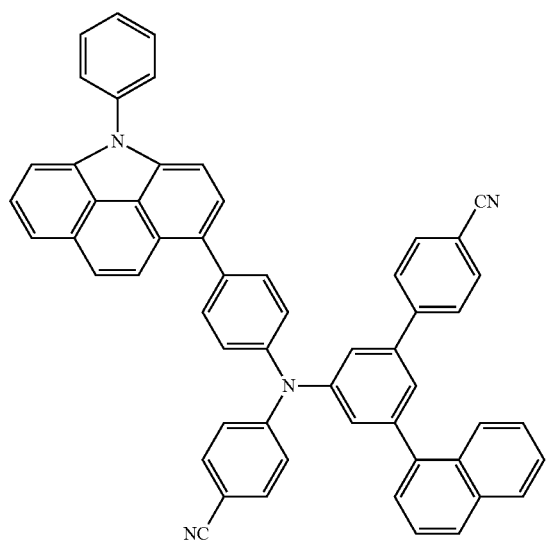
40
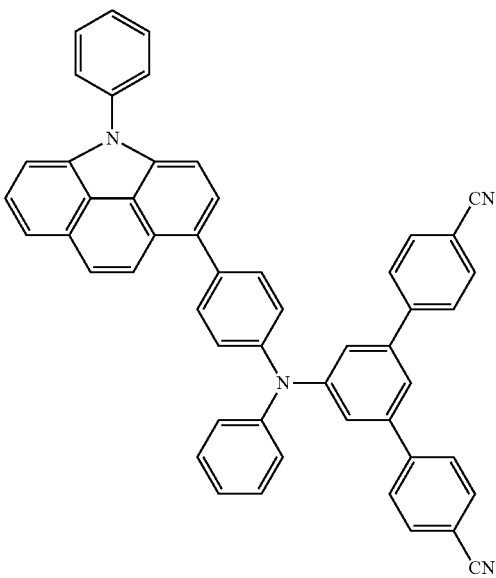
41
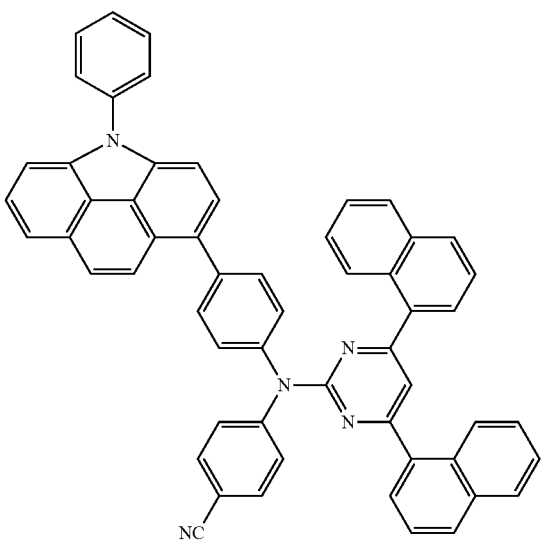

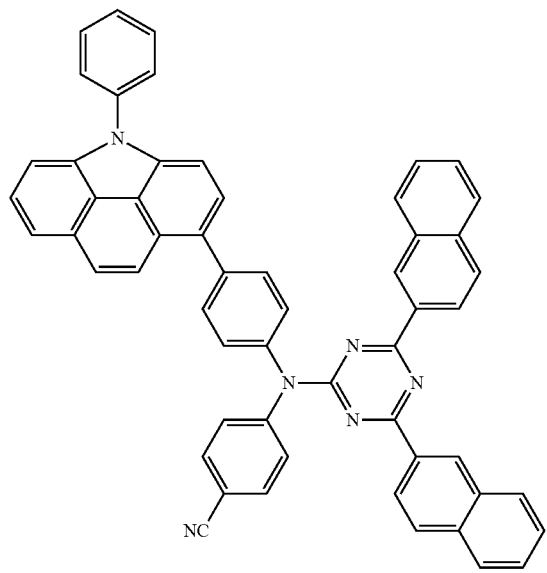
42
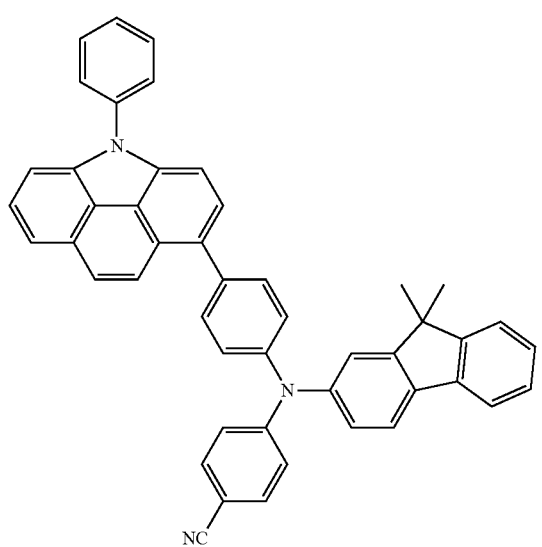
43
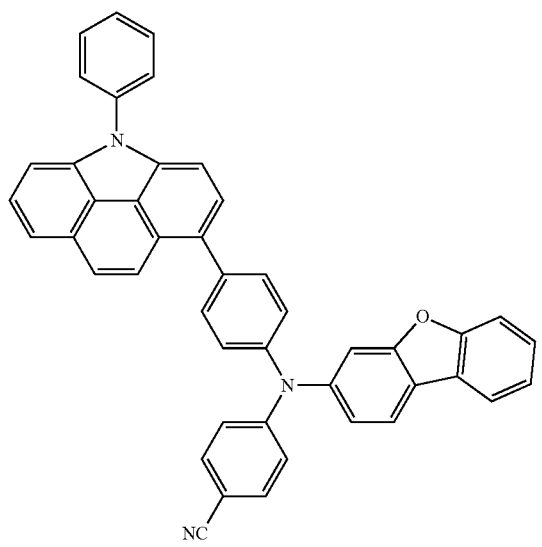
44
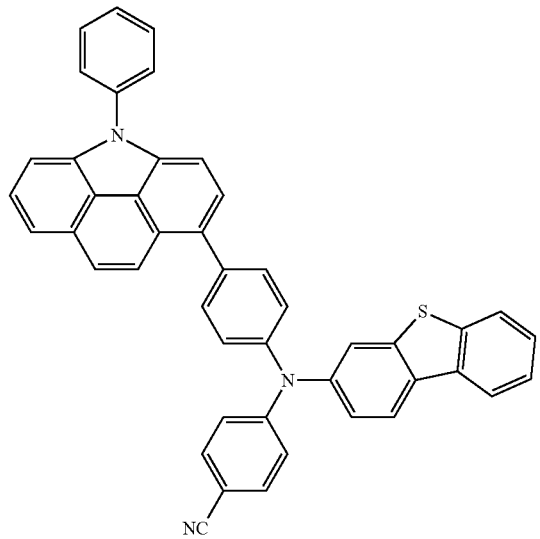
45
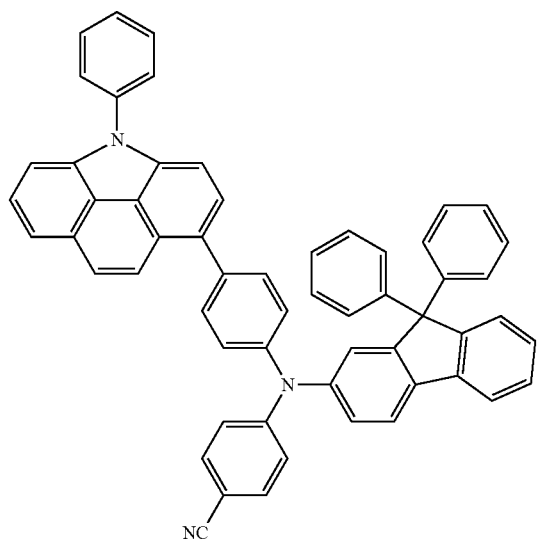
46
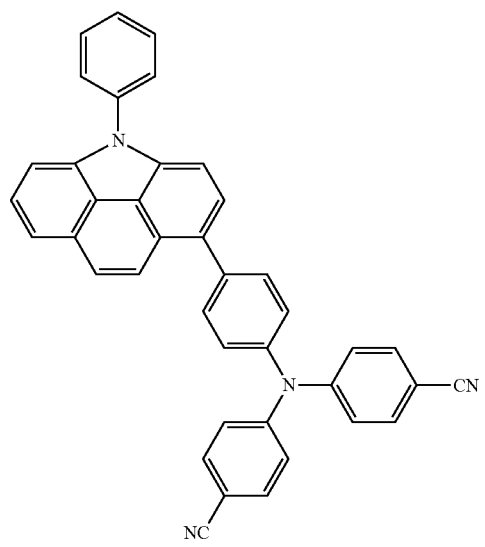
47

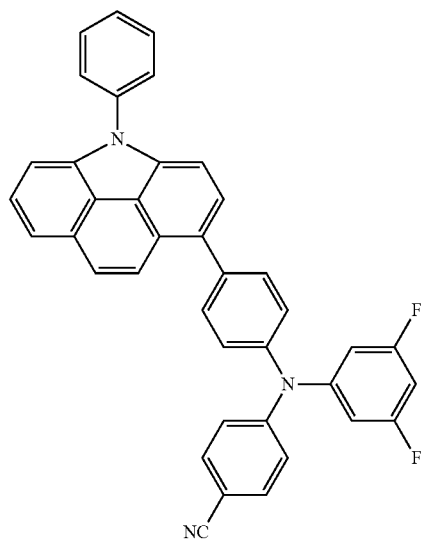
48
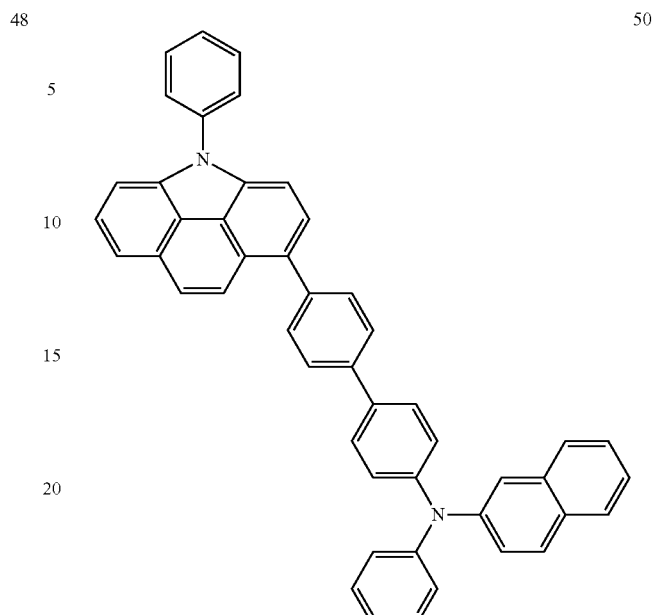
50
49
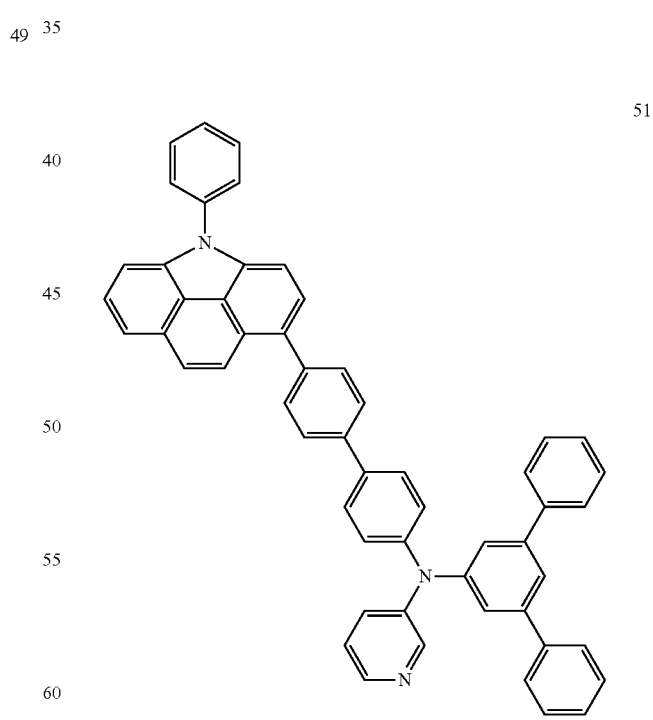
51

52
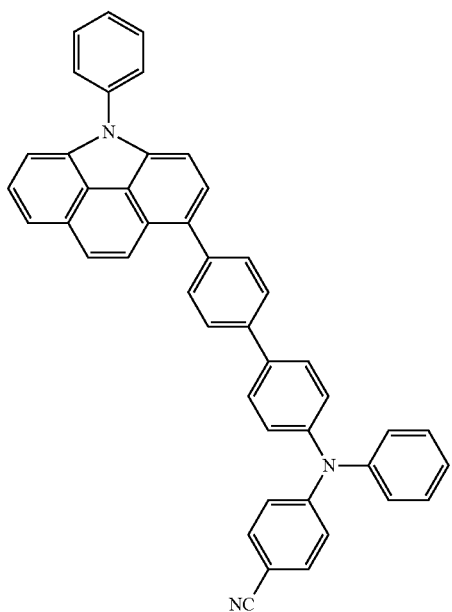
53
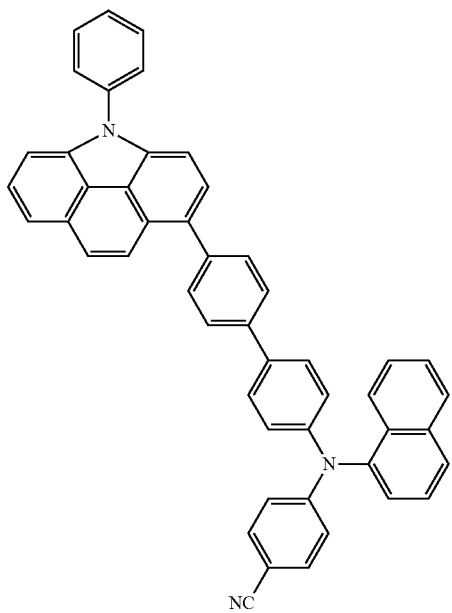
54
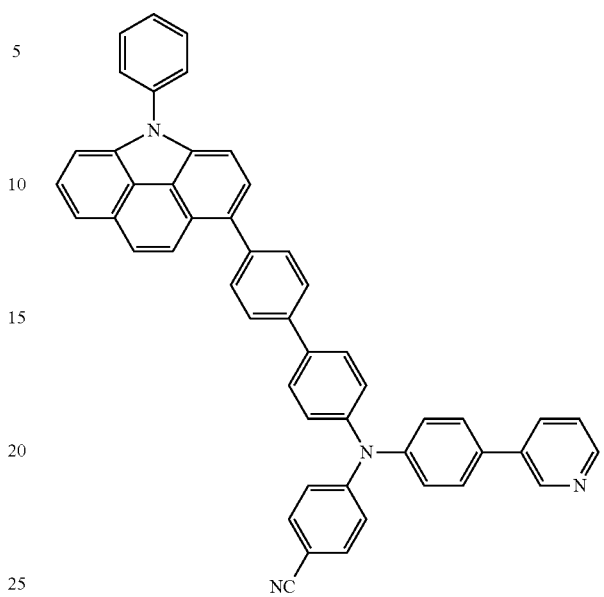
55
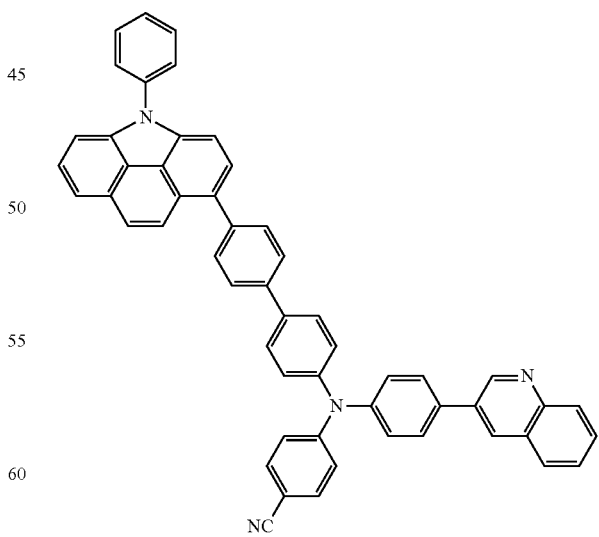

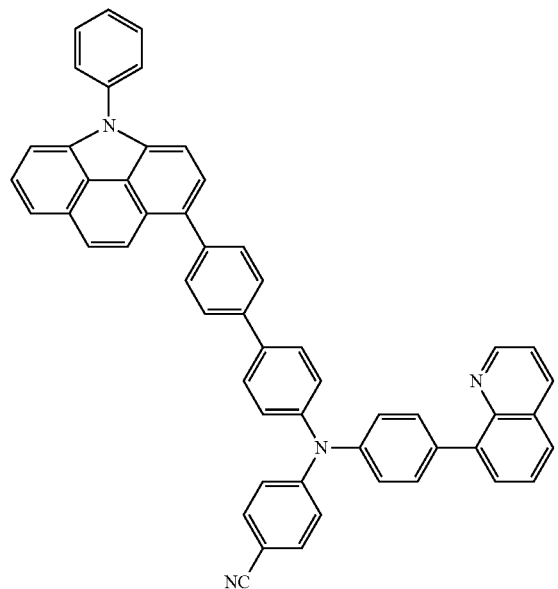
56
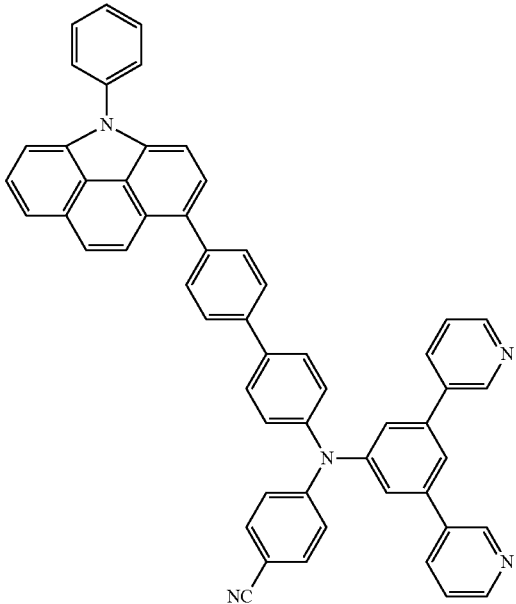
58
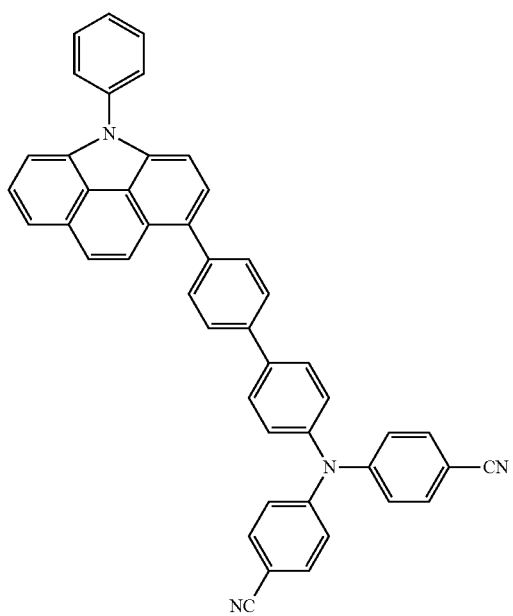
57
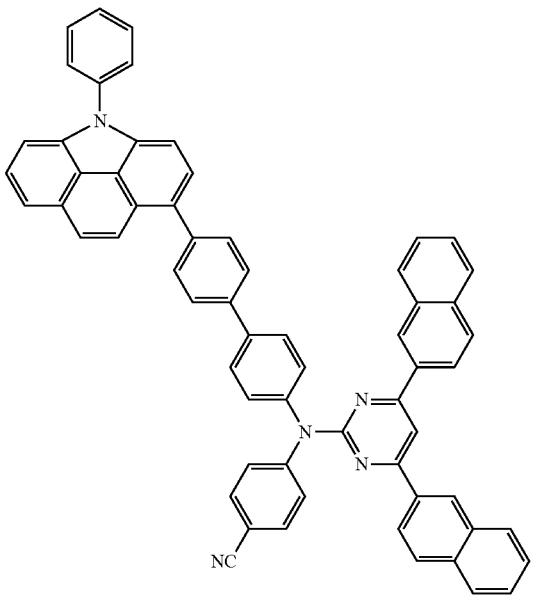
59

60
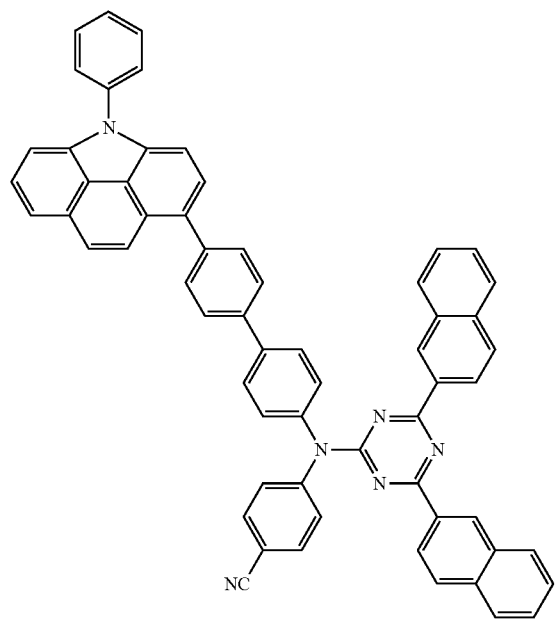
61
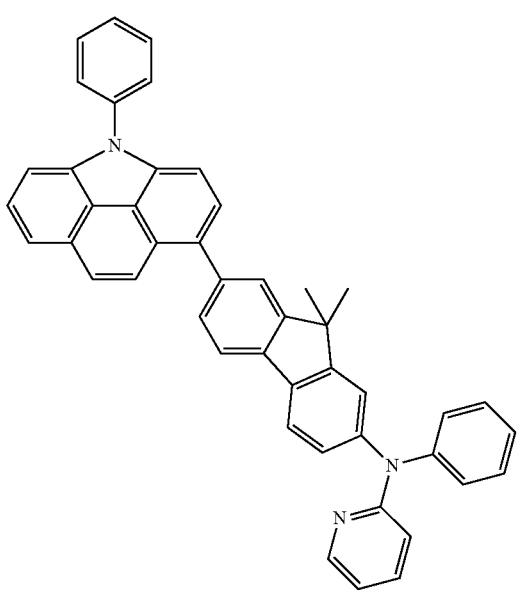
62
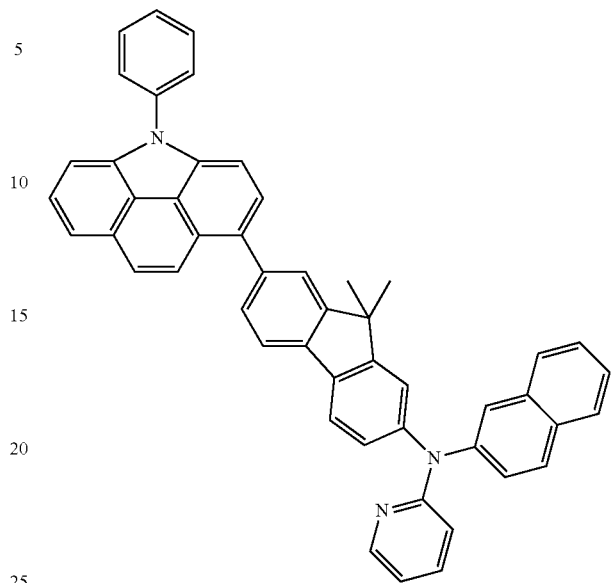
63
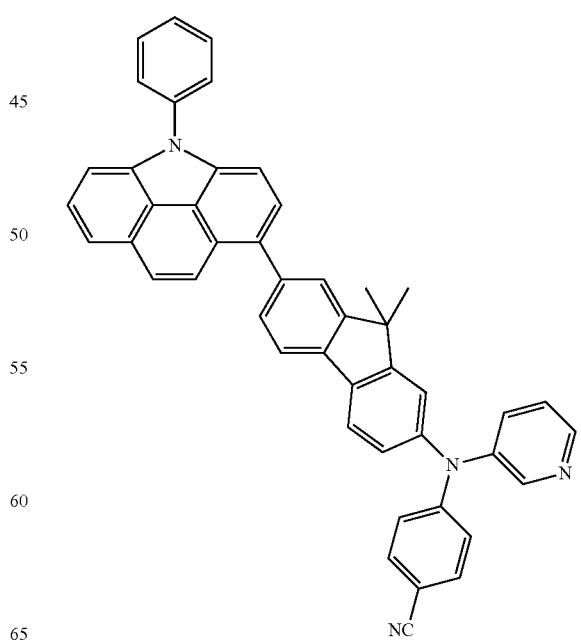

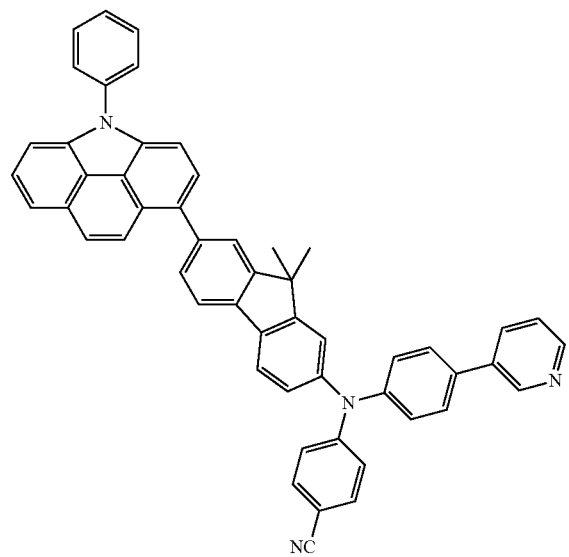
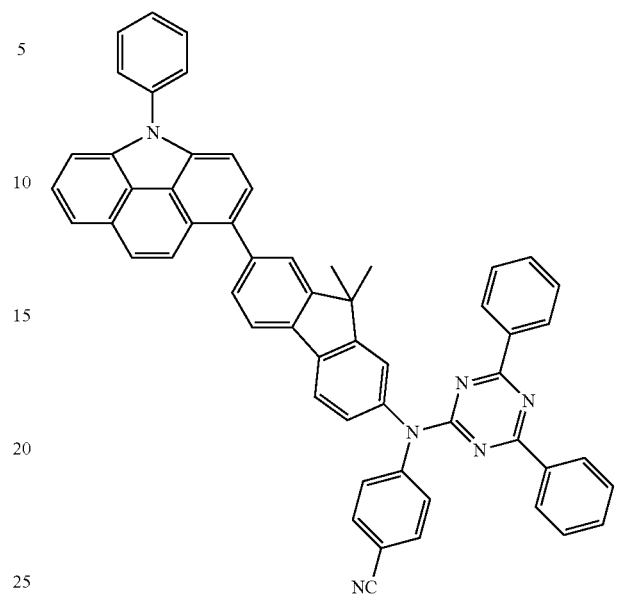
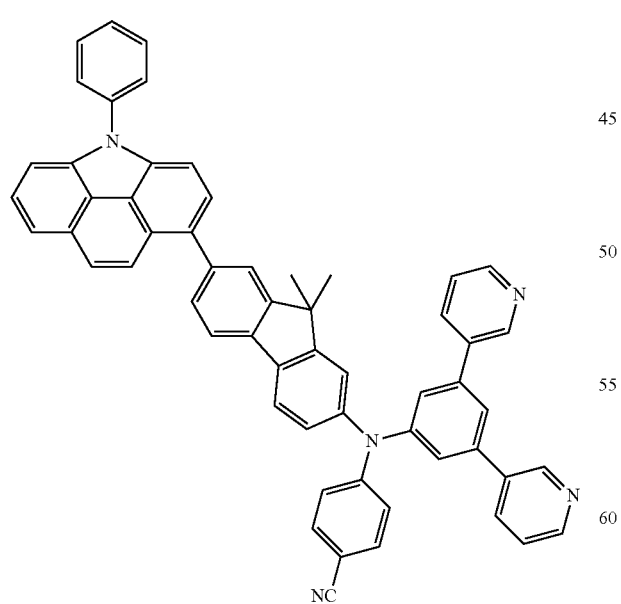
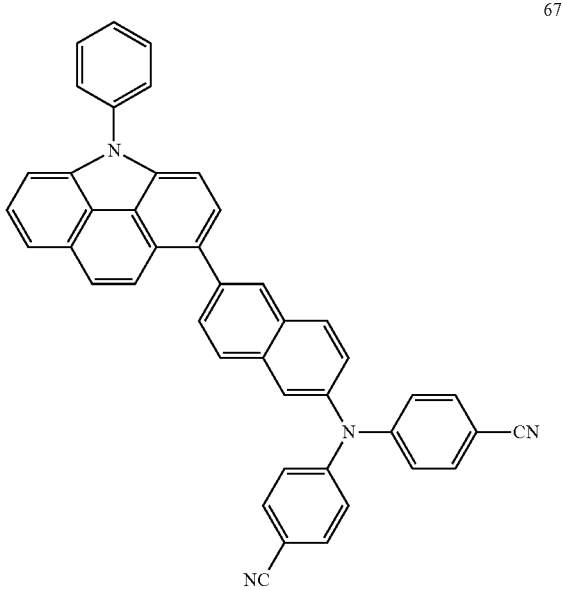

33
-continued
68
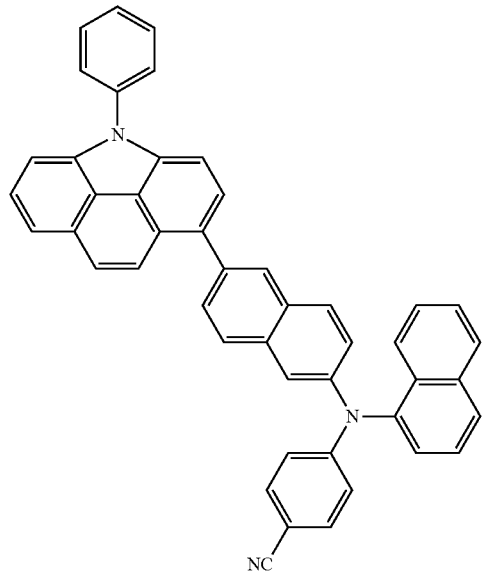
69
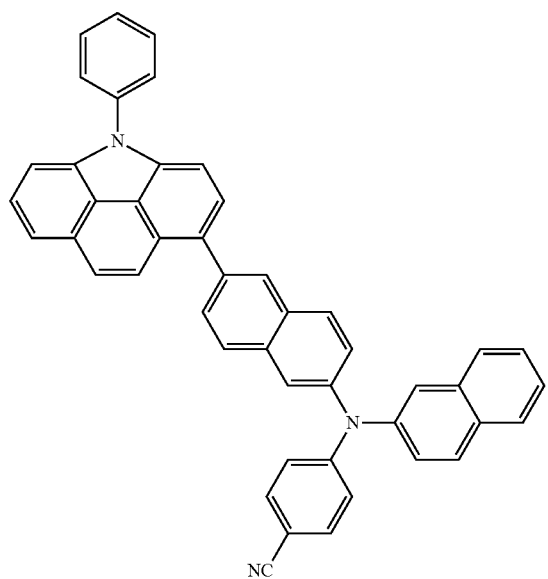
70
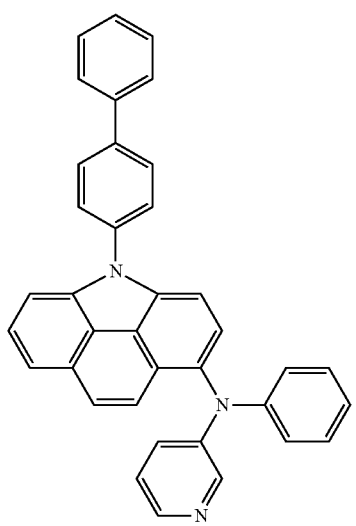
34
-continued
71
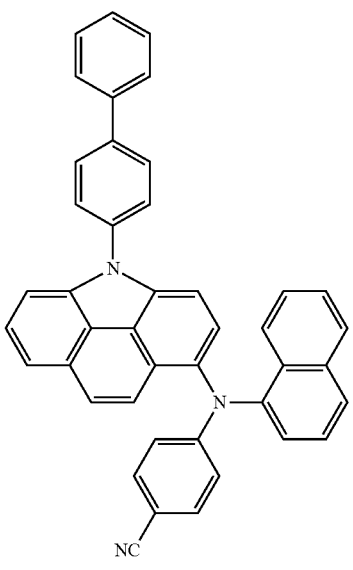
72
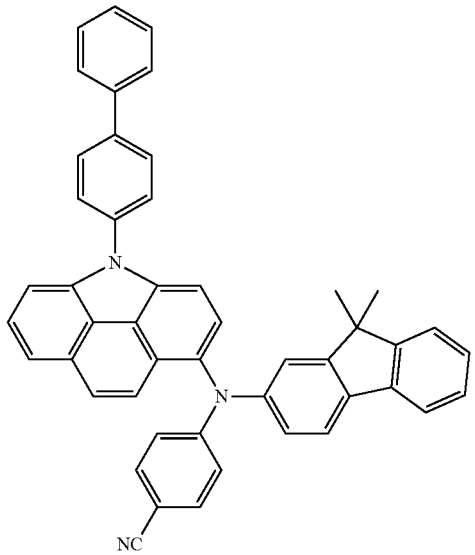
73
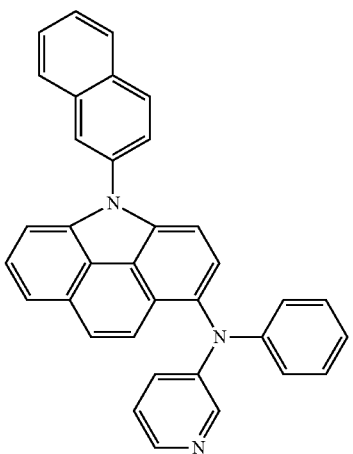

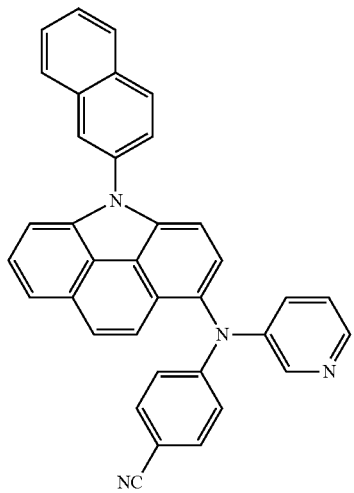
74
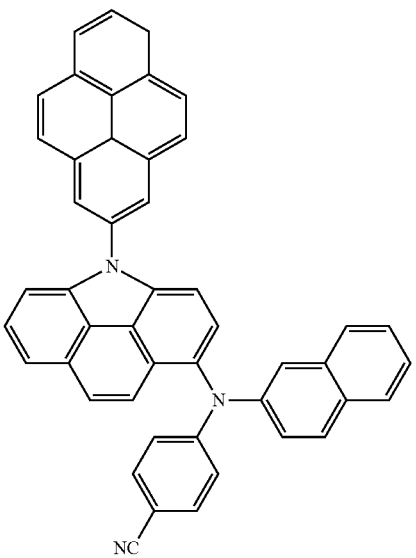
77
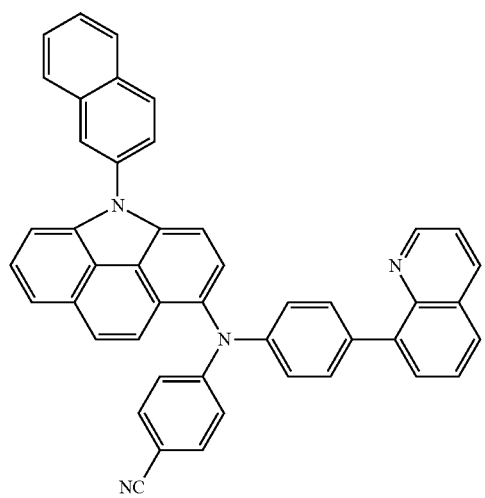
75
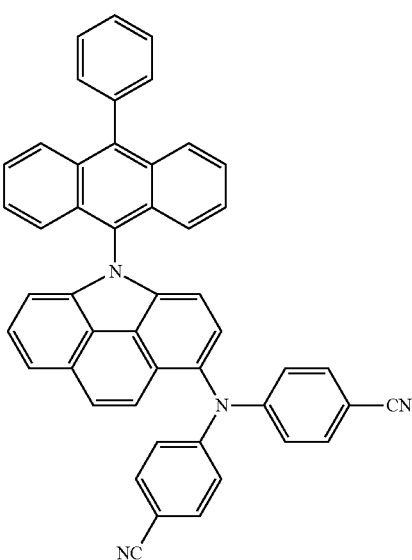
78
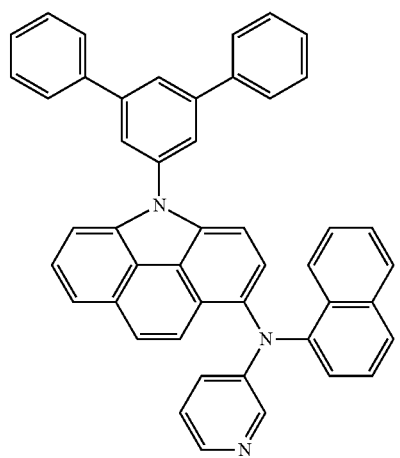
76
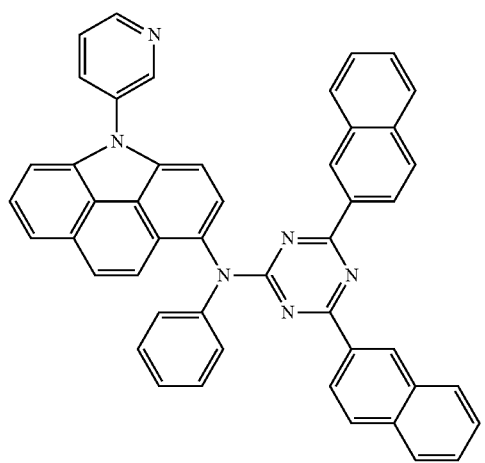
79

80
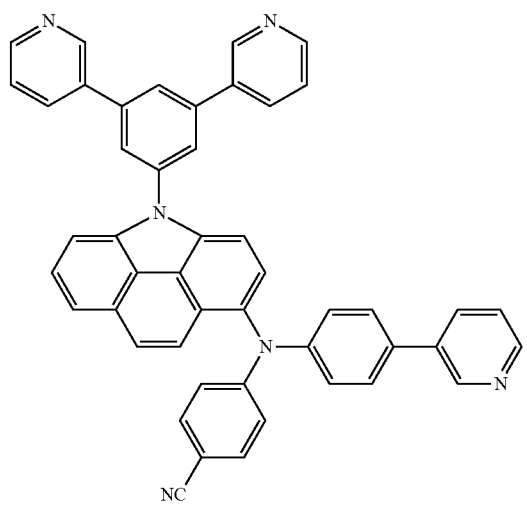
81
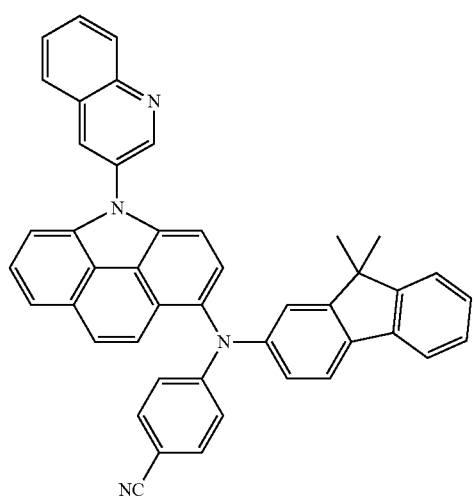
82
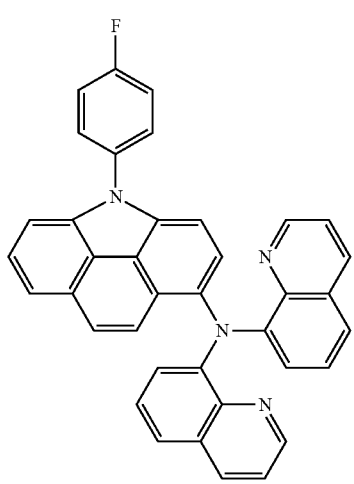
83
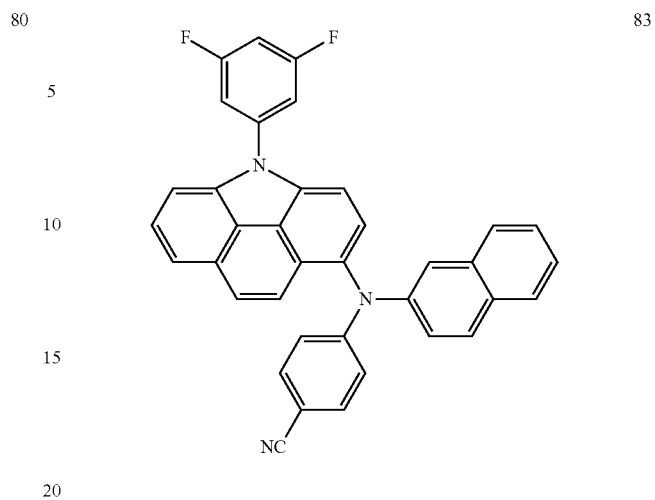
84
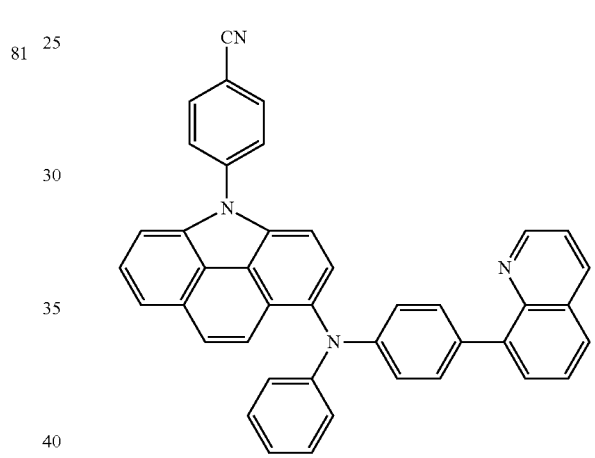
85
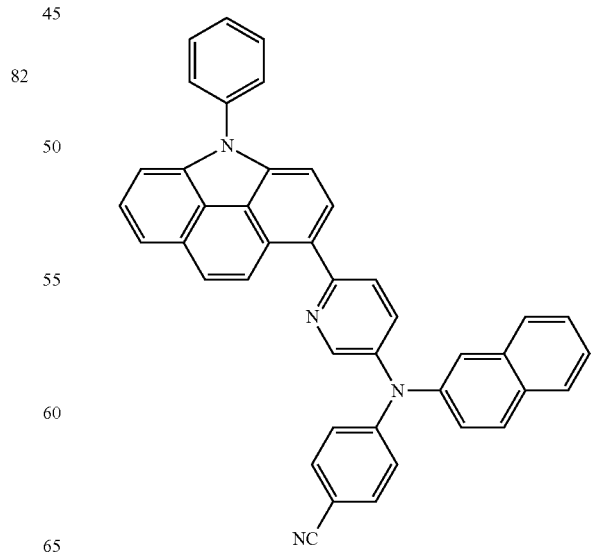

86
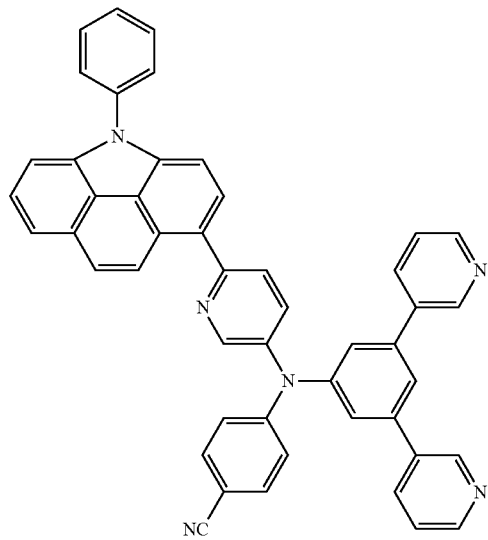
87
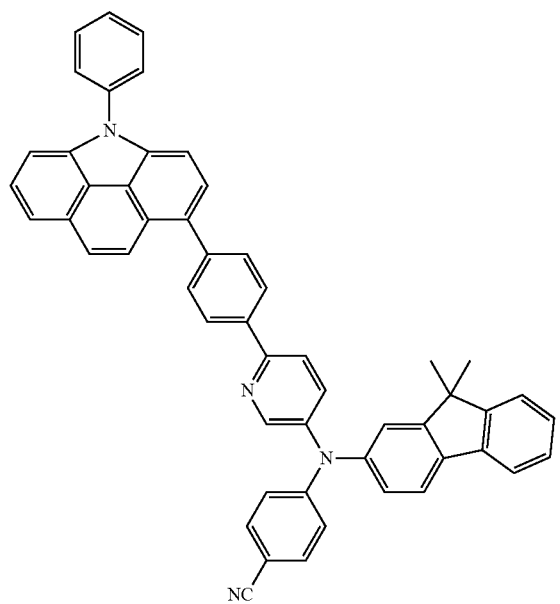
88
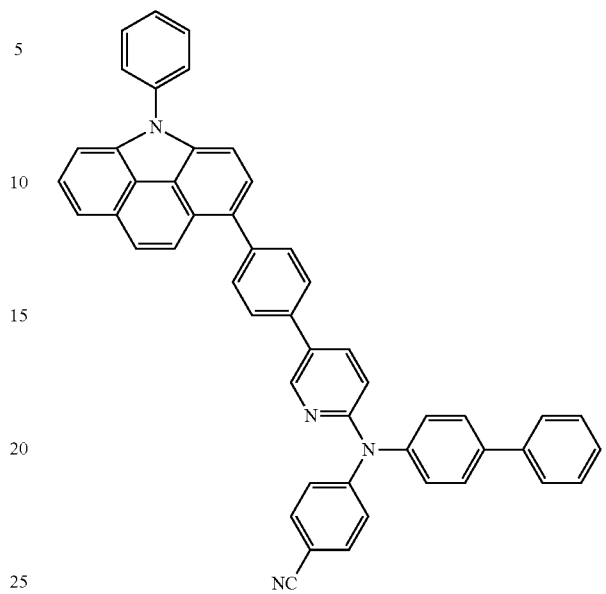
89
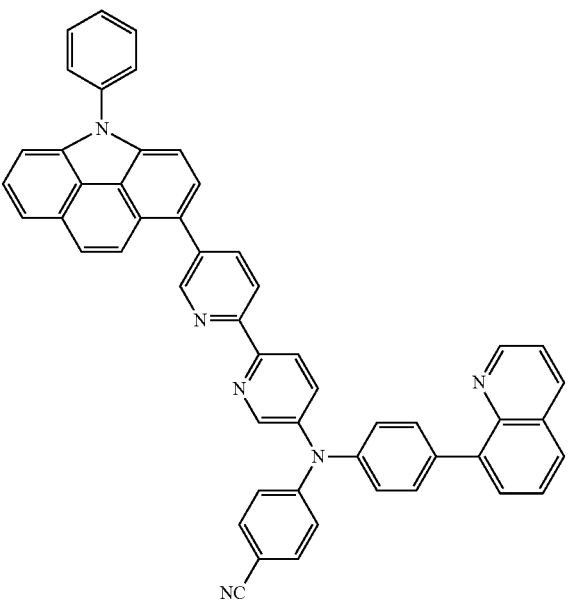

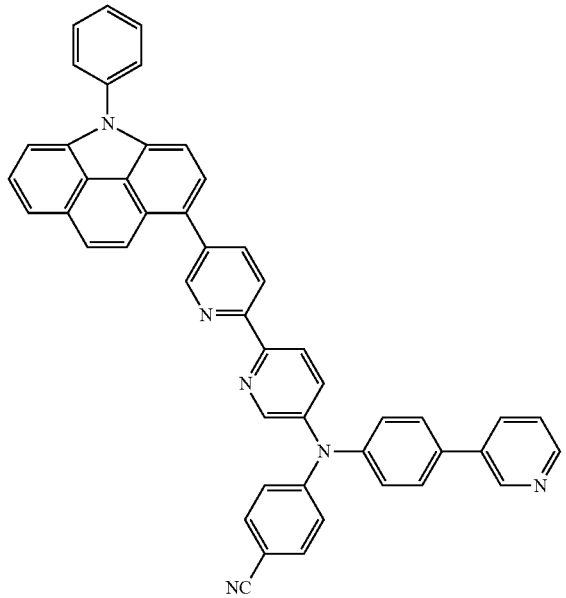

90

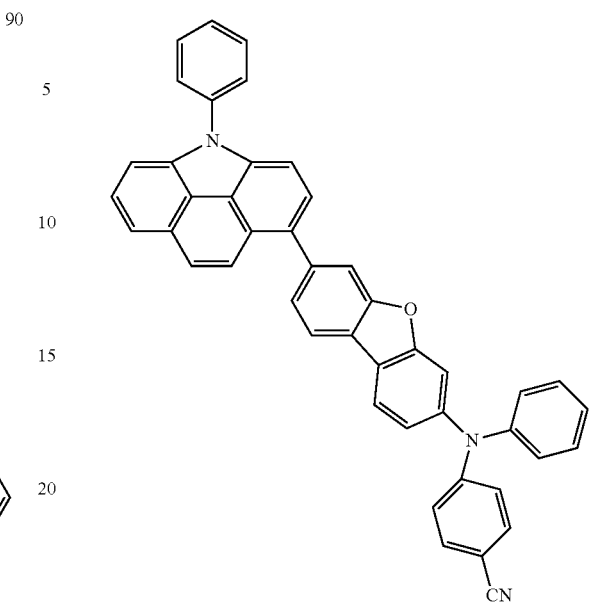

92

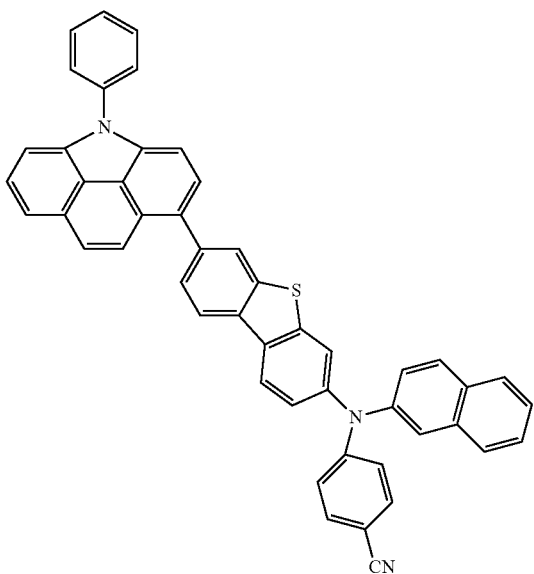

91

Another embodiment of the present invention provides an organic light-emitting device including a first electrode, a second electrode, and an organic layer disposed between the first electrode and the second electrode, wherein the organic layer includes the compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer (EML), a hole blocking layer, an electron transport layer, an electron injection layer, and a functional layer having both electron injection and electron transport capabilities (hereinafter, "E-functional layer").

In particular, the organic layer may be used as an electron injection layer, an electron transport layer, or a functional layer having both electron injection and transport capabilities.

In some embodiments, the organic light-emitting device may include an electron injection layer, an electron transport layer, an EML, a hole injection layer, a hole transport layer, or a functional layer having both hole injection and transport capabilities; the electron injection layer, the electron transport layer, or the functional layer having both electron injection and transport capabilities may include the compound of Formula 1 above; and the EML may include an anthracene-based compound, an arylamine-based compound, or a styryl-based compound.

In some other embodiments, the organic light-emitting device may include an electron injection layer, an electron transport layer, an EML, a hole injection layer, a hole transport layer, or a functional layer having both hole injection and transport capabilities; at least one of a red EML, a green EML, a blue EML, and a white EML of the EML may include a phosphorescent compound; and at least one of the electron injection layer, the electron transport layer, and the functional layer having both electron injection and hole transport capabilities may further include a charge-generating material, in addition to the compound of the present invention. In some embodiments, the charge-generating material may be a p-dopant, and the p-dopant may be a quinine derivative, a metal oxide, or a cyano group-containing compound.

In some embodiments, the organic layer may include an electron transport layer, and the electron transport layer may include an electron-transporting organic compound and a metal complex. The metal complex may be a lithium (Li) complex.

The term "organic layer" as used herein refers to a single layer and/or a plurality of layers disposed between the first and second electrodes of the organic light-emitting device.

The drawing is a schematic sectional view of an organic light-emitting device according to an embodiment of the present invention. Hereinafter, a structure of an organic light-emitting device according to an embodiment of the present invention and a method of manufacturing the same will now be described with reference to the drawing.

A substrate may be any substrate that is used in existing organic light-emitting devices. In some embodiments, the substrate may be a glass substrate or a transparent plastic substrate with strong mechanical strength, thermal stability, transparency, surface smoothness, ease of handling, and water resistance.

A first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer may be disposed on the first electrode.

The organic layer may include a hole injection layer (HIL), a hole transport layer (HTL), a buffer layer, an EML, an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the material that is used to form the HIL, and the desired structure and thermal properties of the HIL to be formed. For example, the coating rate may be in a range of about 2000 rpm to about 5000 rpm, and a temperature at which heat treatment is performed to remove a solvent after coating may be in a range of about 80° C. to about 200° C. However, the coating conditions are not limited thereto.

The HIL may be formed of any suitable hole injecting material. Non-limiting examples of a known hole injecting material to form the HIL are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline-poly(4-styrenesulfonate) (PANI/PSS).

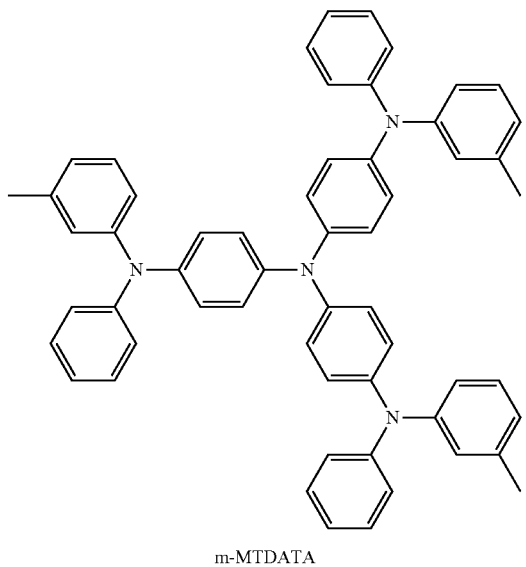

m-MTDATA

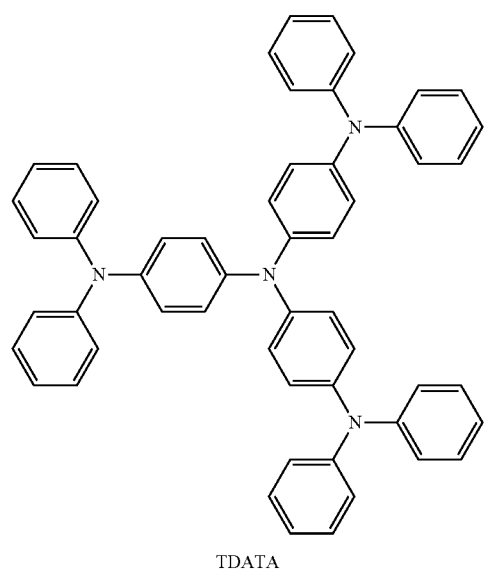

TDATA

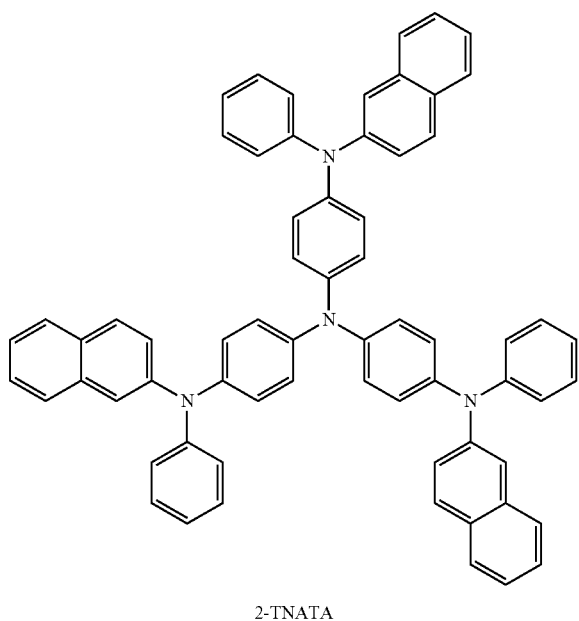

2-TNATA

The thickness of the HIL may be from about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, an HTL may be formed on the HIL by using vacuum deposition, spin coating, casting, LB deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of any known hole transporting material. Non-limiting examples of a known hole injecting material to form the HTL are carbazole derivatives, such as N-phenylcarbazole or polyvinylcarbazole, N,N$^1$-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

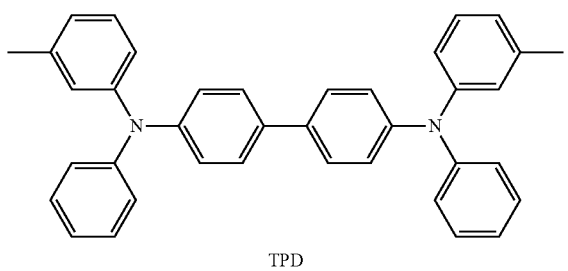

TPD

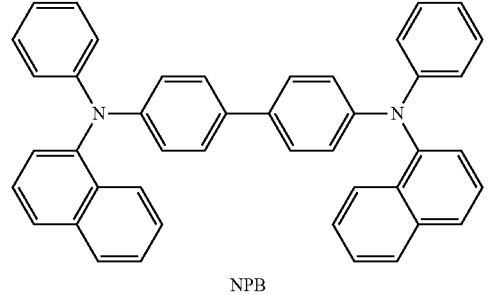

NPB

The thickness of the HTL may be from about 50 Å to about 2000 Å, and in some embodiments, from about 100 Å to about 1500 Å. When the thickness of the HTL is within these ranges, the HTL may have good hole transporting ability without a substantial increase in driving voltage.

An H-functional layer (having both hole injection and hole transport capabilities) may contain at least one material selected from hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 350 below:

<Formula 300>

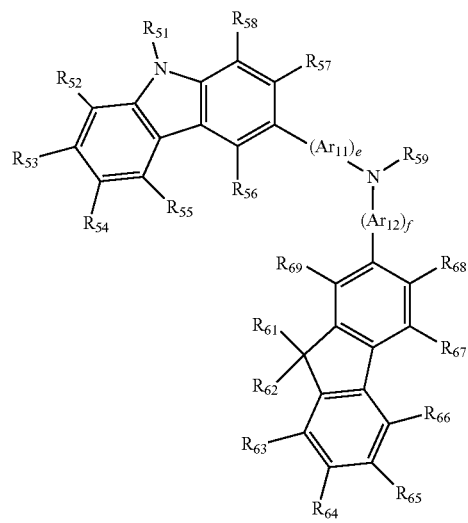

<Formula 350>

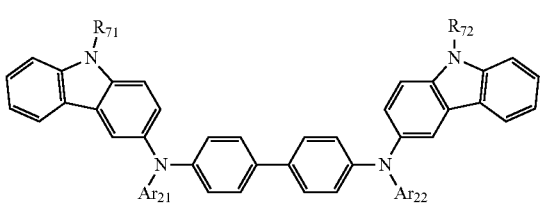

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. In a non-limiting embodiment, e may be 1, and f may be 0.

In Formulae 300 and 350 above, $R_{51}$ to $R_{58}$, $R_{61}$ to $R_{69}$, and $R_{71}$ to $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment, the compound of Formula 300 may be a compound represented by Formula 300A below:

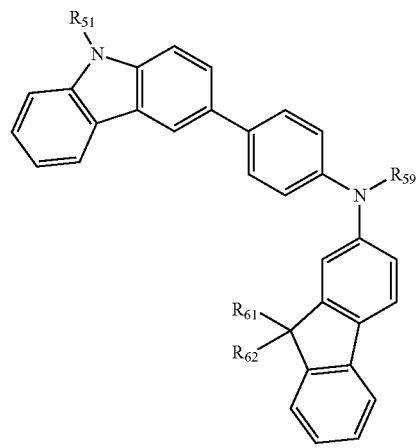

<Formula 300A>

In Formula 300A, $R_{51}$, $R_{62}$, $R_{61}$, and $R_{59}$ may be as defined above.

In some non-limiting embodiments, at least one of the HIL, HTL, and H-functional layer may include at least one of the compounds represented by Formulae 301 to 320 below:

301

302

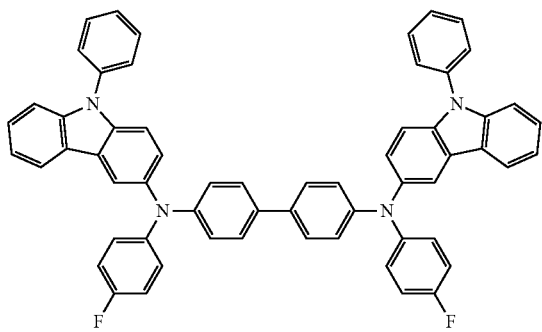
303
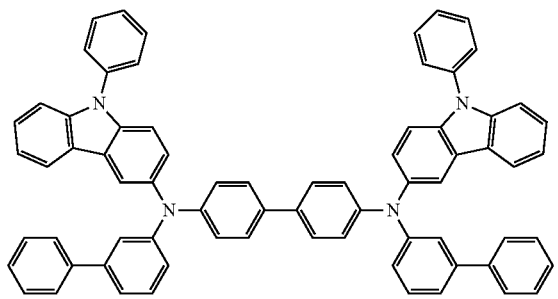
307
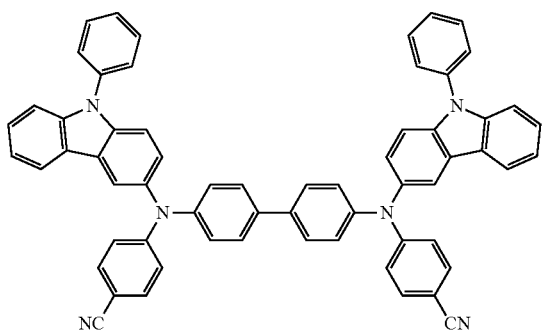
304
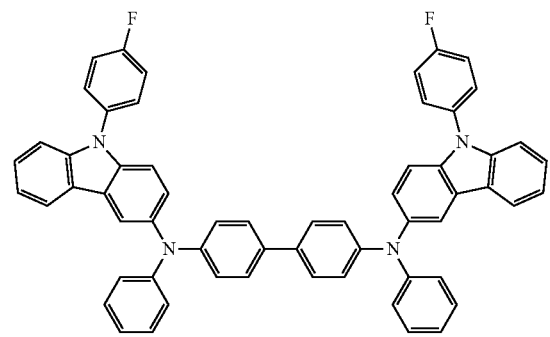
308
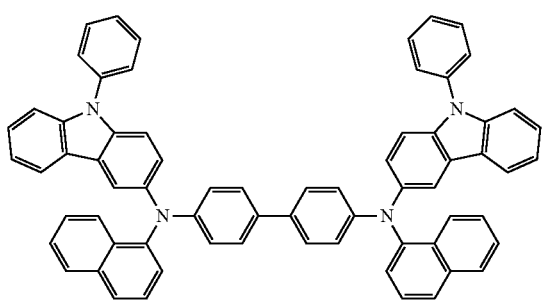
305
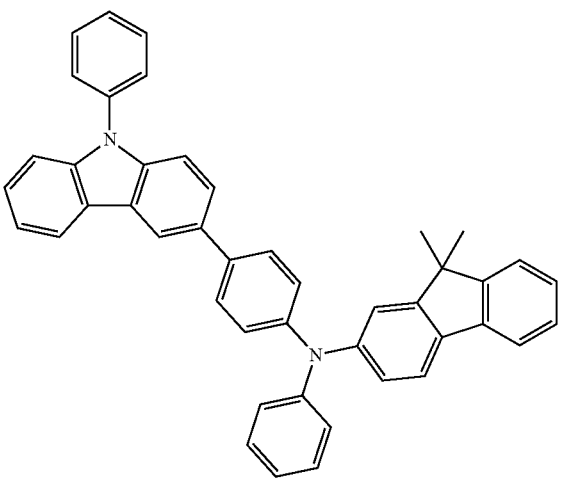
309
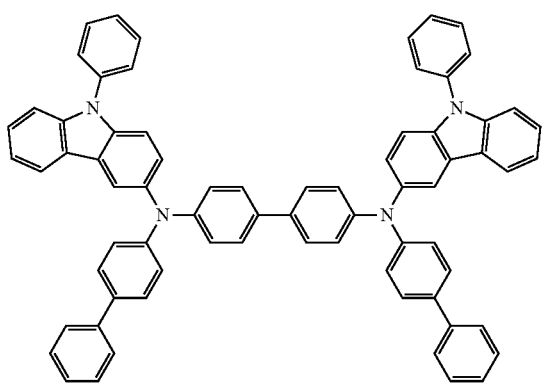
306

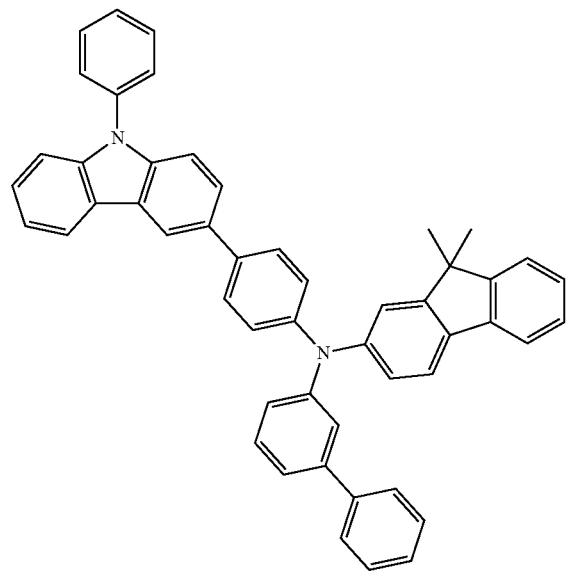
310
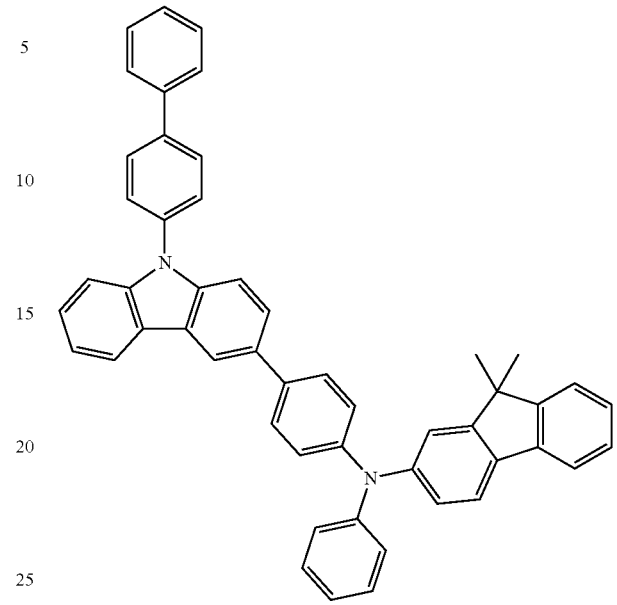
312
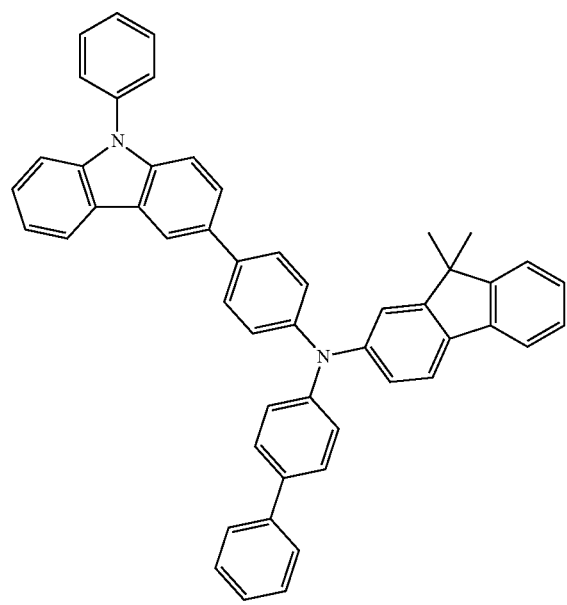
311
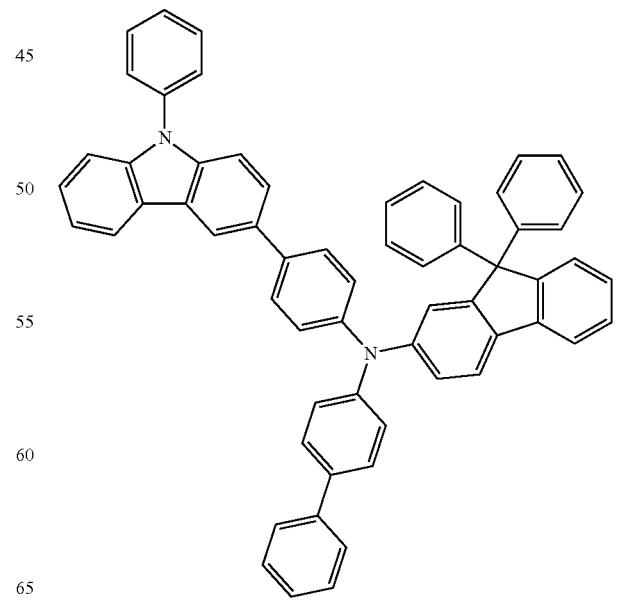
313

314
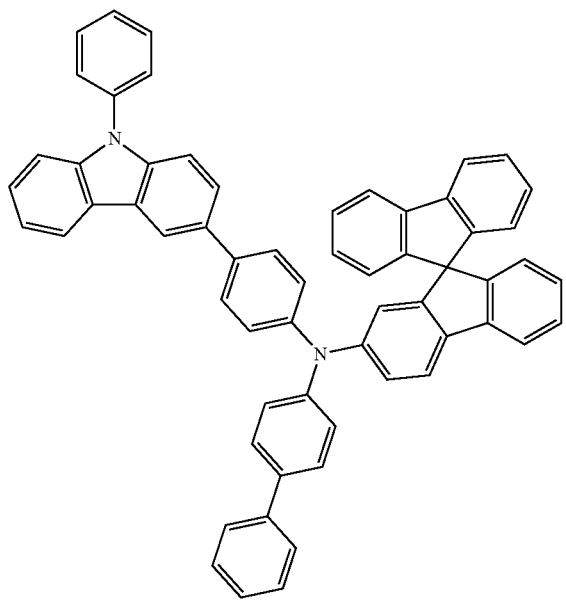
316
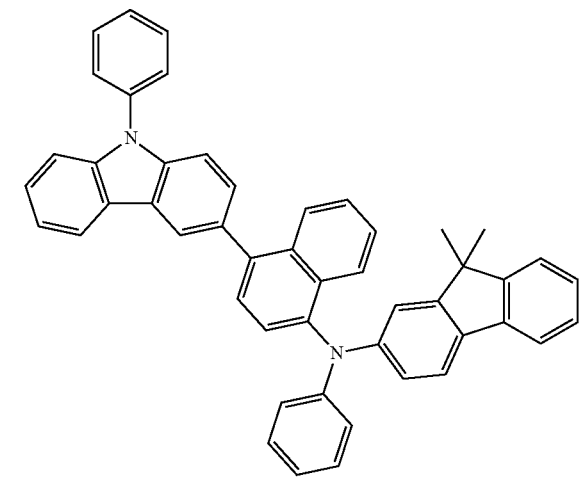
315
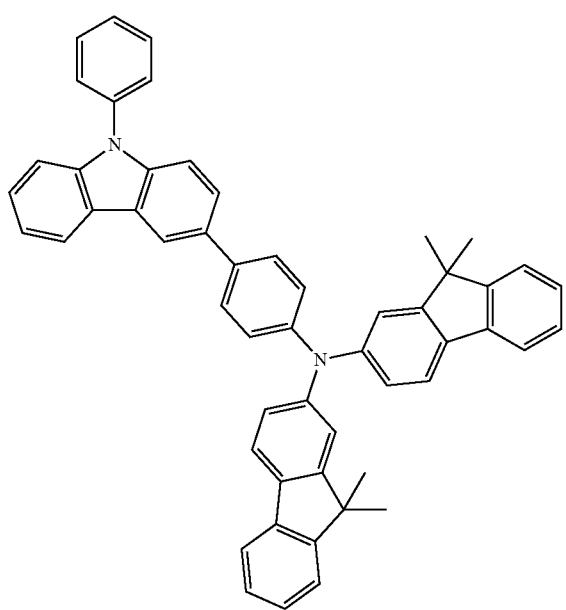
317
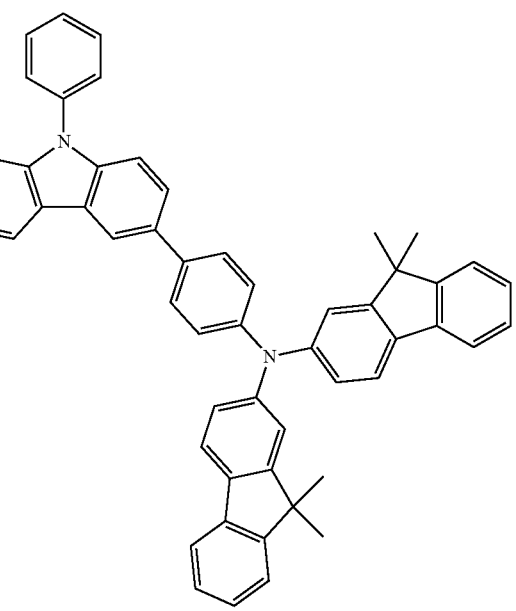

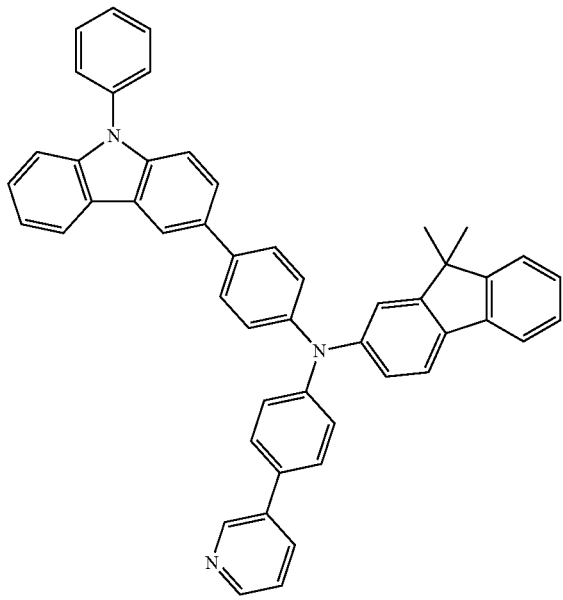

318

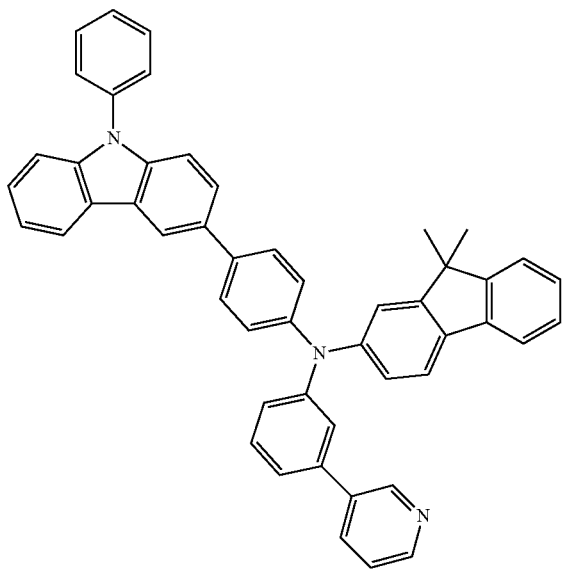

319

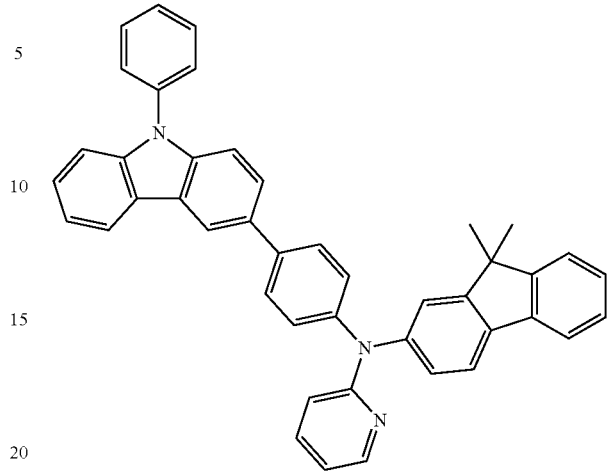

320

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Formula 200 below:

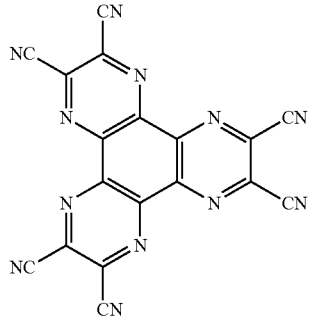

<Formula 200>

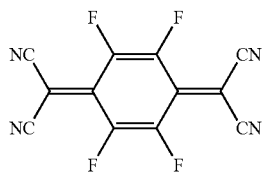

<F4-CTNQ>

When the hole injection layer, hole transport layer, or H-functional layer further includes a charge-generating material, the charge-generating material may be homogeneously dispersed or inhomogeneously distributed in the layer.

A buffer layer may be disposed between the EML and at least one of the HIL, HTL, and H-functional layer. The buffer layer may compensate for an optical resonance distance of light according to a wavelength of the light emitted from the EML, and thus may increase efficiency. The buffer layer may include any hole injecting material or hole transporting material that is suitable. In some other embodiments, the buffer layer may include the same material as one of the materials included in the HIL, HTL, and H-functional layer that underlies the buffer layer.

Then, an EML may be formed on the HTL, H-functional layer, or buffer layer by vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using a variety of known light-emitting materials. In some embodiments, the EML may be formed using a known host and a dopant. Dopants that may be used to form the EML may include either a fluorescent dopant or a phosphorescent dopant which are suitable in the art.

Non-limiting examples of a known host are Alq3, 4,4'-N, N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below:

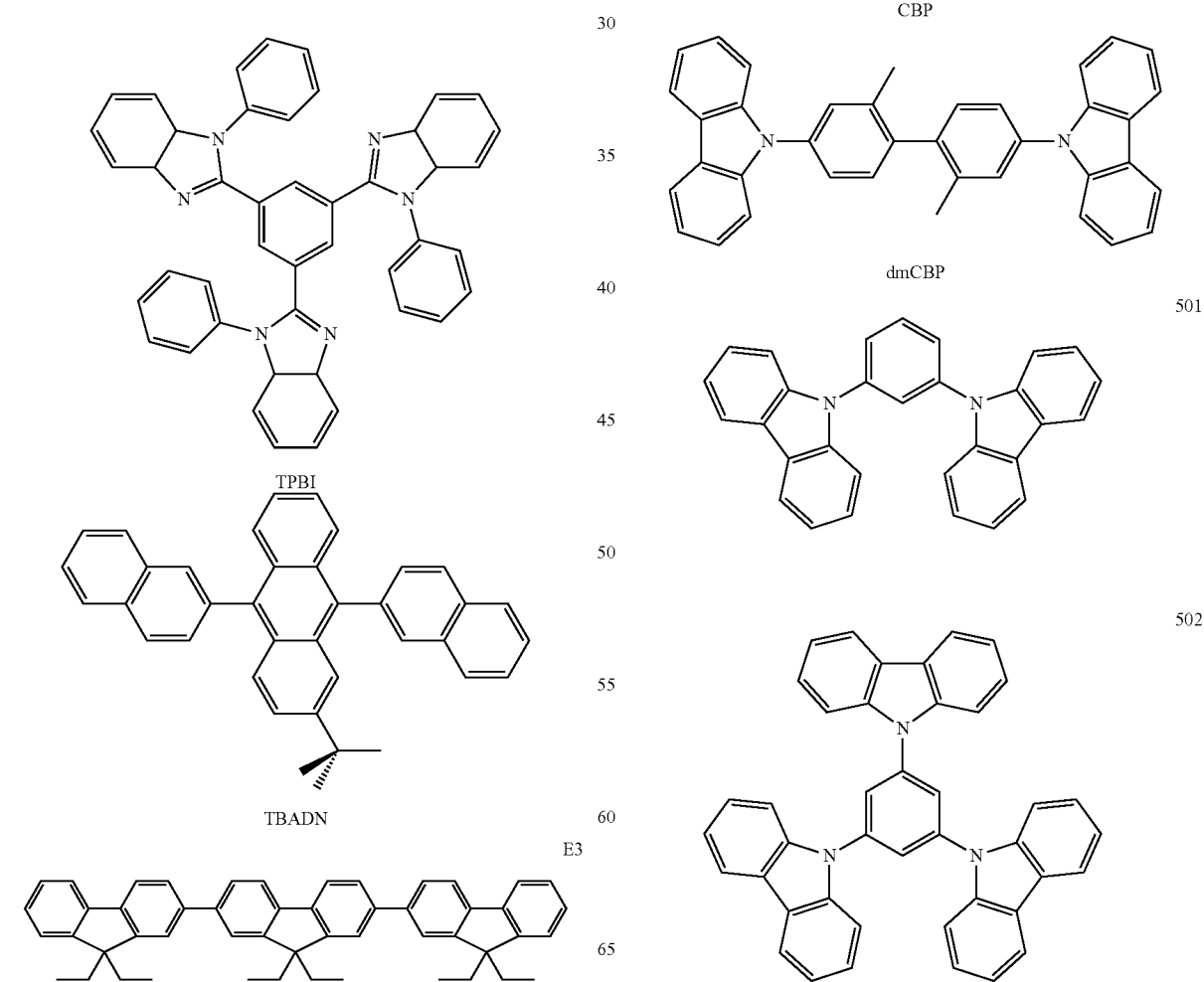

503
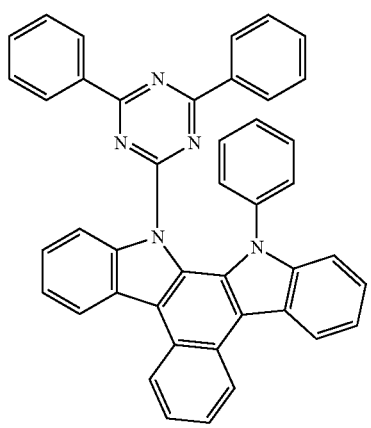
504
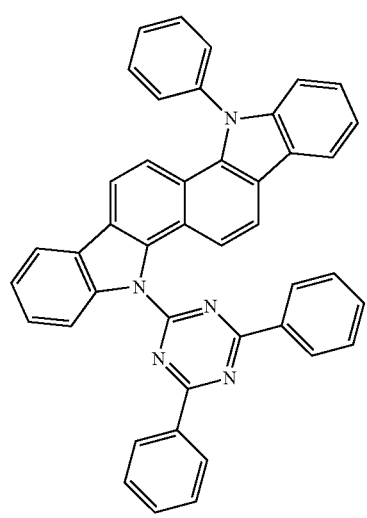
505
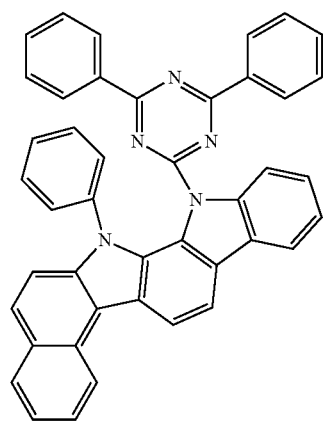
506
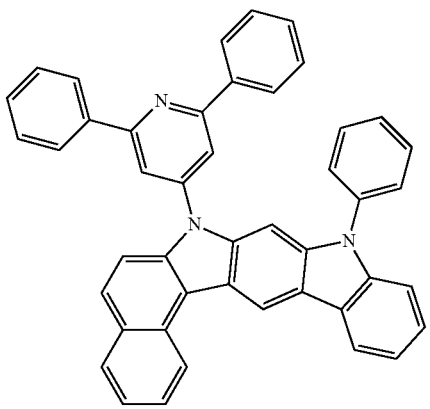
507
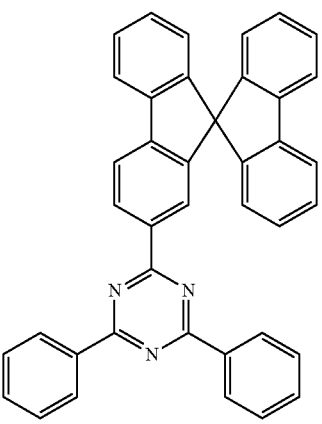
508
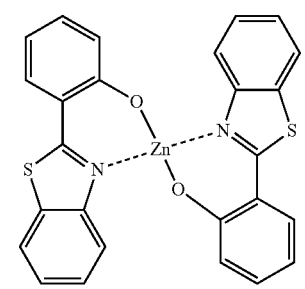
509
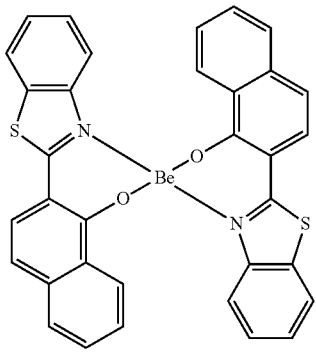

In some embodiments, an anthracene-based compound represented by Formula 400 below may be used as the host.

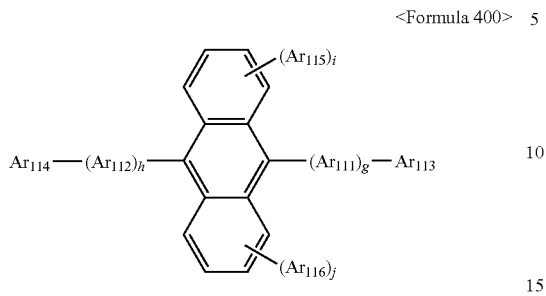

<Formula 400>

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently a substituted or unsubstituted $C_1$-$C_{10}$ alkyl group, or a substituted or unsubstituted $C_5$-$C_{60}$ aryl group; and g, h, i, and j may be each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that is substituted with at least one of a phenyl group, a naphthyl group, and an anthryl group.

In Formula 400 above, g, h, i, and j may be each independently 0, 1, or 2.

In Formula 400, $Ar_{113}$ to $Ar_{116}$ may be each independently one of a $C_1$-$C_{10}$ alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; or

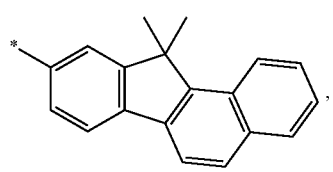 [SMILES: *c1ccc2c(c1)C(C)(C)c1c-2ccc2ccccc12]

but are not limited thereto.

For example, the anthracene-based compound of Formula 400 above may be one of the compounds represented by the following formulae, but is not limited thereto:

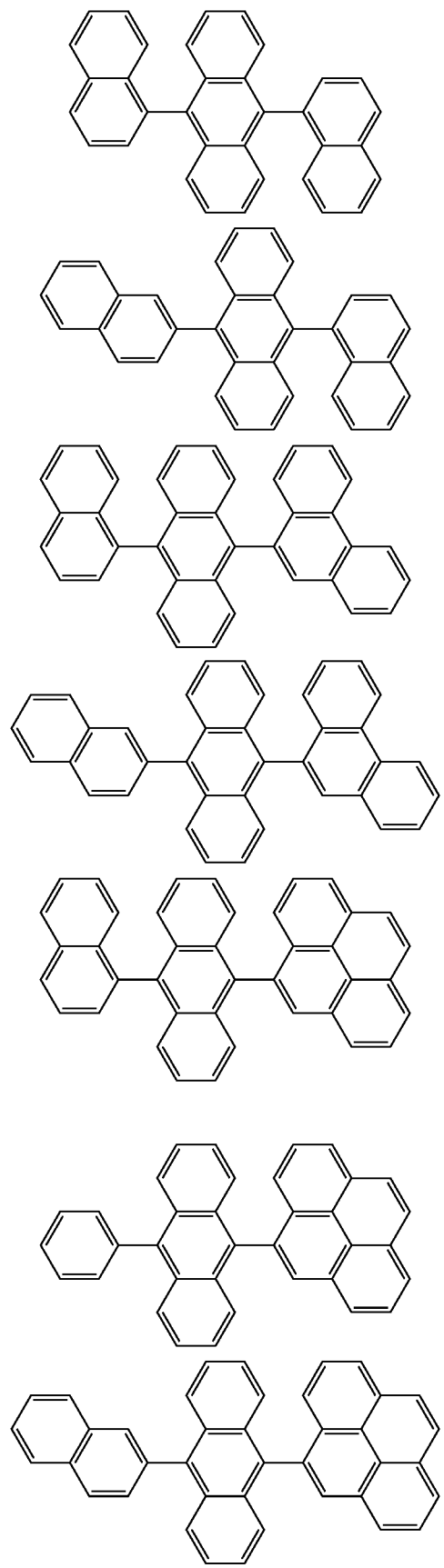

-continued
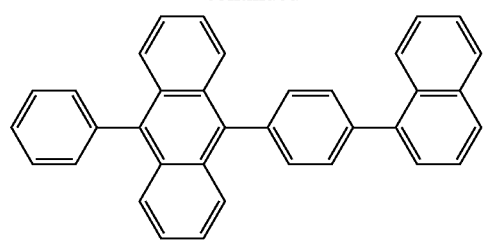
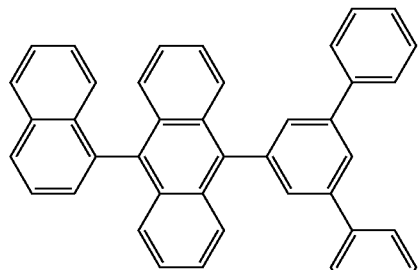
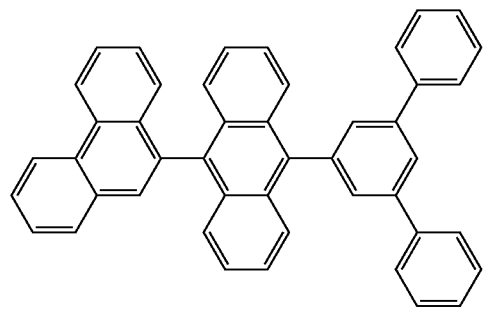
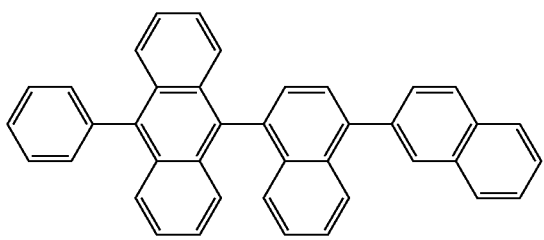
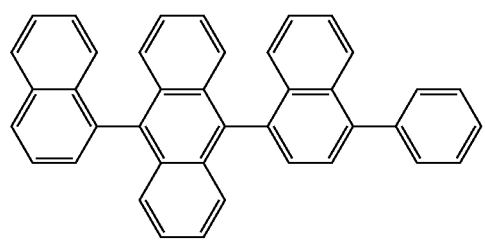
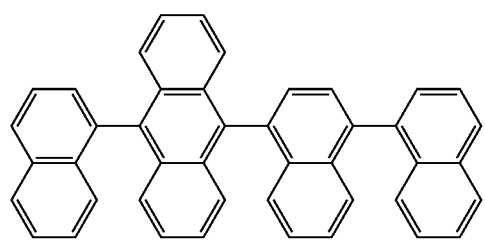
-continued
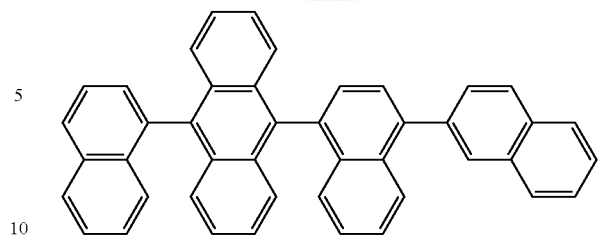
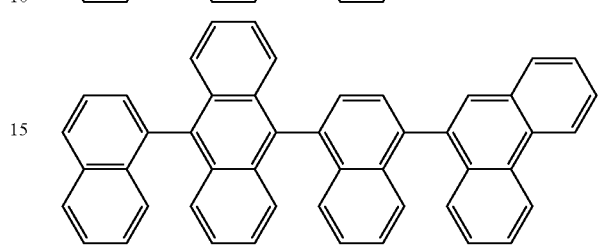
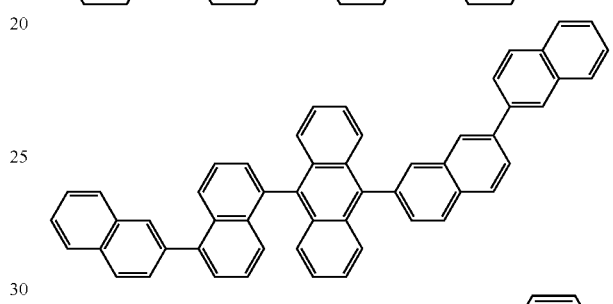
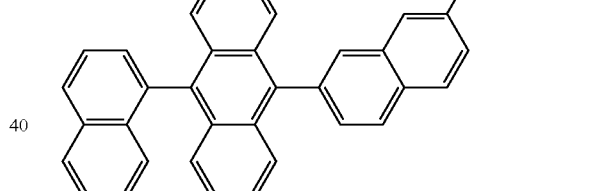
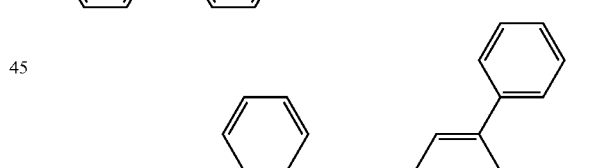

-continued
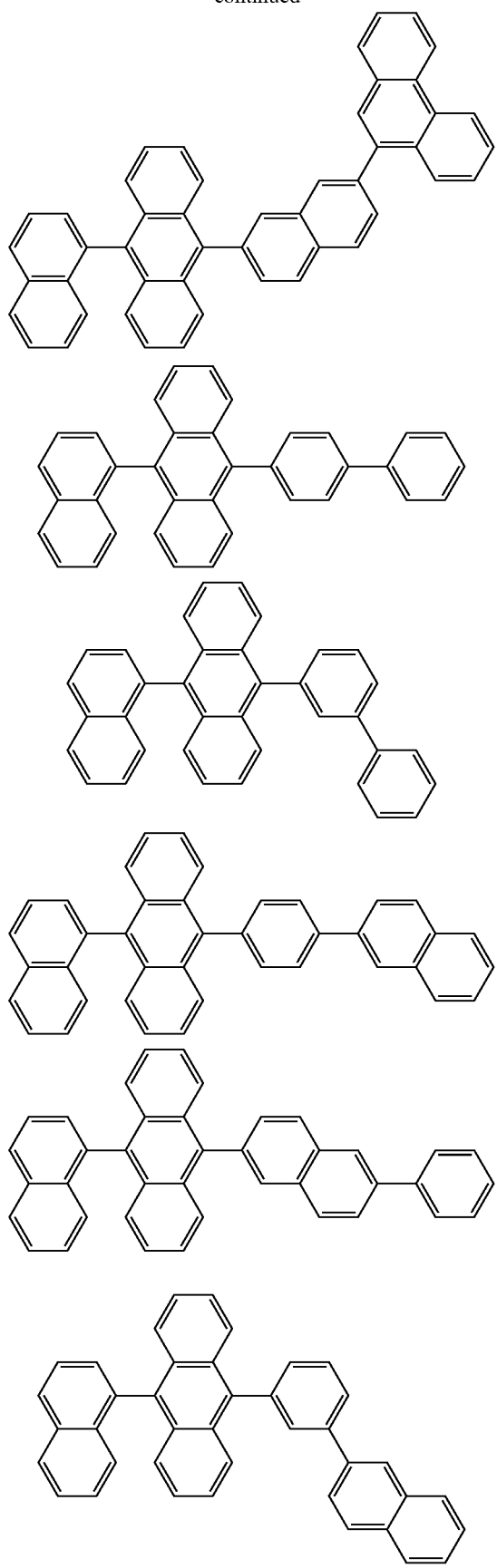
-continued
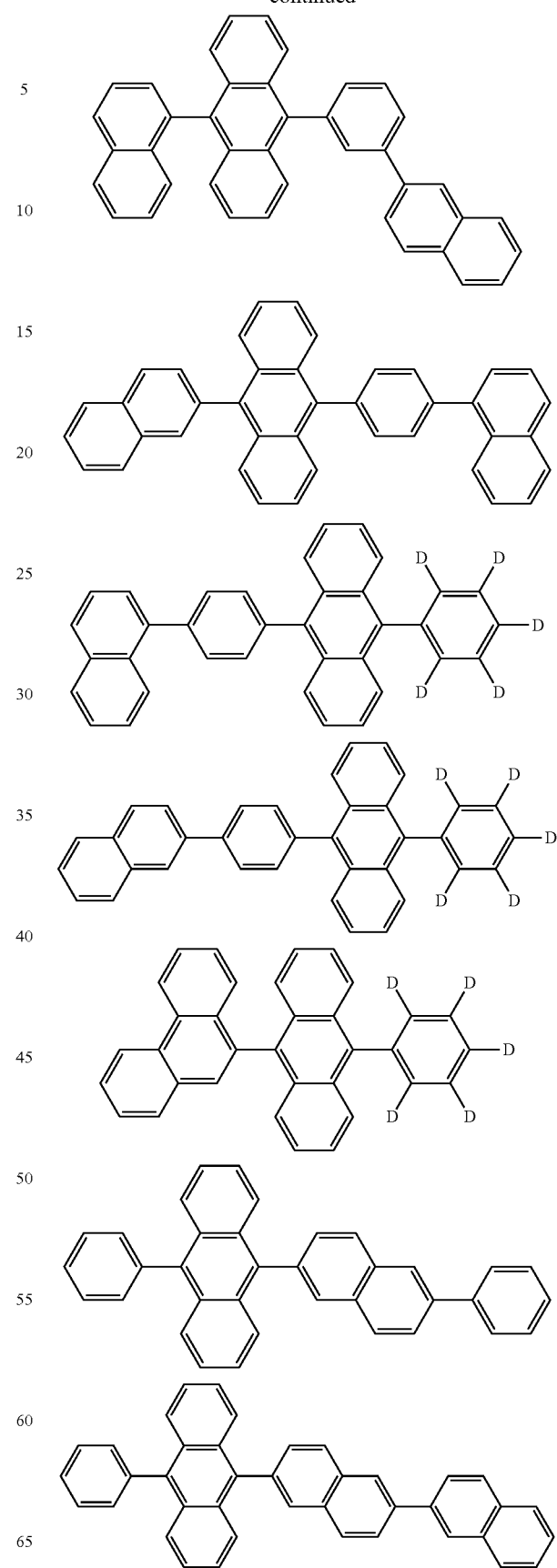

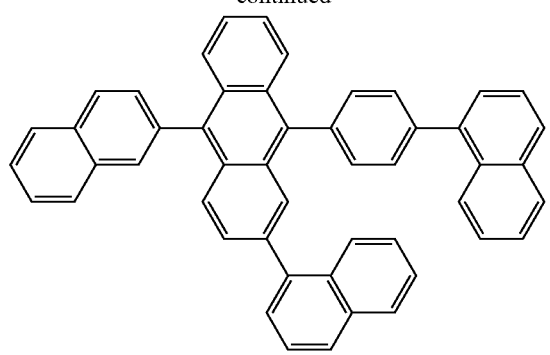
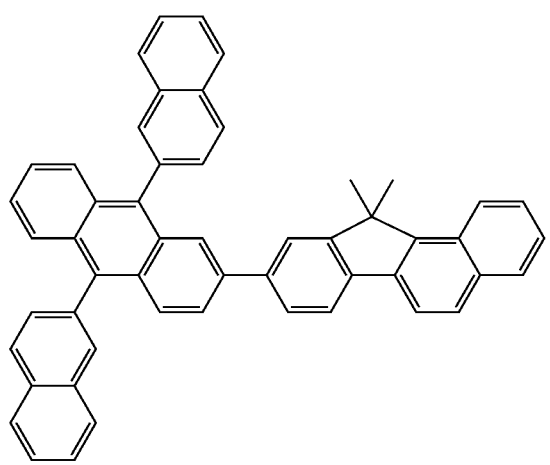
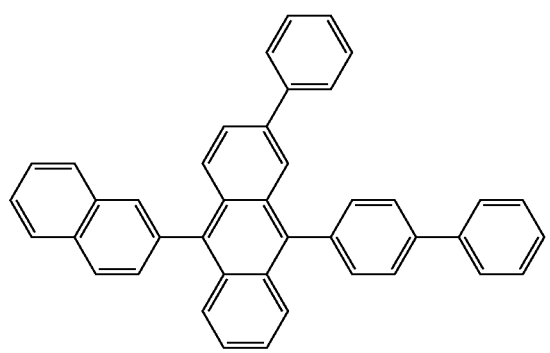
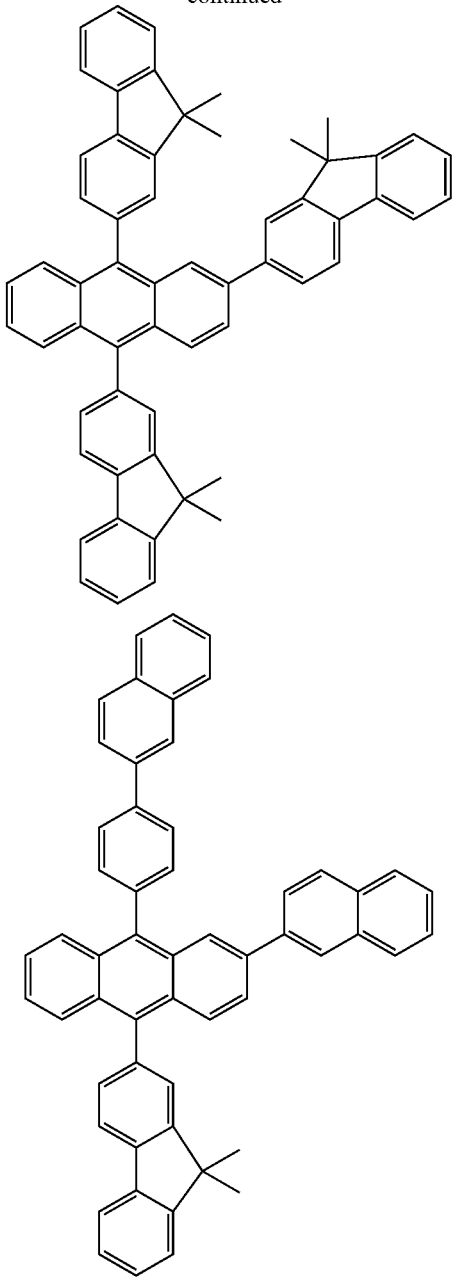
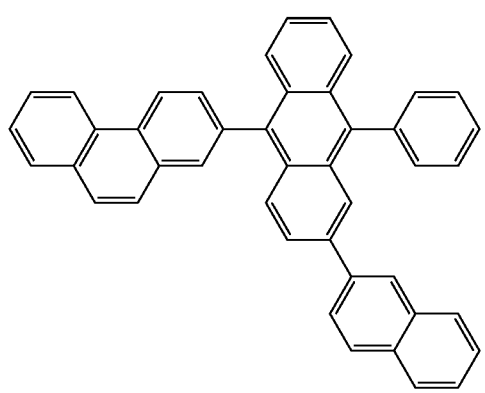

In some embodiments, an anthracene-based compound represented by Formula 401 below may be used as the host:

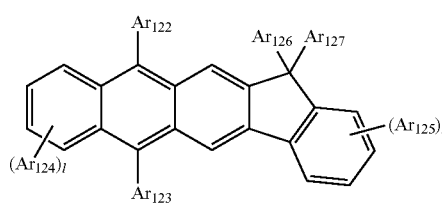

<Formula 401>

$Ar_{122}$ to $Ar_{125}$ in Formula 401 above may be defined as described above in conjunction with $Ar_{113}$ of Formula 400, and thus detailed descriptions thereof are not provided here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene-based compound of Formula 401 above may be one of the compounds represented by the following formulae, but is not limited thereto:

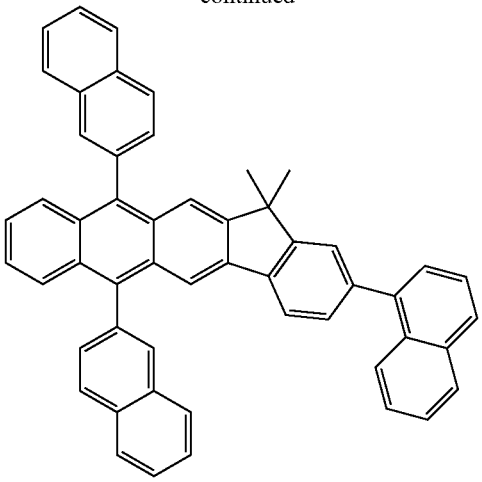

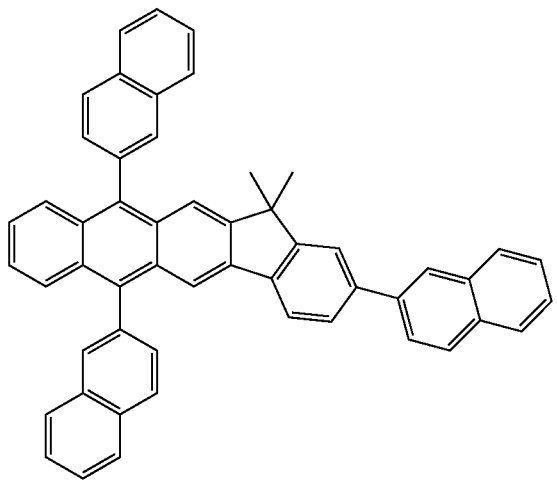

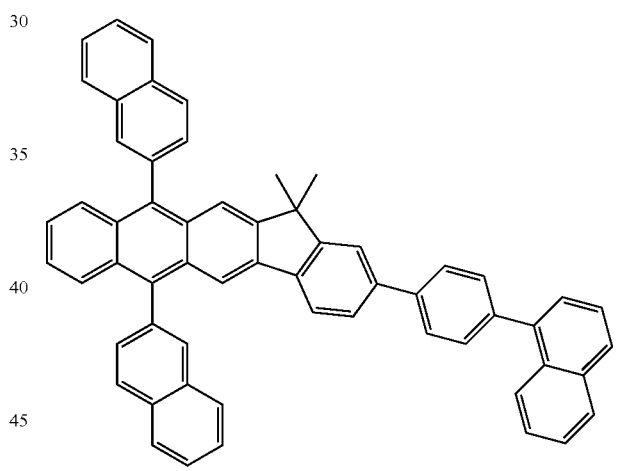

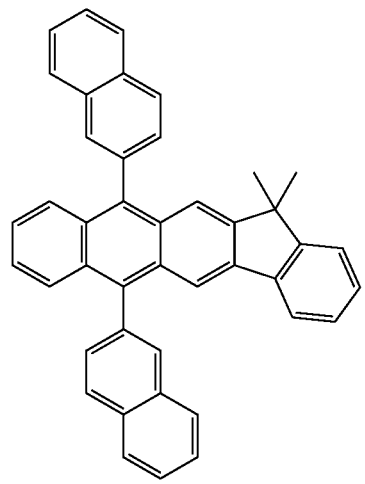

When the organic light-emitting device is a full color organic light-emitting device, the EML may be patterned into a red EML, a green EML, and a blue EML.

At least one of the red EML, the green EML, and the blue EML may include a dopant below (ppy=phenylpyridine).

Non-limiting examples of the blue dopant are compounds represented by the following formulae:
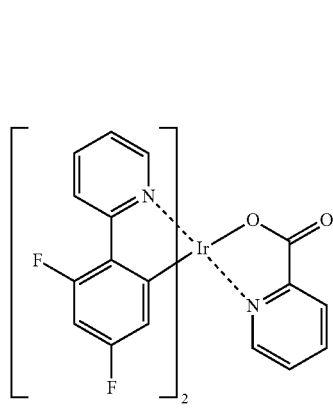
F₂Irpic
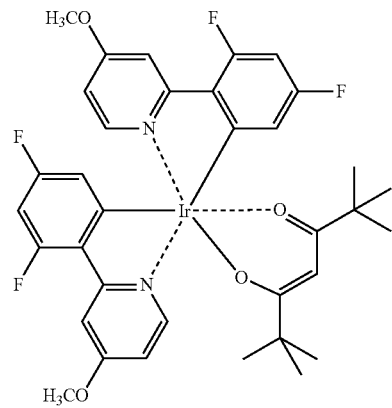
(F₂ppy)₂Ir(tmd)
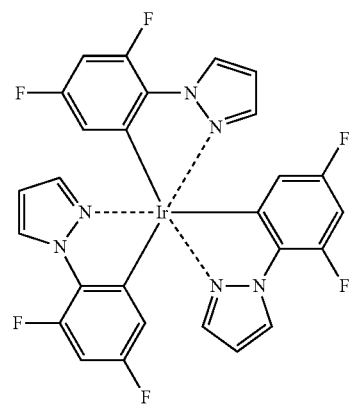
Ir(dfppz)₃
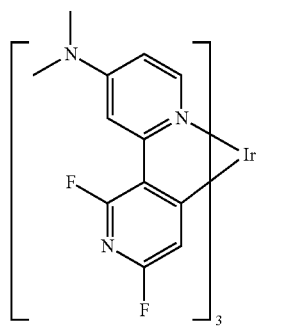
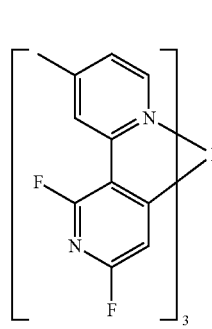
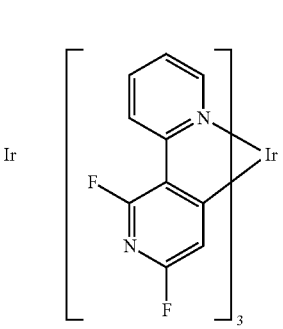
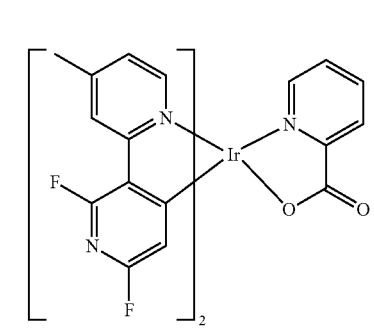
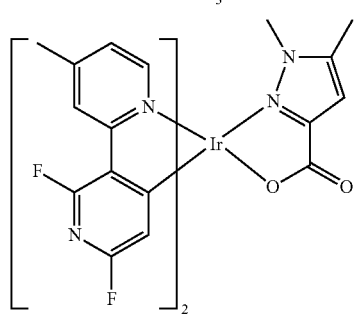
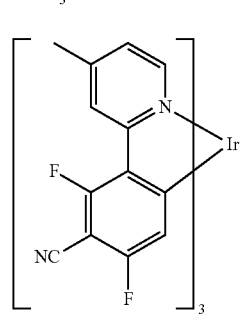
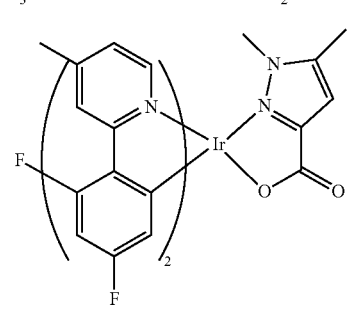
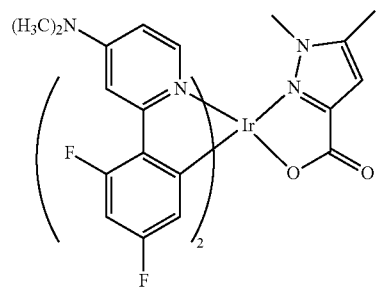
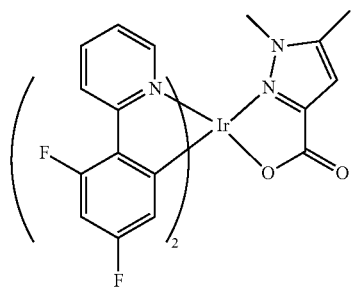
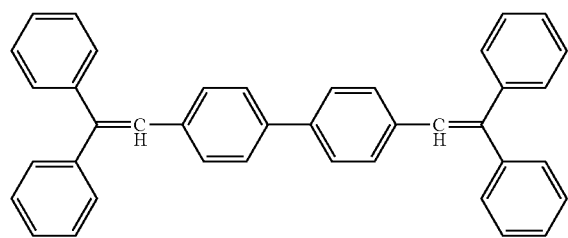
DPVBi

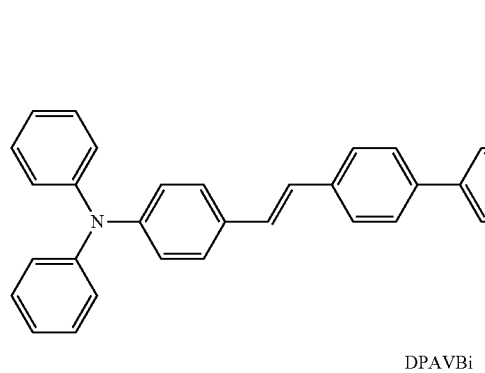
DPAVBi
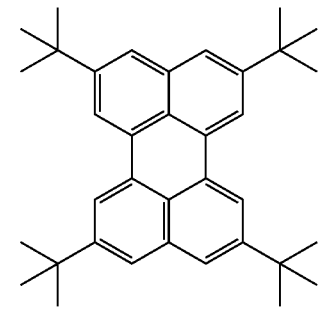
TBPe
Non-limiting examples of the red dopant are compounds represented by the following formulae:
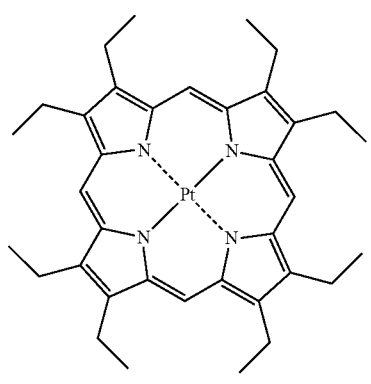
PtOEP
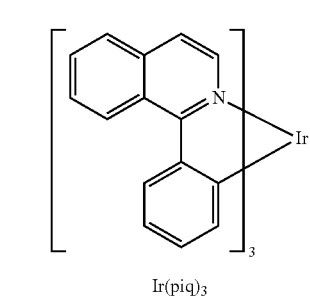
Ir(piq)₃
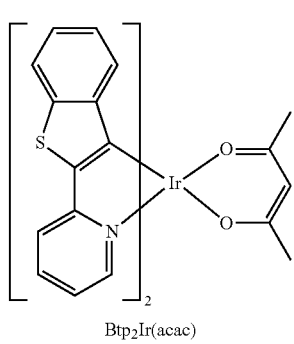
Btp₂Ir(acac)
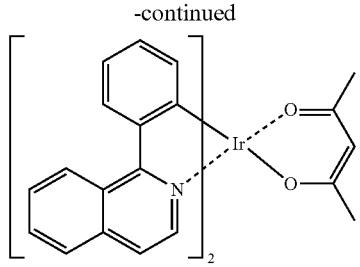
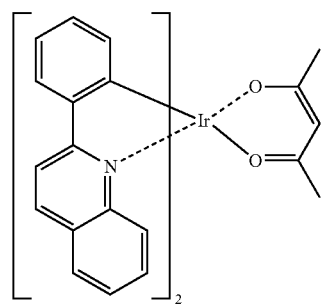
Ir(pq)₂(acac)
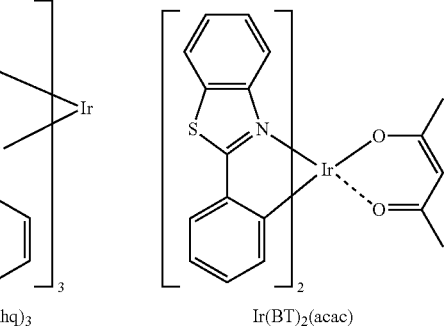
Ir(2-phq)₃  Ir(BT)₂(acac)

-continued
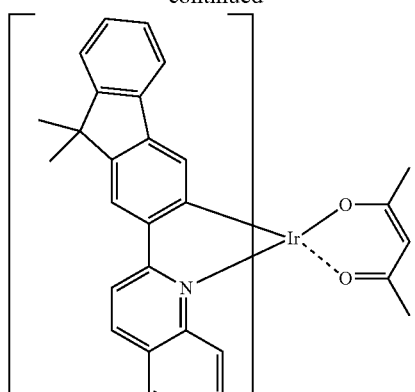
Ir(flq)₂(acac)
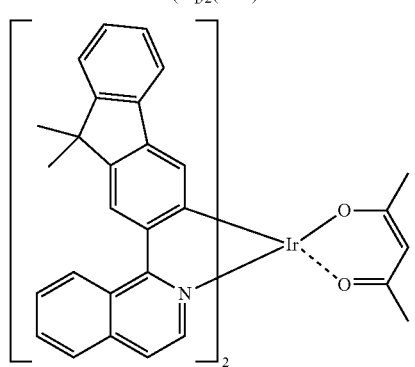
Ir(fliq)₂(acac)
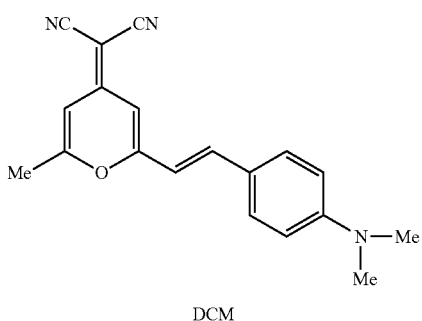
DCM
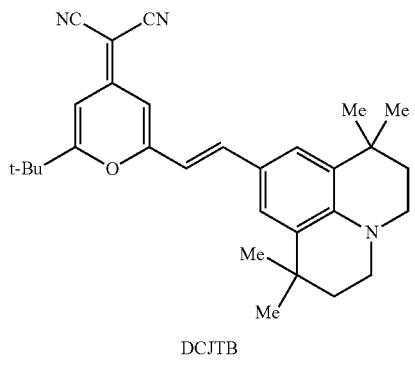 [SMILES: CC(C)(C)C1=CC(=C(C#N)C#N)C=C(/C=C/c2cc3c4c(c2)C(C)(C)CCN4CCC3(C)C)O1]
DCJTB
Non-limiting examples of the green dopant are compounds represented by the following formulae:
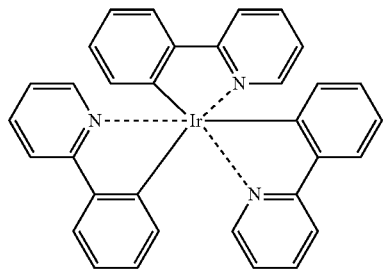
Ir(ppy)₃
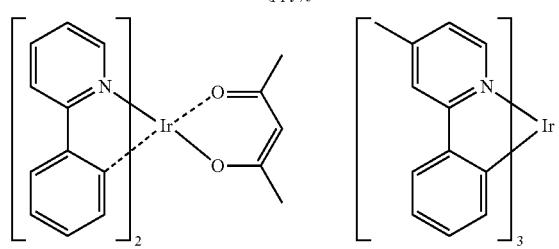
Ir(ppy)₂(acac)  Ir(mpyp)₃
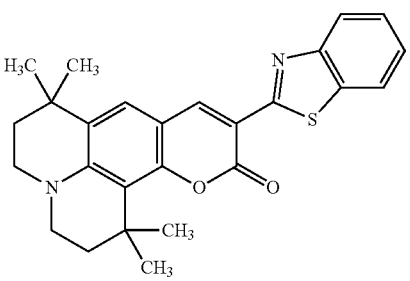
C545T
Non-limiting examples of the dopant that may be used in the EML are Pd-complex or Pt complexes represented by the following formulae:
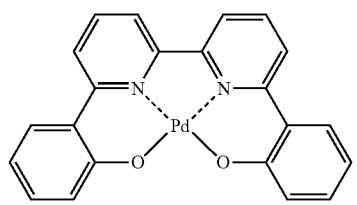
D1
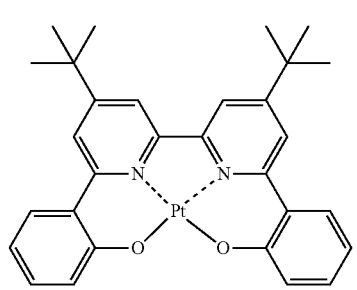
D2

-continued
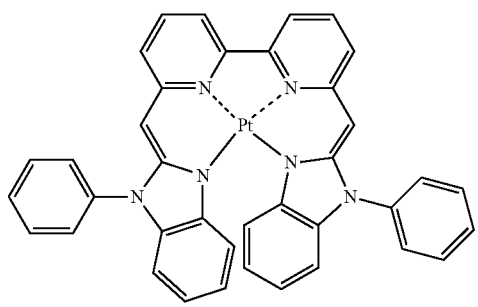
D3
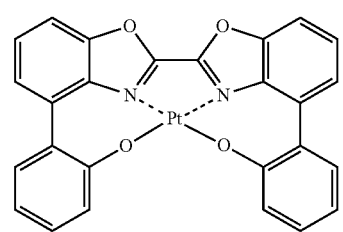
D4
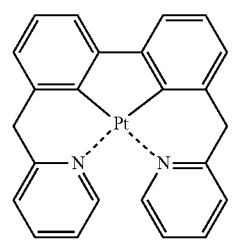
D5
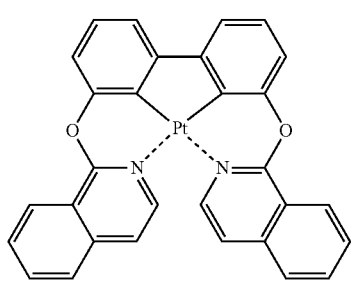
D6
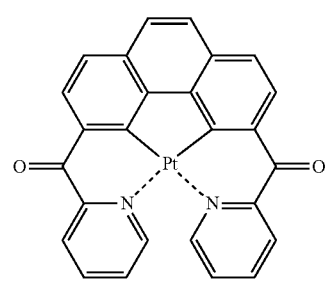
D7
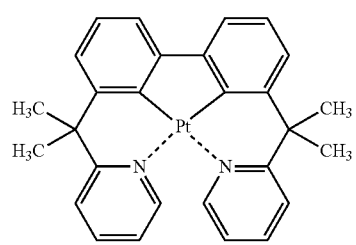
D8
-continued
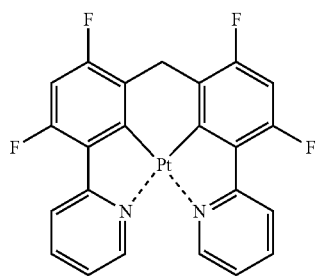
D9
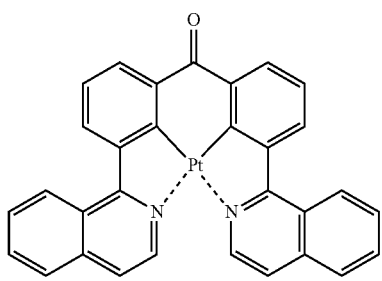
D10
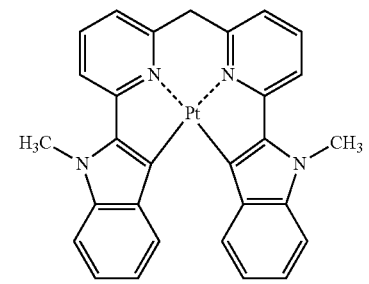
D11
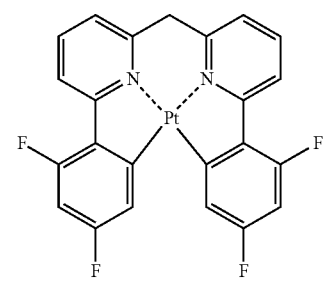
D12
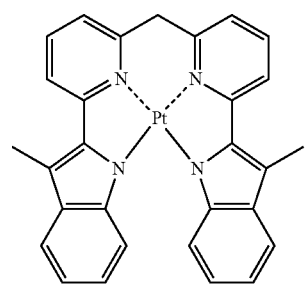
D13

D14
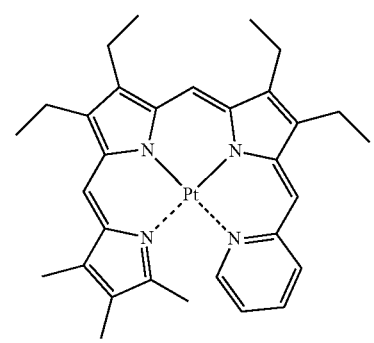
D15
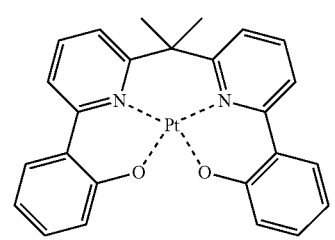
D16
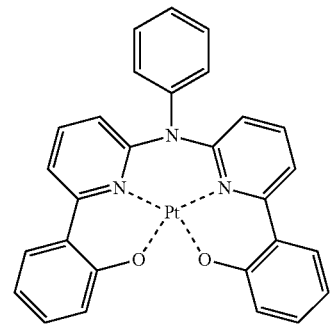
D17
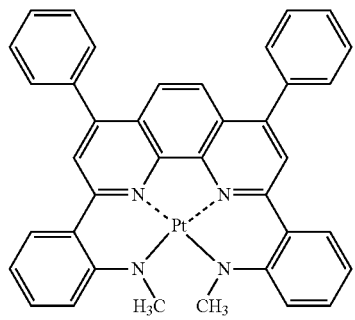
D18
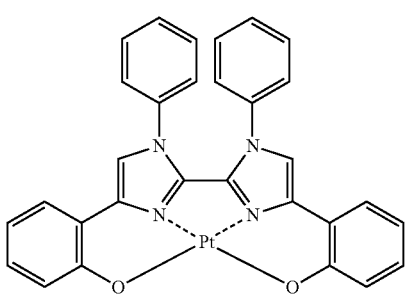
D19
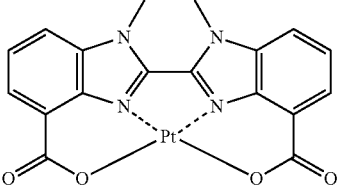
D20
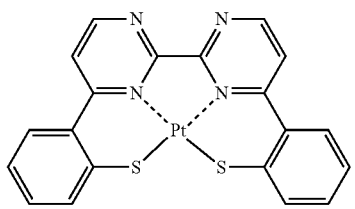
D21
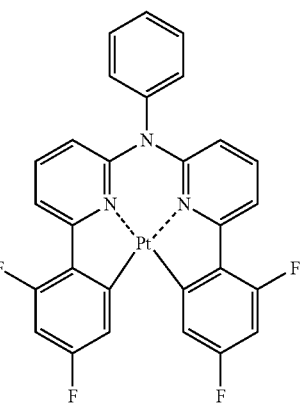
D22
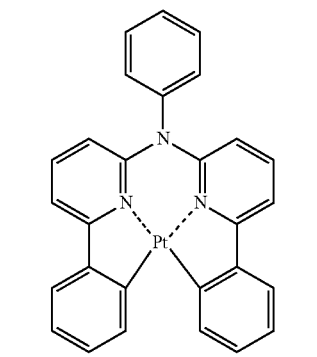
D23
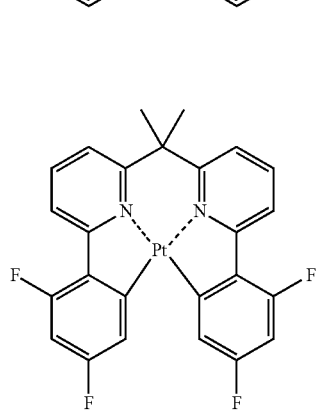

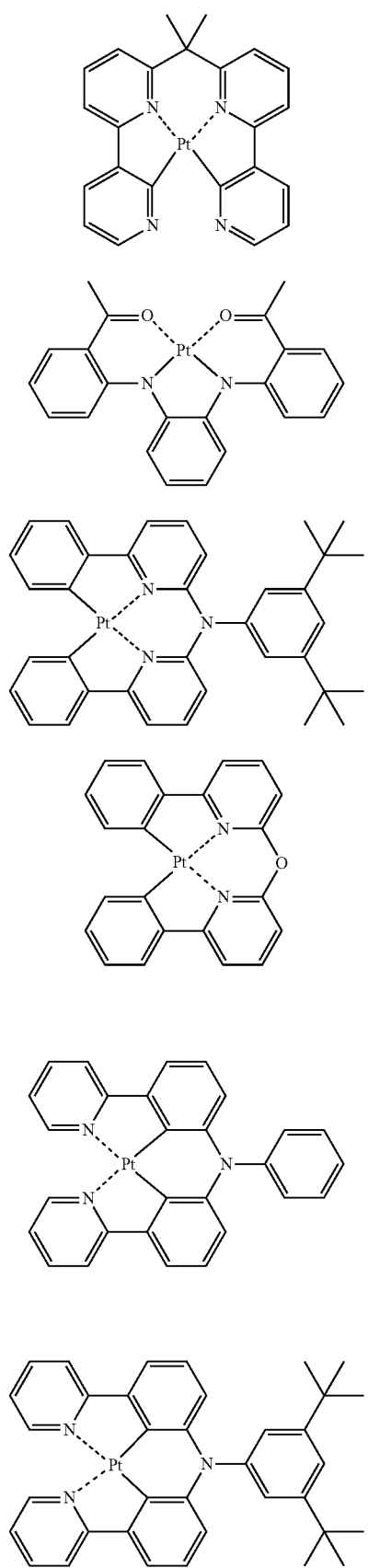
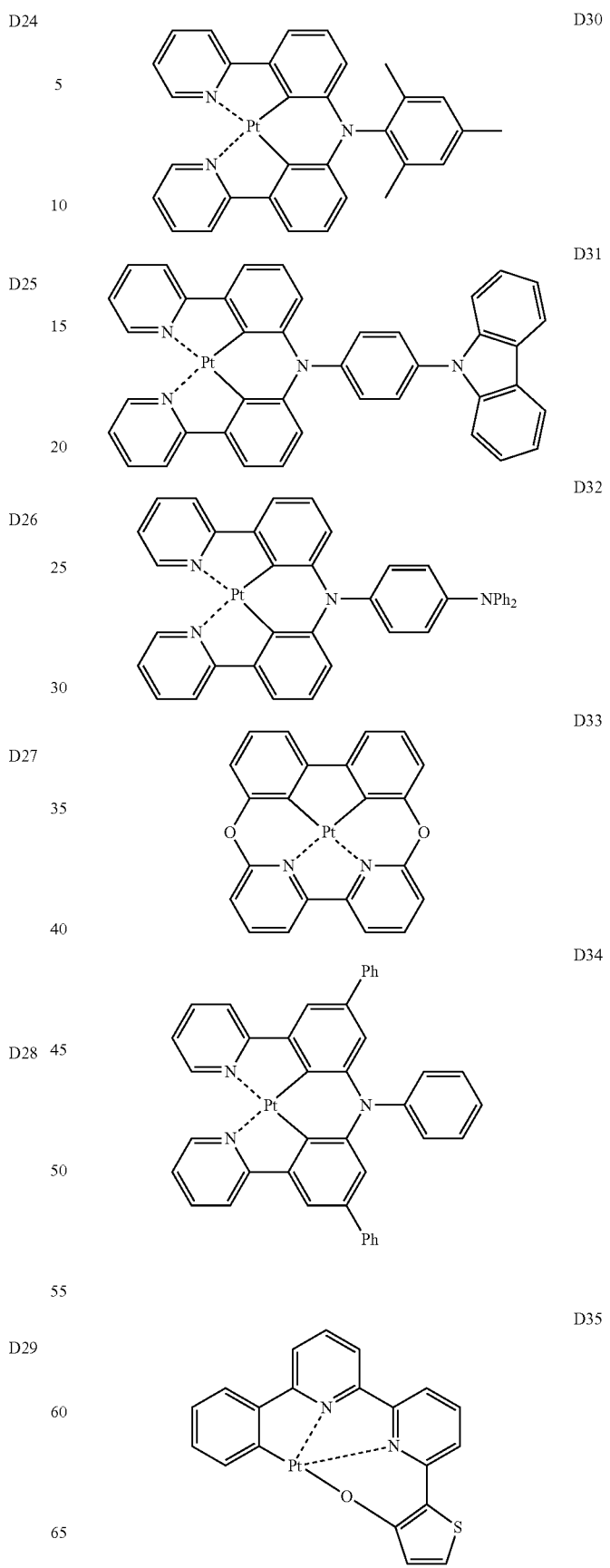

D36 D37 D38 D39 D40 D41 D42 D43 D44 D45

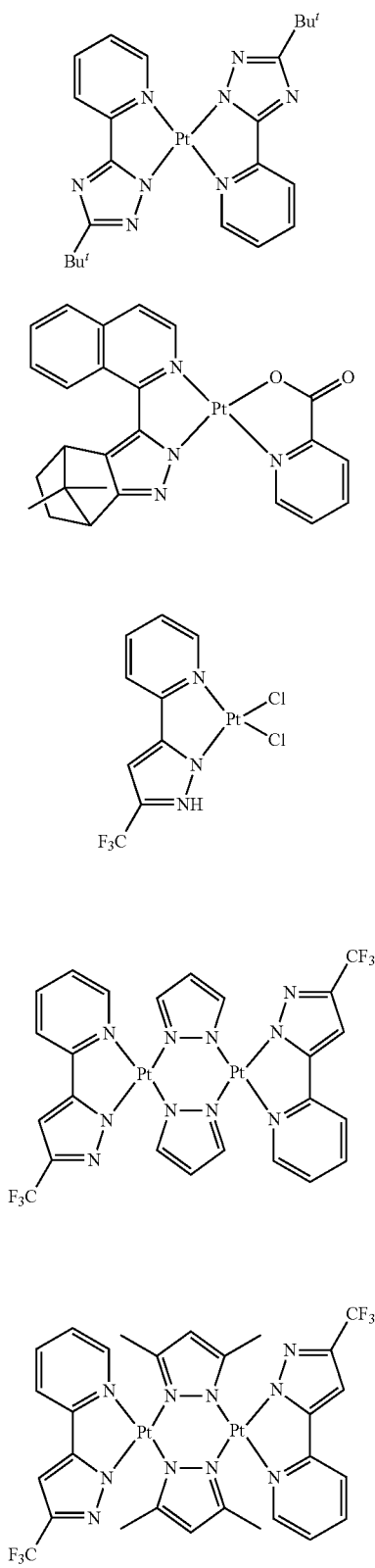

Non-limiting examples of the dopant that may be used in the EML are Os complexes represented by the following formulae:

Os(fppz)$_2$(CO)$_2$

Os(fppz)$_2$(PPh$_2$Me)$_2$

Os(bppz)$_2$(PPh$_3$)$_2$

Os(fptz)$_2$(PPh$_2$Me)$_2$

Os(hptz)$_2$(PPhMe$_2$)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, from about 200 Å to about 600 Å. When the thickness of the EML is within these ranges, the EML may have good light-emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL.

A material for forming the ETL may be the compound of Formula 1 above or any known material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinolin-10-olate (Bebq$_2$), 9,10-di(naphthalene-2-yl)anthracene (ADN), Compound 201, and Compound 202, but are not limited thereto.

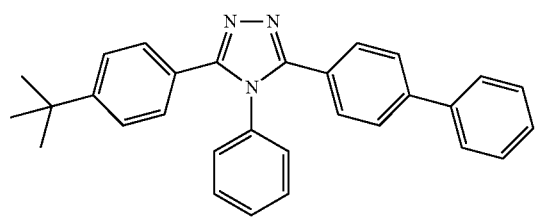

TAZ

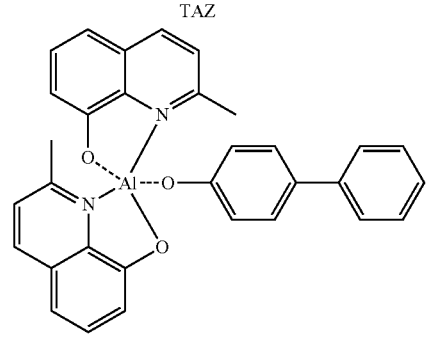

BAlq

<Compound 201>

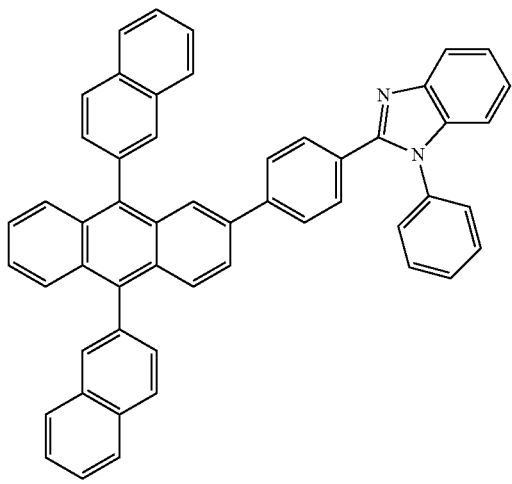

<Compound 202>

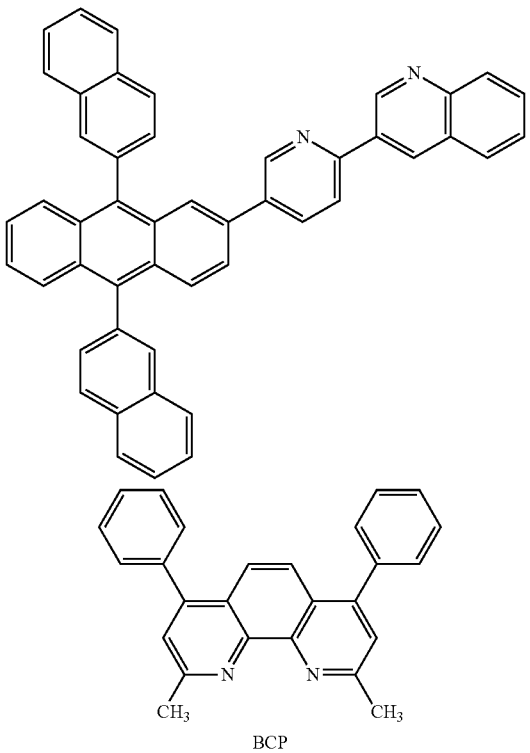

BCP

The thickness of the ETL may be from about 100 Å to about 1000 Å, and in some embodiments, from about 150 Å to about 500 Å. When the thickness of the ETL is within these ranges, the ETL may have satisfactory electron transporting ability without a substantial increase in driving voltage.

In some embodiments, the ETL may further include a metal-containing material, in addition to any known electron-transporting organic compound.

The metal-containing material may include a lithium (Li) complex. Non-limiting examples of the Li complex are lithium quinolate (LiQ) and Compound 203 below:
<Compound 203>

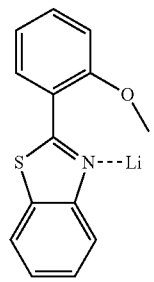

Then, an EIL, which facilitates injection of electrons from the cathode, may be formed on the ETL, but is not limited thereto, and any suitable electron injecting material may be used to form the EIL.

Non-limiting examples of the suitable electron material for forming the EIL are LiF, NaCl, CsF, Li$_2$O, and BaO, which are suitable in the art. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

Finally, the second electrode is disposed on the organic layer. The second electrode may be a cathode that is an electron injection electrode. A material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of the drawing is described above, the present invention is not limited thereto.

When a phosphorescent dopant is used in the EML, a hole blocking layer (HBL) may be formed between the ETL and the EML or between the E-functional layer and the EML by using vacuum deposition, spin coating, casting, LB deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any suitable hole-blocking material may be used. Non-limiting examples of hole-blocking materials are oxadiazole derivatives, triazole derivatives, and phenanthroline derivatives. For example, 2,9-dimethyl-4,7-diphenyl-1,10-phenanthroline (BCP) represented by the following formula may be used as a material for forming the HBL:

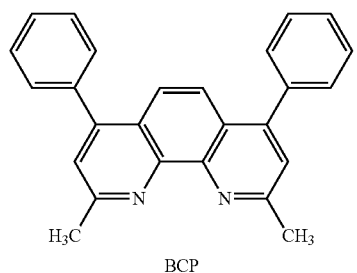

BCP

The thickness of the HBL may be from about 20 Å to about 1000 Å, and in some embodiments, from about 30 Å to about 300 Å. When the thickness of the HBL is within these ranges, the HBL may have improved hole blocking ability without a substantial increase in driving voltage.

According to embodiments of the present invention, the organic light-emitting device may be included in various suitable flat panel display devices, such as in a passive matrix organic light-emitting display device or in an active matrix organic light-emitting display device. In particular, when the organic light-emitting device is included in an active matrix organic light-emitting display device including a thin-film transistor, a first electrode on a substrate may function as a pixel electrode, which is electrically connected to a source electrode or a drain electrode of the thin-film transistor. Moreover, the organic light-emitting device may also be included in flat panel display devices having double-sided screens.

In some embodiments, the organic layer of the organic light-emitting device may be formed of the compound of Formula 1 by using a deposition method or may be formed using a wet method of coating a solution of the compound of Formula 1.

Hereinafter, the present invention will be described in more detail with reference to the following synthesis examples and other examples. However, these examples are for illustrative purposes only and are not intended to limit the scope of the present invention.

EXAMPLE

Synthesis Example 1

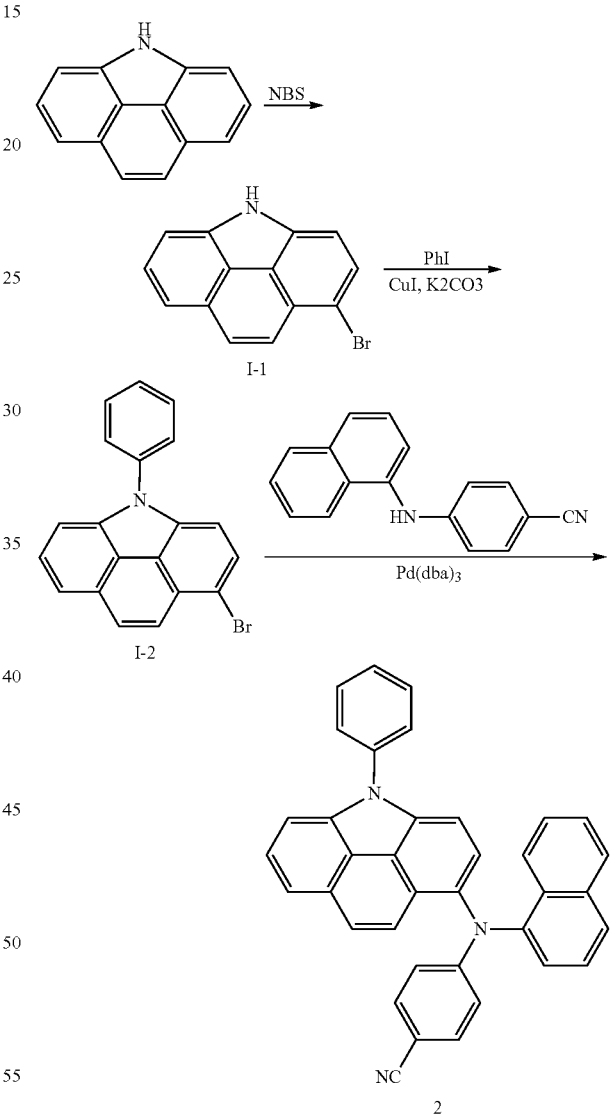

Synthesis of Intermediate I-1

1.78 g (10.0 mmol) of N-bromosuccinimide was added to a solution, in which 1.91 g (10.0 mmol) of 6H-benzo[def] carbazole is completely dissolved in 60 mL of carbon tetrachloride ($CCl_4$), and then stirred at about 80° C. for about 30 minutes. The reaction solution was cooled to room temperature, and then stirred for about 30 minutes to precipitate crystals. The crystals were collected using a filter under reduced pressure, and then washed with methanol to obtain 1.1 g of Intermediate I-1 as white crystals (yield: 45%). This compound was identified using liquid chromatography-mass spectrometry (LC-MS). $C_{14}H_8BrN:M^+245.9$ Synthesis of Intermediate I-2

2.7 g (10.0 mmol) of Intermediate I-1, 2.5 g (12.0 mmol) of iodobenzene, 0.2 g (1.0 mmol) of 1,10-phenanthroline, 0.2 g (2.0 mmol) of CuI, and 4.1 g (30.0 mmol) $K_2CO_3$ were dissolved in 30 mL of N,N-dimethylformamide (DMF), and stirred at about 80° C. for about 24 hours. The reaction solution was cooled to room temperature, and then extracted three times with 30 mL of water and 40 mL of diethylether. The organic phase was collected and was dried using magnesium sulfate to evaporate the solvent. The residue was separated and purified using silica gel column chromatography to obtain 3.07 g of Intermediate I-2 (yield: 89%). This compound was identified using LC-MS. $C_{20}H_{12}BrN\ M^+272.1$ Synthesis of Compound 2

In a nitrogen atmosphere, 3.46 g (10.0 mmol) of Intermediate I-2, 2.68 g (11.0 mmol) of 4-(naphthalene-1-ylamino) benzonitrile, 2.9 g (30 mmol) of KOtBu, 0.02 g (0.2 mmol) of $Pd_2(dba)_3$, and 0.02 g (0.1 mmol) of $P(t-Bu)_3$ were dissolved in 50 mL of toluene, and stirred at about 90° C. for about 3 hours. After completion of the reaction, the reaction solution was cooled to room temperature, and then extracted three times with distilled water and 40 mL of diethylether. The organic phase was collected and was dried using magnesium sulfate to evaporate the solvent. The residue was separated and purified using silica gel column chromatography to obtain 3.7 g of Compound 2 (yield: 73%). This compound was identified using mass spectrometry/fast atom bombardment (MS/FAB) and $^1H$ NMR.

$C_{37}H_{23}N_3$ cal. 509.19. found 510.31.

$^1H$ NMR ($CDCl_3$, 400 MHz) δ 8.04-8.01 (m, 1H), 7.87-7.85 (m, 1H), 7.79-7.77 (m, 1H), 7.55-7.30 (m, 15H), 7.19-7.15 (t, 1H), 6.77-6.75 (ss, 1H), 6.69-6.67 (m, 1H), 6.57-6.53 (m, 2H)

Synthesis of Compound 7

3.5 g of Compound 7 (yield: 72%) was obtained in the same manner as in Synthesis of Compound 2, except that 4-[4-(1-phenyl-1H-benzoimidazol-2-yl)phenylamino]-benzonitrile was used instead of 4-(naphthalene-1-ylamino)benzonitrile in Synthesis of Compound 2. This compound was identified using MS/FAB and $^1H$ NMR.

Synthesis of Compound 13

3.8 g of Compound 13 (yield: 70%) was obtained in the same manner as in Synthesis of Compound 2, except that 4-(4,4-dimethyl-9H-fluorene-2-ylamino)benzonitrile was used instead of 4-(naphthalene-1-ylamino)benzonitrile in Synthesis of Compound 2. This compound was identified using MS/FAB and $^1H$ NMR.

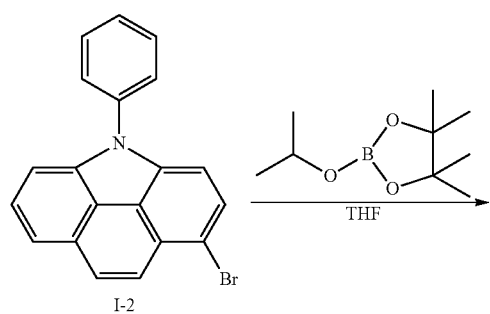

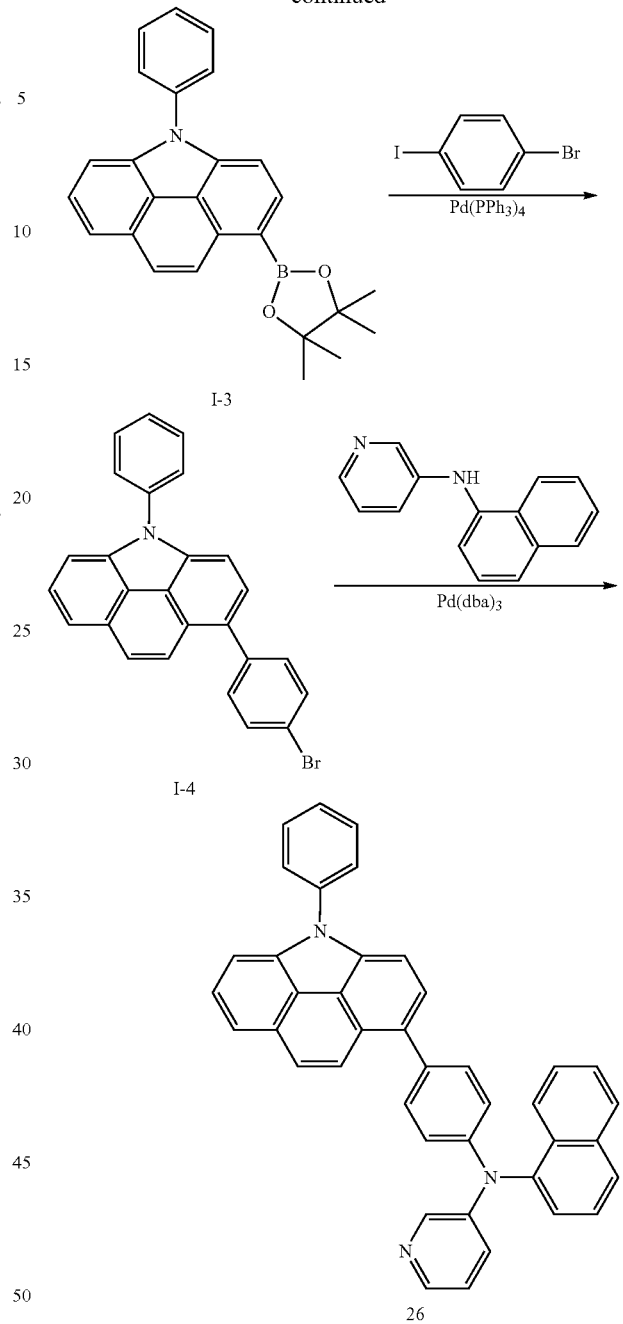

Synthesis of Intermediate I-3

10 g (28.8 mmol) of Intermediate I-2 was dissolved in 30 mL of THF, and 10 mL (25.0 mmol, 2.5 M in Hexane) of n-BuLi was slowly added dropwise at about −78° C. The solution was stirred for about 1 hour at the same temperature, and 9.3 mL (50 mmol) of 2-isoproxy-4,4,5,5,-tetramethyl-1,3,2-dioxaborolane was slowly added dropwise. The reaction solution was then stirred at about −78° C. for about 1 hour, followed by stirring at room temperature for about 24 hours. After completion of the reaction, 50 mL of 10% HCl aqueous solution and 50 mL of $H_2O$ were added, and then extracted three times with 80 mL of diethylether. The organic phase was collected and was dried using magnesium sulfate to evaporate the solvent. The residue was separated and purified using silica gel column chromatography to obtain 8.49 g of Intermediate I-3 (yield: 75%). This compound was identified using LC-MS. $C_{26}H_{24}BNO_2$: M+394.2

Synthesis of Intermediate I-4

3.9 g (10 mmol) of Intermediate I-3, 4.2 g (15.0 mmol) of 4-bromo-iodobenzene, 0.58 g (0.5 mmol) of Pd(PPh$_3$)$_4$, and 4.1 g (30.0 mmol) of K$_2$CO$_3$ were dissolved in 30 mL of a mixed solvent of THF/H$_2$O (2/1 by volume), and then stirred at about 80° C. for about 5 hours. After the reaction solution was cooled to room temperature, 40 mL of water was added to the reaction solution, which was then extracted three times with 50 mL of diethylether. The organic phase was collected and was dried using magnesium sulfate to evaporate the solvent. The residue was separated and purified using silica gel column chromatography to obtain 2.6 g of Intermediate I-4 (yield: 62%). This compound was identified using LC-MS. C$_{26}$H$_{16}$Br$_2$N M$^+$423.3

Synthesis of Compound 26

In a nitrogen atmosphere, 4.2 g (10.0 mmol) of Intermediate I-4, 2.4 g (11.0 mmol) of N-(naphthalene-1-yl)pyridine-3-amine, 2.9 g (30 mmol) of KOtBu, 0.02 g (0.2 mmol) of Pd$_2$(dba)$_3$, and 0.02 g (0.1 mmol) of P(t-Bu)$_3$ were dissolved in 50 mL of toluene, and then stirred at about 90° C. for about 3 hours. After the reaction solution was cooled to room temperature, then extracted three times with 40 mL of distilled water and diethylether. The organic phase was collected and was dried using magnesium sulfate to evaporate the solvent. The residue was separated and purified using silica gel column chromatography to obtain 3.7 g of Compound 26 (yield: 66%). This compound was identified using MS/FAB and $^1$H NMR.

C$_{41}$H$_{27}$N$_3$ cal. 561.22. found 562.31.

$^1$H NMR (CDCl$_3$, 400 MHz) δ 8.53-5.52 (m, 1H), 8.27-8.24 (m, 1H), 8.01 (m, 1H), 7.87-7.85 (m, 1H), 7.79-7.77 (ss, 1H), 7.73 (m, 1H), 7.64-7.61 (m, 2H), 7.57-7.36 (m, 12H), 7.32-7.23 (m, 3H), 7.03-7.00 (m, 2H), 6.97-6.94 (m, 1H), 6.85-6.83 (m, 1H)

Synthesis of Compound 36

3.8 g of Compound 36 (yield: 75%) was obtained in the same manner as in Synthesis of Compound 26, except that 4-(4-quinoline-8-yl-phenylamino)benzonitrile was used instead of N-(naphthalene-1-yl)pyridine-3-amine in Synthesis of Compound 26. This compound was identified using MS/FAB and $^1$H NMR.

Synthesis of Compound 42

4.2 g of Compound 42 (yield: 75%) was obtained in the same manner as in Synthesis of Compound 26, except that 4-(4,6-dinaphthalene-2-yl-[1,3,5]triazine-2-ylamino)benzonitrile was used instead of N-(naphthalene-1-yl)pyridine-3-amine in Synthesis of Compound 26. This compound was identified using MS/FAB and $^1$H NMR.

Synthesis of Compound 47

4.2 g of Compound 47 (yield: 70%) was obtained in the same manner as in Synthesis of Compound 26, except that bis-(4-cyano-phenyl)amine was used instead of N-(naphthalene-1-yl)pyridine-3-amine in Synthesis of Compound 26. This compound was identified using MS/FAB and $^1$H NMR.

Synthesis of Compound 54

3.2 g of Compound 54 (yield: 68%) was obtained in the same manner as in Synthesis of Compound 26, except that 4'-bromo-4-iodo-biphenyl was used instead of 4-bromo-iodobenzene in Synthesis of Intermediate I-4, and 4-(4-pyridine-3-yl-phenylamino)benzonitrile was used instead of N-(naphthalene-1-yl)pyridine-3-amine in Synthesis of Compound 26. This compound was identified using MS/FAB and $^1$H NMR.

Synthesis of Compound 65

3.0 g of Compound 65 (yield: 65%) was obtained in the same manner as in Synthesis of Compound 26, except that 2-bromo-7-iodo-9,9-dimethyl-9H-fluorene was used instead of 4-bromo-iodobenzene in Synthesis of Intermediate I-4, and 4-(3,5-dipyridine-3-yl-phenylamino)benzonitrile was used instead of N-(naphthalene-1-yl)pyridine-3-amine in Synthesis of Compound 26. This compound was identified using MS/FAB and $^1$H NMR.

Synthesis of Compound 76

3.2 g of Compound 76 (yield: 70%) was obtained in the same manner as in Synthesis of Compound 2, except that 5'-iodo-[1,1':3',1"]terphenyl was used instead of iodobenzene in Synthesis of Intermediate I-2, and naphthalene-1-yl-pyridine-3-yl-amine was used instead of 4-(naphthalene-1-ylamino)benzonitrile in Synthesis of Compound 2. This compound was identified using MS/FAB and $^1$H NMR.

Synthesis of Compound 77

3.6 g of Compound 77 (yield: 72%) was obtained in the same manner as in Synthesis of Compound 2, except that 7-iodo-1,10c-dihydro-pyrene was used instead of iodobenzene in Synthesis of Intermediate I-2, and 4-(naphthalene-2-ylamino)benzonitrile was used instead of 4-(naphthalene-1-ylamino)benzonitrile in Synthesis of Compound 2. This compound was identified using MS/FAB and $^1$H NMR.

Synthesis of Compound 84

3.8 g of Compound 84 (yield: 77%) was obtained in the same manner as in Synthesis of Compound 2, except that phenyl-(4-quinoline-8-yl-phenyl)-amine was used instead of 4-(naphthalene-1-ylamino)benzonitrile in Synthesis of Intermediate I-2, and phenyl-(4-quinoline-8-yl-phenyl)-amine was used instead of 4-(naphthalene-1-ylamino)benzonitrile in Synthesis of Compound 2. This compound was identified using MS/FAB and $^1$H NMR.

Synthesis of Compound 88

3.5 g of Compound 88 (yield: 62%) was obtained in the same manner as in Synthesis of Compound 26, except that 2-bromo-5-(4-iodo-phenyl)pyridine was used instead of 4-bromo-iodobenzene in Synthesis of Intermediate I-4, and 4-(biphenyl-4-ylamino)benzonitrile was used instead of N-(naphthalene-1-yl)pyridine-3-amine in Synthesis of Compound 26. This compound was identified using MS/FAB and $^1$H NMR.

Additional compounds were synthesized using appropriate intermediate materials according to the synthetic pathways and the methods described as above, and were identified using $^1$H NMR and MS/FAB. The results are shown in Table 1 below.

Synthetic pathways and source materials for other compounds not in Table 1 will be obvious to one of ordinary skill in the art based on the synthetic pathways and source materials described above.

TABLE 1

| Compound | $^1$H NMR (CDCl$_3$, 400 MHz) | MS/FAB found | MS/FAB calc. |
|---|---|---|---|
| 2 | δ = 8.04-8.01 (m, 1H), 7.87-7.85 (m, 1H), 7.79-7.77 (m, 1H), 7.55-7.30 (m, 15H), 7.19-7.15 (t, 1H), 6.77-6.75 (ss, 1H), 6.69-6.67 (m, 1H), 6.57-6.53 (m, 2H) | 510.31 | 509.19 |

TABLE 1-continued

| Compound | ¹H NMR (CDCl₃, 400 MHz) | MS/FAB found | MS/FAB calc. |
|---|---|---|---|
| 7 | δ = 8.31-8.27 (m, 2H), 7.80-7.76 (m, 2H), 7.67-7.64 (m, 1H), 7.57-7.49 (m, 7H), 7.44-7.36 (m, 9H), 7.30-7.28 (m, 2H), 7.25-7.20 (m, 1H), 6.74-6.68 (m, 5H) | 652.35 | 651.24 |
| 9 | δ = 8.85 (m, 2H), 8.68-8.66 (m, 2H), 8.19-8.17 (m, 2H), 8.10-8.07 (ss, 2H), 8.04-8.02 (m, 2H), 7.88-7.85 (ss, 1H), 7.78-7.76 (m, 1H), 7.70-7.68 (m, 2H), 7.61-7.40 (m, 13H), 7.40-7.34 (m, 2H), 7.06-7.04 (ss, 1H) | 715.55 | 714.25 |
| 10 | δ = 8.89 (m, 2H), 8.67-8.66 (m, 2H), 7.95-7.92 (m, 2H), 7.79-7.76 (m, 1H), 7.68 (t, 1H), 7.55-7.47 (m, 8H), 7.41-7.36 (m, 5H), 7.31-7.29 (ss, 1H), 6.97-6.96 (d, 2H), 6.72-6.69 (m, 2H), 6.60-6.58 (d, 1H) | 614.33 | 613.23 |
| 13 | δ = 7.79-7.76 (m, 2H), 7.55-7.47 (m, 7H), 7.41-7.30 (m, 7H), 7.14-7.08 (m, 2H), 6.73-6.66 (m, 3H), 6.53-6.51 (ss, 1H), 6.45-6.44 (d, 1H), 1.61 (s, 6H) | 576.33 | 575.24 |
| 17 | δ = 7.79-7.76 (m, 1H), 7.56-7.47 (m, 5H), 7.43 (s, 1H), 7.40-7.34 (m, 8H), 6.74-6.71 (m, 4H), 6.68 (s, 1H) | 485.17 | 484.17 |
| 26 | δ = 8.31☐☐8.53-5.52 (m, 1H), 8.27-8.24 (m, 1H), 8.01 (m, 1H), 7.87-7.85 (m, 1H), 7.79-7.77 (ss, 1H), 7.73 (m, 1H), 7.64-7.61 (m, 2H), 7.57-7.36 (m, 12H), 7.32-7.23 (m, 3H), 7.03-7.00 (m, 2H), 6.97-6.94 (m, 1H), 6.85-6.83 (m, 1H) | 562.31 | 561.22 |
| 31 | δ = 7379-7.77 (ss, 1H), 7.73 (m, 1H), 7.61-7.44 (m, 10H), 7.40-7.36 (m, 3H), 7.32-7.30 (m, 1H), 7.08-7.03 (m, 2H), 6.97-6.93 (m, 2H), 6.76-6.72 (m, 1H), 6.23-6.19 (m, 2H) | 536.20 | 535.20 |
| 36 | δ = 8.98 (m, 1H), 8.38-8.36 (m, 1H), 8.20 (m, 1H), 8.15-8.13 (m, 1H), 7.79-7.77 (ss, 1H), 7.75-7.73 (m, 1H), 7.62-7.44 (m, 14H), 7.38-7.36 (m, 3H), 7.32-7.30 (m, 1H), 7.05-7.02 (m, 2H), 6.97-6.93 (m, 2H), 6.83-6.80 (m, 2H) | 663.25 | 662.25 |
| 39 | δ = 7.92-7.90 (m, 1H), 7.83-7.70 (m, 9H), 7.62-7.44 (m, 10H), 7.40-7.35 (m, 5H), 7.32-7.30 (dd, 1H), 7.25-7.21 (m, 1H), 7.16-7.12 (m, 1H), 6.99-6.96 (m, 2H), 6.93-6.89 (m, 2H), 6.84-6.81 (m, 2H) | 763.28 | 762.28 |
| 40 | δ = 7.79-7.70 (m, 11H), 7.62-7.44 (m, 10H), 7.40-7.36 (m, 1H), 7.32-7.30 (m, 1H), 7.10-7.05 (m, 2H), 6.95-6.94 (d, 2H), 6.92-6.89 (m, 2H), 6.66-6.62 (m, 1H), 6.30-6.26 (m, 2H) | 713.26 | 712.26 |
| 42 | δ = 8.85 (m, 2H), 8.68-8.66 (m, 2H), 8.18-8.17 (m, 2H), 8.10-8.07 (ss, 2H), 8.04-8.02 (m, 2H), 7.84-7.77 (m, 3H), 7.75-7.66 (m, 3H), 7.61-7.44 (m, 12H), 7.40-7.39 (m, 1H), 7.32-7.30 (m, 1H), 7.26-7.23 (m, 2H), 7.10-7.06 (m, 2H) | 791.33 | 790.28 |
| 47 | δ = 7.79-7.77 (ss, 1H), 7.75-7.73 (m, 1H), 7.61-7.44 (m, 10H), 7.40-7.35 (m, 5H), 7.32-7.30 (m, 1H), 6.97-6.93 (m, 2H), 6.83-6.79 (m, 4H) | 561.30 | 560.20 |
| 48 | δ = 7.79-7.77 (ss, 1H), 7.75-7.73 (m, 1H), 7.62-7.44 (m, 10H), 7.40-7.35 (m, 3H), 7.32-7.30 (m, 1H), 6.94-6.90 (m, 2H), 6.62-6.56 (m, 3H), 6.32-6.24 (m, 2H) | 572.19 | 571.19 |
| 52 | δ = 7.77 (s, 4H), 7.75-7.73 (m, 1H), 7.61-7.44 (m, 11H), 7.40-7.35 (m, 3H), 7.32-7.30 (m, 1H), 7.08-7.03 (m, 2H), 6.86-6.82 (m, 2H), 6.76-6.72 (m, 2H), 6.67-6.62 (m, 1H), 6.23-6.19 (m, 2H) | 612.35 | 611.24 |
| 54 | δ = 8.90 (m, 1H), 8.60-8.58 (m, 1H0, 7.93-7.92 (m, 1H), 7.76 (s, 4H), 7.73-7.72 (m, 1H), 7.61-7.44 (m, 12H), 7.40-7.36 (m, 3H), 7.27-7.24 (m, 3H), 6.82-6.79 (m, 2H), 6.70-6.69 (m, 2H), 6.60-6.57 (m, 2H) | 689.26 | 688.26 |
| 60 | δ = 8.85 (m, 2H), 8.68-8.66 (m, 2H), 8.19-8.17 (m, 2H), 8.10-8.07 (ss, 2H), 8.04-8.02 (m, 2H), 7.76 (s, 4H), 7.75-7.73 (m, 1H), 7.70-7.66 (m, 4H), 7.59-7.46 (m, 12H), 7.40-7.38 (m, 2H), 7.32-7.30 (m, 1H), 7.26-7.19 (m, 4H) | 867.32 | 866.32 |
| 63 | δ = 8.53-8.52 (m, 1H), 8.47-8.46 (m, 1H), 7.92-7.88 (m, 2H), 7.78-7.73 (m, 2H), 7.62-7.60 (ss, 1H), 7.55-7.47 (m, 7H), 7.42-7.25 (m, 7H), 7.02-6.99 (m, 1H), 6.87-6.81 (m, 3H), 6.56-6.55 (m, 1H), 1.63 (s, 6H) | 653.26 | 652.26 |
| 65 | δ = 8.89 (m, 2H), 8.67-8.66 (m, 2H), 7.94-7.88 (m, 4H), 7.78-7.75 (m, 2H), 7.68-7.67 (t, 1H), 7.62-7.46 (m, 10H), 7.40-7.30 (m, 6H), 7.02 (d, 2H), 6.81-6.79 (m, 2H), 6.74-6.71 (dd, 1H), 6.53-6.52 (d, 1H), 1.63 (s, 6H) | 806.44 | 805.32 |
| 72 | δ = 7.79-7.76 (m, 2H), 7.63-7.60 (m, 2H), 7.52-7.46 (m, 7H), 7.42-7.29 (m, 9H), 7.11-7.09 (m, 2H), 6.73-6.66 (m, 3H), 6.53-6.51 (ss, 1H), 6.45-6.44 (d, 1H), 1.61 (s, 6H) | 652.27 | 651.27 |
| 76 | δ = 8.54-8.52 (m, 1H), 8.11-8.09 (m, 1H), 8.01 (d, 1H), 7.87-7.85 (m, 1H), 7.80-7.76 (m, 5H), 7.54-7.39 (m, 17H), 7.24-7.18 (m, 2H), 7.02-6.99 (m, 1H), 6.83-6.77 (m, 2H) | 638.25 | 637.25 |
| 79 | δ = 8.85 (s, 2H), 8.68-8.66 (m, 3H), 8.50-8.49 (m, 1H), 8.19-8.17 (m, 2H), 8.10-8.07 (ss, 2H), 8.02-8.01 (m, 2H), 7.87-7.85 (m, 2H), 7.78-7.76 (dd, 1H), 7.70-7.65 (m, 3H), 7.61-7.48 (m, 4H), 7.41-7.31 (m, 6H), 7.24-7.23 (ss, 1H), 7.03-6.99 (m, 1H) | 691.45 | 690.25 |

TABLE 1-continued

| Compound | $^1$H NMR (CDCl$_3$, 400 MHz) | MS/FAB found | calc. |
|---|---|---|---|
| 84 | δ = 8.98-8.97 (m, 1H), 8.38-8.36 (m, 1H), 8.20-8.13 (m, 2H), 7.79-7.73 (m, 3H), 7.60-7.57 (m, 3H), 7.51-7.41 (m, 6H), 7.32-7.31 (m, 2H), 7.06-7.01 (m, 4H), 6.65-6.61 (m, 1H), 6.51-6.48 (ss, 1H), 6.19-6.17 (m, 2H) | 587.52 | 586.22 |
| 88 | δ = 8.92 (m, 1H), 8.62-8.55 (m, 1H), 7.95-7.91 (m, 1H), 7.92-7.88 (m, 4H), 7.72-7.70 (m, 1H), 7.61-7.48 (m, 12H), 7.35-7.31 (m, 3H), 7.28-7.25 (m, 3H), 6.80-6.76 (m, 2H), 6.72-6.60 (m, 2H), 6.58-6.55 (m, 2H) | 688.25 | 688.26 |
| 92 | δ = 7.97 (s, 2H), 7.80-7.78 (m, 1H), 7.74-7.73 (m, 2H), 7.62-7.60 (ss, 1H), 7.55-7.47 (m, 7H), 7.40-7.35 (m, 3H), 7.32-7.30 (m, 1H), 7.25-7.22 (ss, 1H), 7.09-7.04 (m, 2H), 6.98 (m, 1H), 6.92-6.90 (dd, 1H), 6.86-6.83 (m, 2H), 6.67-6.62 (m, 1H), 6.37-6.33 (m, 2H) | 626.22 | 625.22 |

Example 1

To manufacture an anode, a Corning 15 Ω/cm² (1200 Å) ITO glass substrate was cut to a size of 50 mm×50 mm×0.7 mm and then sonicated in isopropyl alcohol and pure water for five minutes each, and then cleaned by irradiation of ultraviolet rays for 30 minutes and exposure to ozone. The resulting glass substrate was loaded into a vacuum deposition device.

4,4',4''-Tris(N-(2-naphthyl)-N-phenyl-amino)-triphenylamine (hereinafter, 2-TNATA), was vacuum-deposited on the anode to a thickness of 600 Å to form an HIL, and a known compound N,N'-di(1-naphthyl)-N,N'-diphenylbenzidine (hereinafter, NPB) as a hole transporting compound was vacuum-deposited on the HIL to a thickness of 300 Å to form an HTL.

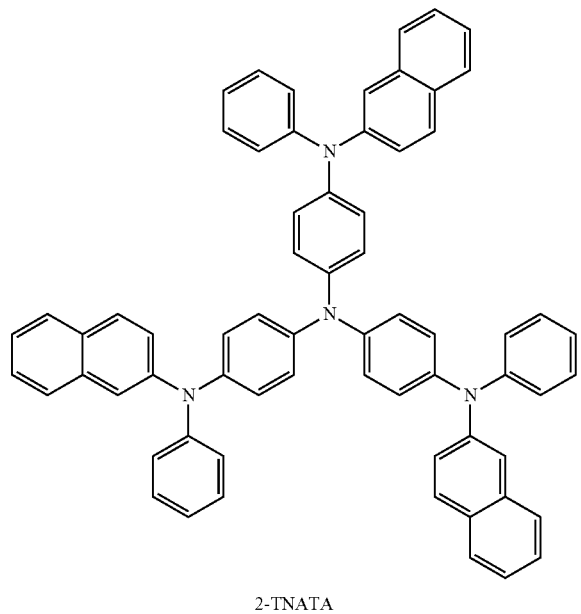

2-TNATA

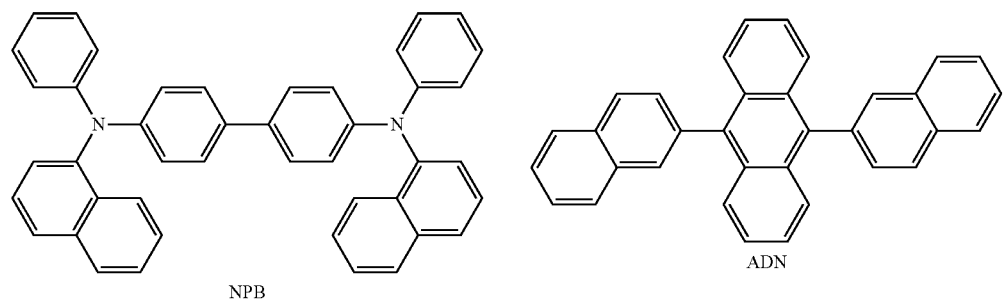

NPB

ADN

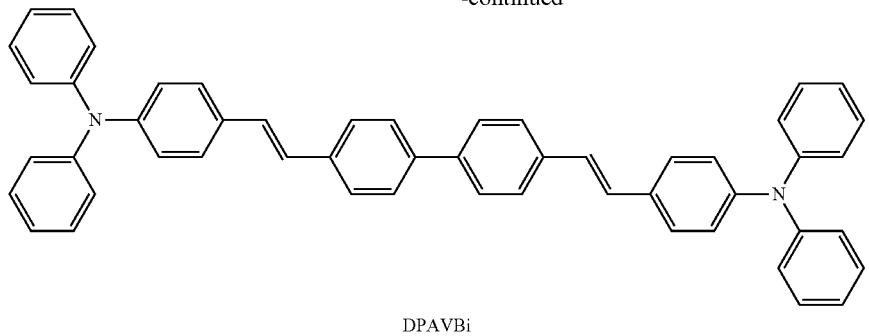

DPAVBi 9,10-Di-naphthalene-2-yl-anthracene (hereinafter, DNA), as a suitable blue fluorescent host, and 4,4'-bis[2-(4-(N,N-diphenylamino)phenyl)vinyl]biphenyl (hereinafter, DPAVBi) as a suitable blue fluorescent dopant, were co-deposited in a weight ratio of about 98:2 on the HTL to form an EML having a thickness of about 300 Å.

Then, Compound 2 of the present invention was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of about 5.05 V at a current density of 50 mA/cm$^2$, a luminosity of 3,020 cd/m$^2$, a luminescent efficiency of 5.76 cd/A, and a half life-span (hr @100 mA/cm$^2$) of about 273 hours.

Example 2

An organic light-emitting device was manufactured in the same manner as in Example 1, except that Compound 7 was used instead of Compound 2 to form the ETL.

The organic light-emitting device had a driving voltage of about 5.23 V at a current density of 50 mA/cm$^2$, a luminosity of 3,175 cd/m$^2$, a luminescent efficiency of 5.92 cd/A, and a half life-span (hr @100 mA/cm$^2$) of about 287 hours.

Example 3

An organic light-emitting device was manufactured in the same manner as in Example 1, except that Compound 13 was used instead of Compound 2 to form the ETL.

The organic light-emitting device had a driving voltage of about 5.18 V at a current density of 50 mA/cm$^2$, a luminosity of 3,750 cd/m$^2$, a luminescent efficiency of 5.68 cd/A, and a half life-span (hr @100 mA/cm$^2$) of about 304 hours.

Example 4

An organic light-emitting device was manufactured in the same manner as in Example 1, except that Compound 36 was used instead of Compound 2 to form the ETL.

The organic light-emitting device had a driving voltage of about 5.27 V at a current density of 50 mA/cm$^2$, a luminosity of 3,805 cd/m$^2$, a luminescent efficiency of 5.97 cd/A, and a half life-span (hr @100 mA/cm$^2$) of about 310 hours.

Example 5

An organic light-emitting device was manufactured in the same manner as in Example 1, except that Compound 42 was used instead of Compound 2 to form the ETL.

The organic light-emitting device had a driving voltage of about 5.30 V at a current density of 50 mA/cm$^2$, a luminosity of 3,460 cd/m$^2$, a luminescent efficiency of 5.81 cd/A, and a half life-span (hr @100 mA/cm$^2$) of about 318 hours.

Example 6

An organic light-emitting device was manufactured in the same manner as in Example 1, except that Compound 47 was used instead of Compound 2 to form the ETL.

The organic light-emitting device had a driving voltage of about 5.33 V at a current density of 50 mA/cm$^2$, a luminosity of 3,325 cd/m$^2$, a luminescent efficiency of 6.03 cd/A, and a half life-span (hr @100 mA/cm$^2$) of about 301 hours.

Example 7

An organic light-emitting device was manufactured in the same manner as in Example 1, except that Compound 54 was used instead of Compound 2 to form the ETL.

The organic light-emitting device had a driving voltage of about 5.40 V at a current density of 50 mA/cm$^2$, a luminosity of 3,810 cd/m$^2$, a luminescent efficiency of 6.22 cd/A, and a half life-span (hr @100 mA/cm$^2$) of about 365 hours.

Example 8

An organic light-emitting device was manufactured in the same manner as in Example 1, except that Compound 65 was used instead of Compound 2 to form the ETL.

The organic light-emitting device had a driving voltage of about 5.16 V at a current density of 50 mA/cm$^2$, a luminosity of 3,865 cd/m$^2$, a luminescent efficiency of 6.35 cd/A, and a half life-span (hr @100 mA/cm$^2$) of about 360 hours.

Example 9

An organic light-emitting device was manufactured in the same manner as in Example 1, except that Compound 76 was used instead of Compound 2 to form the ETL.

The organic light-emitting device had a driving voltage of about 5.29 V at a current density of 50 mA/cm$^2$, a luminosity of 3,540 cd/m$^2$, a luminescent efficiency of 6.07 cd/A, and a half life-span (hr @100 mA/cm$^2$) of about 307 hours.

Example 10

An organic light-emitting device was manufactured in the same manner as in Example 1, except that Compound 77 was used instead of Compound 2 to form the ETL.

The organic light-emitting device had a driving voltage of about 5.31 V at a current density of 50 mA/cm², a luminosity of 3,970 cd/m², a luminescent efficiency of 6.19 cd/A, and a half life-span (hr @100 mA/cm²) of about 322 hours.

Example 11

An organic light-emitting device was manufactured in the same manner as in Example 1, except that Compound 84 was used instead of Compound 2 to form the ETL.

The organic light-emitting device had a driving voltage of about 5.15 V at a current density of 50 mA/cm², a luminosity of 3,905 cd/m², a luminescent efficiency of 6.01 cd/A, and a half life-span (hr @100 mA/cm²) of about 316 hours.

Example 12

An organic light-emitting device was manufactured in the same manner as in Example 1, except that Compound 88 was used instead of Compound 2 to form the ETL.

The organic light-emitting device had a driving voltage of about 5.12 V at a current density of 50 mA/cm², a luminosity of 3,875 cd/m², a luminescent efficiency of 6.27 cd/A, and a half life-span (hr @100 mA/cm²) of about 335 hours.

Comparative Example 1

An organic light-emitting device was manufactured in the same manner as in Example 1, except that a known compound Alq₃ was used instead of Compound 2 to form the ETL.

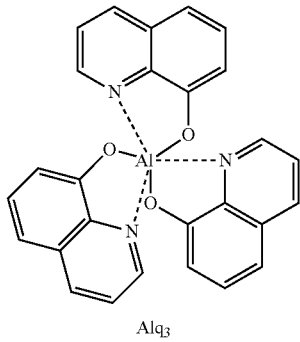

Alq₃

The organic light-emitting device had a driving voltage of about 7.35 V at a current density of 50 mA/cm², a luminosity of 2,065 cd/m², a luminescent efficiency of 4.13 cd/A, and a half life-span (hr @100 mA/cm²) of about 145 hours.

Comparative Example 2

An organic light-emitting device was manufactured in the same manner as in Example 1, except that Compound 500 below was used instead of Compound 2 to form the ETL.

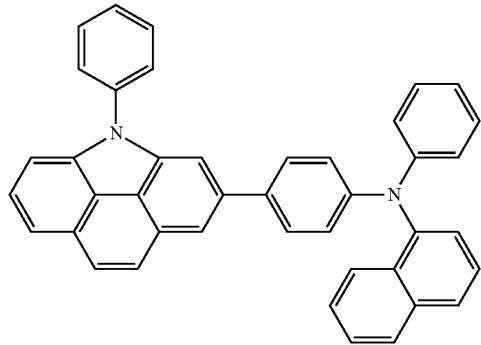

<Compound 500>

The organic light-emitting device had a driving voltage of about 5.50 V at a current density of 50 mA/cm², a luminosity of 3,020 cd/m², a luminescent efficiency of 5.57 cd/A, and a half life-span (hr @100 mA/cm²) of about 175 hours.

The heterocyclic arylamine compounds represented by Formula 1 according to embodiments were used as ETL materials in organic light-emitting devices and their performances were evaluated. When the heterocyclic arylamine compounds represented by Formula 1 according to embodiments were used as ETL materials, at least 1 V of the driving voltage was lowered and I-V-L characteristics were improved in each of the organic light-emitting devices compared to when a known material Alq₃ and Compound 500 were used. In particular, the organic light-emitting devices according to the embodiments had markedly improved lifetimes. As a result, it has been demonstrated that the arylamine compounds including the novel heterocyclic compounds according to embodiments of the present invention are markedly effective as electron transporting materials. The results and lifetimes of the organic light-emitting devices of Examples 1-12 and Comparative Examples 1 and 2 are shown in Table 1 below.

TABLE 1

|  | ETL material | Driving voltage (V) | Current density (mA/cm²) | Luminance (cd/m²) | Efficiency (cd/A) | Emission color | Half-life span (hr@100 mA/cm²) |
|---|---|---|---|---|---|---|---|
| Example 1 | 2 | 5.05 | 50 | 3,020 | 5.76 | Blue | 273 hr |
| Example 2 | Compound 7 | 5.23 | 50 | 3,175 | 5.92 | Blue | 287 hr |
| Example 3 | Compound 13 | 5.18 | 50 | 3,750 | 5.68 | Blue | 304 hr |
| Example 4 | Compound 36 | 5.27 | 50 | 3.805 | 5.97 | Blue | 310 hr |
| Example 5 | Compound 42 | 5.30 | 50 | 3,460 | 5.81 | Blue | 318 hr |
| Example 6 | Compound 47 | 5.33 | 50 | 3,325 | 6.03 | Blue | 301 hr |
| Example 7 | Compound 54 | 5.40 | 50 | 3,810 | 6.22 | Blue | 365 hr |
| Example 8 | Compound 65 | 5.16 | 50 | 3,865 | 6.35 | Blue | 360 hr |
| Example 9 | Compound 76 | 5.29 | 50 | 3,540 | 6.07 | Blue | 307 hr |
| Example 10 | Compound 77 | 5.31 | 50 | 3,970 | 6.19 | Blue | 322 hr |
| Example 11 | Compound 84 | 5.15 | 50 | 3,905 | 6.01 | Blue | 316 hr |
| Example 12 | Compound 88 | 5.12 | 50 | 3,875 | 6.27 | Blue | 335 hr |

TABLE 1-continued

|  | ETL material | Driving voltage (V) | Current density (mA/cm$^2$) | Luminance (cd/m$^2$) | Efficiency (cd/A) | Emission color | Half-life span (hr@100 mA/cm$^2$) |
|---|---|---|---|---|---|---|---|
| Comparative Example 1 | Alq$_3$ | 7.35 | 50 | 2,065 | 4.13 | Blue | 145 hr |
| Comparative Example 2 | Compound 500 | 5.50 | 50 | 3,020 | 5.57 | Blue | 175 hr |

The novel heterocyclic compound represented by Formula 1 above has an improved charge transporting capability, and so, can be used as an electron injecting material or an electron transporting material that is suitable for any color fluorescent and phosphorescent devices, such as red, green, blue, and white fluorescent and phosphorescent devices. Therefore, organic light-emitting devices having high efficiency, low driving voltages, high luminance, and long lifetimes may be manufactured using the compounds.

While the present invention has been particularly shown and described with reference to exemplary embodiments thereof, it will be understood by those of ordinary skill in the art that various changes in form and details may be made therein without departing from the spirit and scope of the present invention as defined by the following claims and equivalents thereof.

What is claimed is:

1. A heterocyclic compound represented by Formula 1 below:

<Formula 1>

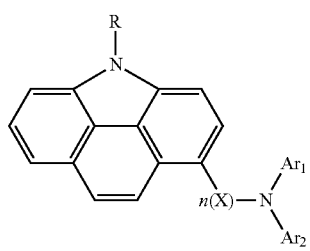

wherein, in Formula 1,

R is a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

X is a divalent linking group that is a substituted or unsubstituted C6-C60 arylene group, or a substituted or unsubstituted C6-C60 condensed polycyclic group; and Ar$_1$ or Ar$_2$ is independently a substituted or unsubstituted C6-C60 aryl group, a substituted or unsubstituted C2-C60 heteroaryl group, or a substituted or unsubstituted C6-C60 condensed polycyclic group, wherein at least one of Ar$_1$ and Ar$_2$ is a C6-C60 aryl group that is substituted with an electron-attracting moiety, and n is an integer from 0 to 10.

2. The heterocyclic compound of claim 1, wherein the electron-attracting moiety is F; —CN; a C1-C60 alkyl group substituted with at least one —F; a C2-C60 heteroaryl group; or a C2-C60 heteroaryl group substituted with at least one selected from a deuterium atom, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid or a salt thereof, a C1-C60 alkyl group, a C1-C60 alkoxy group, a C2-C60 alkenyl group, a C2-C60 alkynyl group, a C6-C60 aryl group, and a C2-C60 heteroaryl group.

3. The heterocyclic compound of claim 1, wherein, in Formula 1, R is one of the groups represented by Formulae 2a to 2d below:

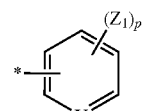

2a

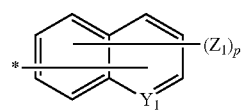

2b

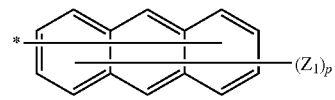

2c

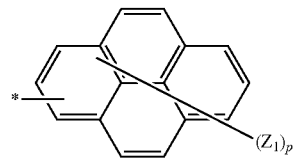

2d wherein, in Formulae 2a to 2d,

Z$_1$ is a hydrogen atom, a deuterium atom, a halogen atom, —CN, a substituted or unsubstituted C1-C20 alkyl group, a substituted or unsubstituted C6-C20 aryl group, or a substituted or unsubstituted C2-C20 heteroaryl group;

Y$_1$ is —CH= or —N=;

p is an integer from 1 to 9; and

* indicates a binding site.

4. The heterocyclic compound of claim 1, wherein, in Formula 1, X is one of the groups represented by Formulae 3a to 3d below:

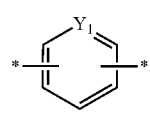

3a

-continued

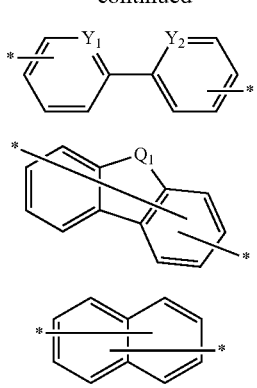

3b

3c

3d wherein, in Formulae 3a to 3d,
Y$_1$ and Y$_2$ are each independently —CH═ or —N═;
Q$_1$ is a linking group represented by —C(R$_{30}$)(R$_{31}$)—, —S—, or —O—;
R$_{30}$ and R$_{31}$ are each independently a hydrogen atom, a deuterium atom, a substituted or unsubstituted C1-C20 alkyl group, a substituted or unsubstituted C6-C20 aryl group, or a substituted or unsubstituted C6-C20 condensed polycyclic group; and
* indicates a binding site.

5. The heterocyclic compound of claim 1, wherein, in Formula 1, Ar$_1$ and Ar$_2$ are each independently one of the groups represented by Formulae 4a to 4d below:

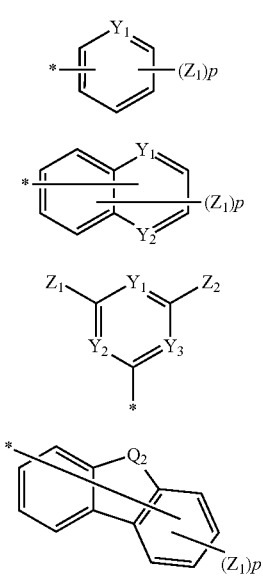

4a

4b

4c

4d wherein, in Formulae 4a to 4d,
Y$_1$ to Y$_3$ are each independently —CH═ or —N═;
Q$_2$ is a linking group represented by —C(R$_{30}$)(R$_{31}$)—, —S—, or —O—;
Z$_1$, Z$_2$, R$_{30}$ and R$_{31}$ are each independently a hydrogen atom; a deuterium atom; —F; —CN; a C1-C60 alkyl group substituted with at least one —F; a C2-C60 heteroaryl group; a substituted or unsubstituted C6-C20 aryl group; or a C2-C60 heteroaryl group substituted with at least one selected from a deuterium atom, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid or a salt thereof, a C1-C60 alkyl group, a C1-C60 alkoxy group, a C2-C60 alkenyl group, a C2-C60 alkynyl group, a C6-C60 aryl group, and a C2-C60 heteroaryl group;
p is an integer from 1 to 7; and
* indicates a binding site.

6. The heterocyclic compound of claim 1, wherein the compound of Formula 1 is one of the following compounds:

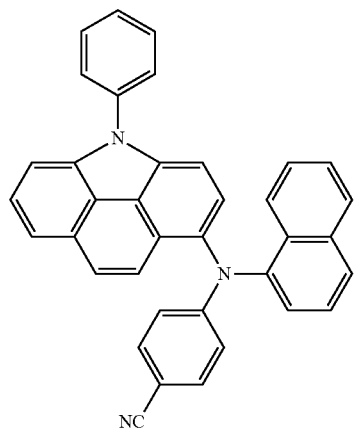

2

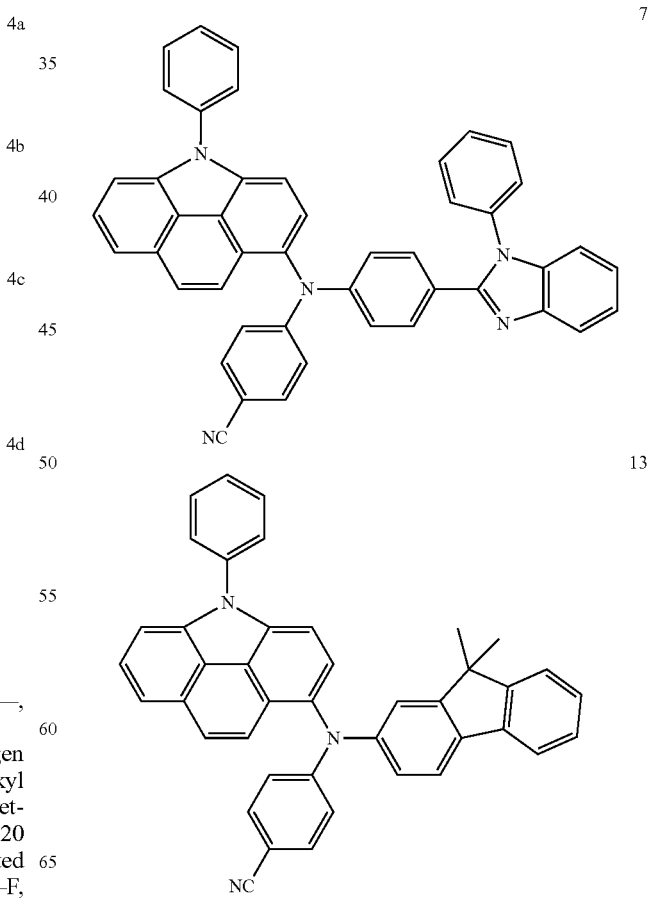

7

13

107
36
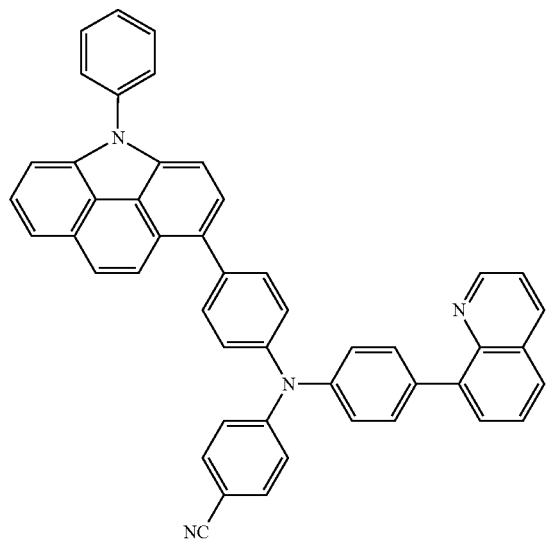
42
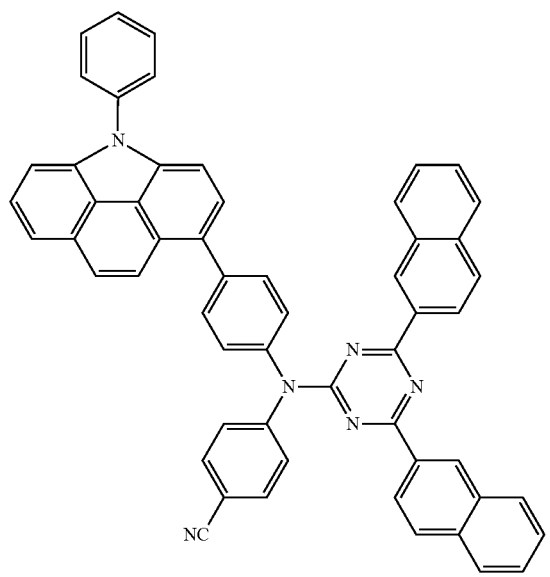
108
47
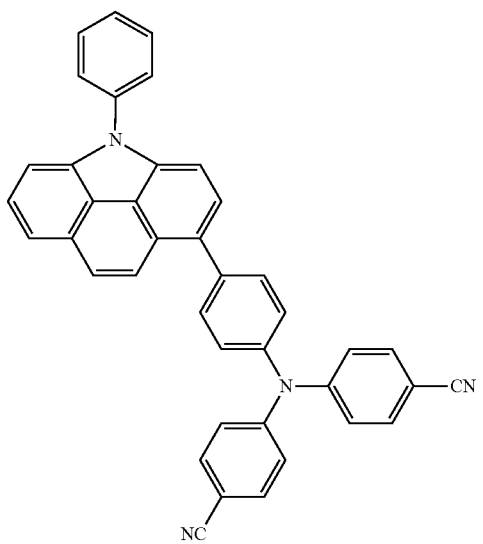
54
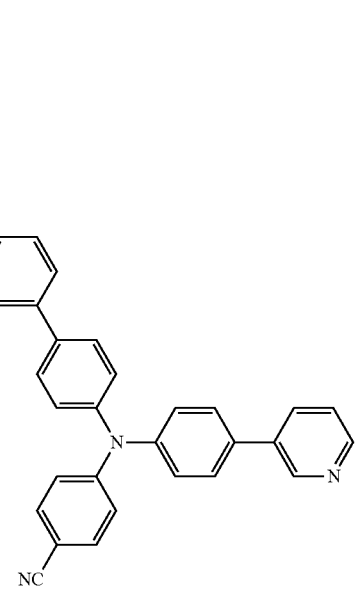

109
-continued

110
-continued

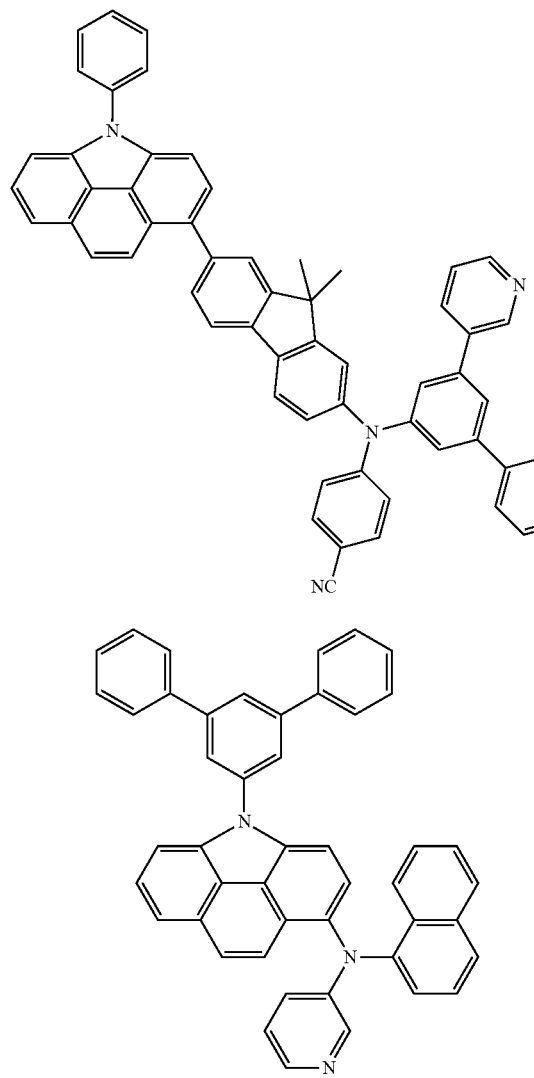

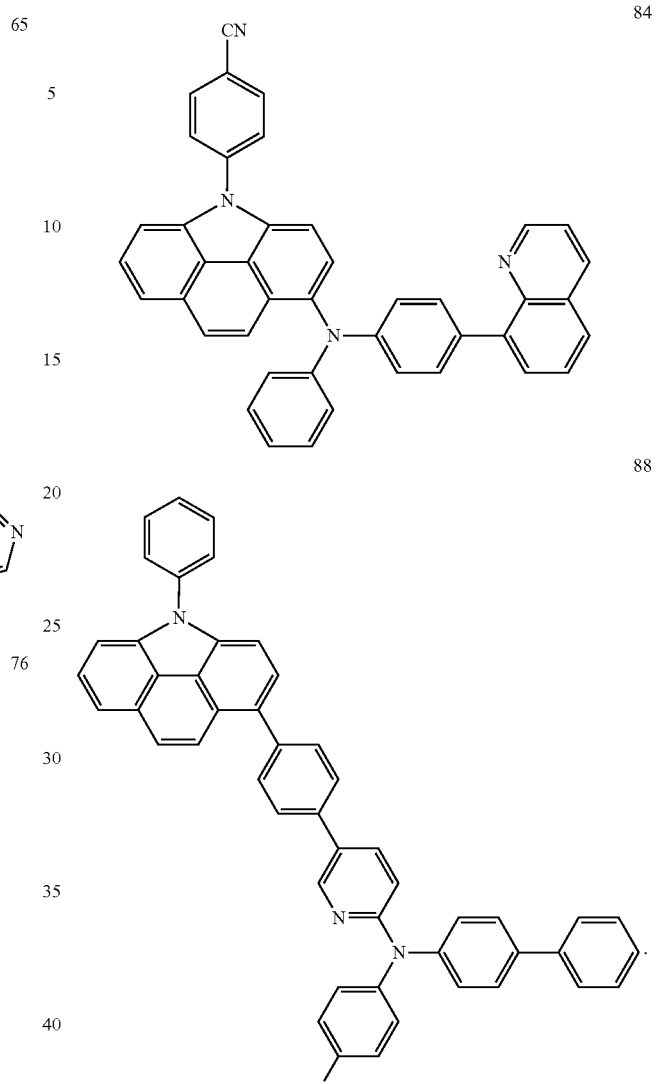

7. An organic light-emitting device comprising:
 a first electrode;
 a second electrode; and
 an organic layer between the first electrode and the second electrode, wherein the organic layer comprises a heterocyclic compound, and wherein the heterocyclic compound is represented by Formula 1 below:

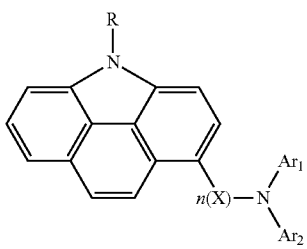

<Formula 1> wherein, in Formula 1,
 R is a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

X is a divalent linking group that is a substituted or unsubstituted C6-C60 arylene group, or a substituted or unsubstituted C6-C60 condensed polycyclic group; and $Ar_1$ or $Ar_2$ is independently a substituted or unsubstituted C6-C60 aryl group, a substituted or unsubstituted C2-C60 heteroaryl group, or a substituted or unsubstituted C6-C60 condensed polycyclic group, wherein at least one of $Ar_1$ and $Ar_2$ is a C6-C60 aryl group that is substituted with an electron-attracting moiety, and n is an integer from 0 to 10.

8. The organic light-emitting device of claim 7, wherein the organic layer is an electron injection layer, an electron transport layer, or a functional layer having both electron injection and transport capabilities.

9. The organic light-emitting device of claim 7, wherein the organic layer comprises an emission layer; at least one of an electron injection layer, an electron transport layer, or a functional layer having both electron injection and transport capabilities; and at least one of a hole injection layer, a hole transport layer, or a functional layer having both hole injection and transport capabilities, wherein the at least one of the electron injection layer, the electron transport layer, or the functional layer having both electron injection and transport capabilities comprises the heterocyclic compound, and wherein the emission layer comprises an anthracene-based compound, an arylamine-based compound, or a styryl-based compound.

10. The organic light-emitting device of claim 7, wherein the organic layer comprises an emission layer; at least one of an electron injection layer, an electron transport layer, or a functional layer having both electron injection and transport capabilities; and at least one of a hole injection layer, a hole transport layer, or a functional layer having both hole injection and transport capabilities, wherein the at least one of the electron injection layer, the electron transport layer, and the functional layer having both electron injection and transport capabilities comprises the heterocyclic compound, and wherein the emission layer comprises at least one of a red emission layer, a green emission layer, a blue emission layer, or a white emission layer, at least one of which comprises a phosphorescent compound.

11. The organic light-emitting device of claim 10, wherein the at least one of the hole injection layer, the hole transport layer, and the functional layer having both hole injection and hole transport capabilities comprises a charge-generating material.

12. The organic light-emitting device of claim 11, wherein the charge generating material is a p-dopant.

13. The organic light-emitting device of claim 12, wherein the p-dopant is a quinone derivative.

14. The organic light-emitting device of claim 12, wherein the p-dopant is a metal oxide.

15. The organic light-emitting device of claim 12, wherein the p-dopant is a cyano group-containing compound.

16. The organic light-emitting device of claim 7, wherein the organic layer comprises an electron transport layer, wherein the electron transport layer further comprises a metal complex.

17. The organic light-emitting device of claim 16, wherein the metal complex is a lithium complex.

18. The organic light-emitting device of claim 16, wherein the metal complex is a lithium quinolate (LiQ).

19. The organic light-emitting device of claim 7, wherein the organic layer is formed from the heterocyclic compound using a wet process.

20. A flat panel display device comprising the organic light-emitting device of claim 7, wherein the first electrode of the organic light-emitting device is electrically connected to a source electrode or a drain electrode of a thin-film transistor.

* * * * *